(12) United States Patent
Cabilly et al.

(10) Patent No.: US 6,331,415 B1
(45) Date of Patent: Dec. 18, 2001

(54) METHODS OF PRODUCING IMMUNOGLOBULINS, VECTORS AND TRANSFORMED HOST CELLS FOR USE THEREIN

(75) Inventors: Shmuel Cabilly, Monrovia; Herbert L. Heyneker, Burlingame; William E. Holmes, Pacifica; Arthur D. Riggs, La Verne; Ronald B. Wetzel, San Francisco, all of CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 07/205,419

(22) Filed: Jun. 10, 1988

Related U.S. Application Data

(63) Continuation of application No. 06/483,457, filed on Apr. 8, 1983, now Pat. No. 4,816,567.

(51) Int. Cl.[7] .......................... C12N 15/13; C12N 15/00; C12N 15/63

(52) U.S. Cl. .............. 435/69.6; 435/69.1; 435/69.7; 435/70.1; 435/70.21; 435/71.1; 435/71.2; 435/320; 435/252.1; 435/252.3; 435/252.33; 435/254.11; 435/254.2; 435/254.21; 435/455; 435/471; 435/483; 435/485

(58) Field of Search .................... 435/69.1, 69.7, 435/71.1, 70.1, 71.2, 320, 261, 252.1, 252.3, 81, 55, 56, 69.6, 252.33, 254.21, 483

(56) References Cited

U.S. PATENT DOCUMENTS

| | | |
|---|---|---|
| 4,179,337 | 12/1979 | Davis et al. . |
| 4,237,224 | 12/1980 | Cohen . |
| 4,338,397 | 7/1982 | Gilbert et al. . |
| 4,342,832 | 8/1982 | Goeddel et al. . |
| 4,403,036 | 9/1983 | Hartley et al. . |
| 4,444,878 | 4/1984 | Paulus . |
| 4,510,244 | 4/1985 | Parks et al. . |
| 4,512,922 | 4/1985 | Jones et al. . |
| 4,518,584 | 5/1985 | Mark et al. . |
| 4,642,334 | 2/1987 | Moore et al. . |
| 4,704,362 | 11/1987 | Itakura et al. . |
| 4,816,397 | 3/1989 | Boss et al. . |
| 4,816,567 | 3/1989 | Cabilly et al. . |
| 5,225,539 | 7/1993 | Winter . |
| 5,545,403 | 8/1996 | Page . |
| 5,545,404 | 8/1996 | Page . |
| 5,545,405 | 8/1996 | Page . |

FOREIGN PATENT DOCUMENTS

| | | |
|---|---|---|
| 194982 | 2/1983 | (AU) . |
| 12417/83 | 9/1983 | (AU) . |
| B-26429/84 | 10/1984 | (AU) . |
| 46556/85 | 3/1986 | (AU) . |
| 65981/86 | 5/1987 | (AU) . |
| 0037723 | 10/1981 | (EP) . |
| 37723 | 10/1981 | (EP) . |
| 041313 | 12/1981 | (EP) . |
| 041767 | 12/1981 | (EP) . |
| 41313 | 12/1981 | (EP) . |
| 41767 | 12/1981 | (EP) . |
| 044722 | 1/1982 | (EP) . |
| 055945 | 7/1982 | (EP) . |
| 57107 | 8/1982 | (EP) . |
| 0068763 | 1/1983 | (EP) . |
| 68763 | 1/1983 | (EP) . |
| 0057107 | 3/1983 | (EP) . |
| 0073656 | 3/1983 | (EP) . |
| 075444 | 3/1983 | (EP) . |
| 73656 | 3/1983 | (EP) . |
| 75444 | 3/1983 | (EP) . |
| A-073656 | 3/1983 | (EP) . |
| 088994 | 9/1983 | (EP) . |
| 88994 | 9/1983 | (EP) . |
| 093619 | 11/1983 | (EP) . |
| 0120694 | 10/1984 | (EP) . |
| 0125023 | 11/1984 | (EP) . |
| 194276 | 9/1986 | (EP) . |
| 196864 | 10/1986 | (EP) . |
| 234592 | 9/1987 | (EP) . |
| 255694 | 2/1988 | (EP) . |
| 324162 | 7/1989 | (EP) . |
| 550400 | 7/1993 | (EP) . |
| 08235 | 3/1987 | (GB) . |
| 62 201 581 | 9/1987 | (JP) . |
| WO 86/01533 | 3/1986 | (WO) . |

OTHER PUBLICATIONS

Dolby et al. *Proc. Natl. Acad. Sci.* 77(10):6027–6031 (1980).
Rice et al. *Proc. Natl. Acad. Sci.* 77:7862–7865 (1982).
Accolla et al. *Proc. Natl. Acad. Sci.* 77(1):563–566 (1980).
Raso et al. *Cancer Res.* 41:2073–2078 (1981).
Nisonoff et al. *Arch. Biochem. Biophys.* 93:460–462 (1960).
Glennie et al. *Nature* 295:712–714 (1982).
Eisen *Immunology* Harper & Row, Publishers, pp. 415 and 428–436 (1974).
Hozumi et al. *Nuc. Acids. Res.* 5(6):1779–1799 (1978).
Wetzel et al. *Gene* 16:63–71 (1981).
Williams et al. *Science* 215:687–689 (1982).
Falkner et al. *Nature* 298:286–288 (1982).
Boss et al. *Gene Expressions–Proc. Cetus–UCLA Symposium* pp. 513–522, Mar. 26–Apr. 1, 1983.

(List continued on next page.)

*Primary Examiner*—Phillip Gambel
(74) *Attorney, Agent, or Firm*—Burns, Doane, Swecker & Mathis, LLP

(57) ABSTRACT

The invention relates to processes for producing an immunoglobulin or an immunologically functional immunoglobulin fragment containing at least the variable domains of the immunoglobulin heavy and light chains. The processes can use one or more vectors which produce both the heavy and light chains or fragments thereof in a single cell. The invention also relates to the vectors used to produce the immunoglobulin or fragment, and to cells transformed with the vectors.

36 Claims, 19 Drawing Sheets

OTHER PUBLICATIONS

Amster et al. *Nucleic Acid Research* 8(9):2055–2065 (1980).
DeBoer et al., Rodriguez et al. (Ed.) *Promoters* 462–481 (1982).
Gough *Tibs* 6(8):203–205 (Aug., 1981).
Morrison *J. of Immunology* 123(2):793–800 (Aug., 1979).
Kohler *Proc. Natl. Acad. Sci.* 77(4):2197–2199 (Apr., 1980).
Roberts *Promoters* 452–461 (1982).
Kemp et al. *Proc. Natl. Acad. Sci.* 78(7):4520–4524 (Jul., 1981).
Valle et al. *Nature* 300:71–74 (Nov. 4, 1982).
*Microbiology* 3rd edition, Harper Int. Ed. 338–379 (1980).
Hitzeman et al. *Science* 219:620–625 (1983).
Mercereau–Puijalon et al. in Expression of Eukaryotic Viral and Cellular Genes, Pettersson et al. (ED) 295–303 (1981) Academic Press.
Pettersson et al. (Ed.) 295–303 (1981) Academic Pr.
Keshet et al. *Nucleic Acids Res.* 9(1):19–30 (1981).
Taniguchi et al. *Proc. Natl. Acad. Sci.* 77(9):5230–5233 (1980).
Ohsuye et al. *Nucleic Acids Res.* 11(5):1283–1295 (1983).
Kadonaga et al. *J. Biol. Chem.* 259(4):2149–2154 (1984).
Maniatis *Molecular Cloning* p. 433 (Sep., 1985).
Fujisawa et al. *Nucleic Acids Res.* 11(11):3581–3591 (1983).
Roberts *Promoters Structures and Function* Rodriguez, R. L. (Ed.) 452–461 (1982).
Adams et al. *Biochemistry* 19:2711–2719 (1980).
Haley et al. *DNA* 1:155–162 (1982).
Gough et al. *Biochemistry* 19:2702–2710 (1980).
Iserentant et al. *Gene* 9:1–12 (1980).
Seidman et al. *Nature* 271:582–585 (1978).
Stevens et al. *J. Mol. Biol.* 78:517–525 (1973).
Deacon et al. *Biochem. Soc. Trans.* 4:818–820 (1976).
Colman et al. *Cell* 17:517–526 (1979).
Valle et al. *Nature* 291:338–340 (1981).
Colman et al. *J. Mol. Biol.* 160:459–474 (Sep., 1982).
Cowan et al. *J. Mol. Biol.* 90:691–701 (1974).
Morrison et al. *J. Immunol.* 114:655–659 (1975).
Mosmann et al. *J. Immunol.* 115:955–962 (1975).
Levy et al. *Proc. Nat. Acad. Sci.* 75:2411–2415 (1978).
Robertson et al. *Nature* 287:390–392 (1980).
Mosmann et al. *Cell* 20:283–292 (1980).
Wilde et al. *Eur. J. Immunol.* 10:462–467 (1980).
Ochi et al. *Nature* 302:340–342 (Mar. 24, 1983).
Kemp et al. in Nagley et al., Ed., *Manipulation and Expression of Genes in Eukaryotes* Proceedings of an International Conference, 12th International Congress of Biochemistry, in Australia Aug. 9–13, 1982 (1983).
Picard et al. *Proc. Nat. Acad. Sci.* 80:417–421 (Jan., 1983).
Oi et al. *Proc. Nat. Acad. Sci.* 80:825–829 (Feb., 1983).
Hawley et al. *Proc. Nat. Acad. Sci.* 79:7425–7429 (Dec., 1982).
Boss et al. *Immunology Today* 6(1):12–13 (1985).
Lewin, Ed. *Genes* 3rd Edition, 359–360 (1987).
Skerra et al. *Science* 240:1038–1040 (1988).
Kohler et al. *Eur. J. Immunol.* 6:292–295 (1976).
Adair et al., "Engineering Antibodies for Therapy" *Immunological Reviews* 130:5–40 (1992).
Adelman et al., "In Vitro Deletional Mutagenesis for Bacterial Production of the 20,000–Dalton Form of Human Pituitary Growth Hormone" *DNA* 2(3):183–193 (1983).
Adetugbo, K., "Spontaneous Somatic Mutations" *Journal of Biological Chemistry* 253(17):6076–6080 (1978).

Alt et al., "Activity of Multiple Light Chain Genes in Murine Myeloma Cells Producing a Single, Functional Light Chain" *Cell* 21:1–12 (Aug. 1980).
Alt et al., "Joining of immunoglobulin heavy chain gene segments: Implications from a chromosome with evidence of three D–$J_H$ fusions" *Proc. Natl. Acad. Sci. USA* 79:4118–4122 (Jul. 1982).
Alt et al., "Multiple Immunoglobulin Heavy–Chain Gene Transcripts in Abelson Murine Leukemia Virus–Transformed Lymphoid Cell Lines" *Molecular & Cellular Biology* 2(4):386–400 (Apr. 1982).
Alt et al., "Organization and Reorganization of Immunoglobulin Genes in A–MuLV–Transformed Cells: Rearrangement of Heavy but Not Light Chain Genes" *Cell* 27:381–390 (Dec. 1981).
Altenburger et al., "Functional and non–functional joining in immunoglobulin light chain genes of a mouse myeloma" *Nature* 287:603–607 (Oct. 16, 1980).
Amzel and Poljak, "Three–dimensional structure of immunoglobulins" *Ann. Rev. Biochem.* 48:961–997 (1979).
Astaldi et al., "Increase of hybridoma formation by human lymphocytes after stimulation in vitro; effect of antigen, endothelial cells, and PWM" *J. Immunol.* 128(6):2539–2542 (1982).
August, "Monoclonal Antibodies—I: Discussion" *Cell Fusion: Gene Transfer and Transformation*, Beers et al. pp. 345–351 (1984).
Barnett–Foster and Painter, "The interaction of the Facb fragment of rabbit anti–sheep red cell IgG with guinea pig macrophages, and human monocytes and granulocytes" *Molecular Immunology* 19(2):247–252 (1982).
Bernard and Gough, "Nucleotide sequence of immunoglobulin heavy chain joining segments between translocated $V_H$ and $\mu$ constant region genes" *Proc. Natl. Acad. Sci. USA* 77(6):3630–3634 (1980).
Bernard et al., "Plasmacytomas with more than one immunoglobulin κ mRNA: Implications for allelic exclusion" *Proc. Natl. Acad. Sci. USA* 78(9):5812–5816 (Sep. 1981).
Bernstein et al., "Monoclonal Antibody Therapy of Mouse Leukemia" *Monoclonal Antibodies*, Kennett et al., Plenum Press pp. 275–291 (1980).
Better and Horwitz, "Expression of engineered antibodies and antibody fragments in microorganisms" *Methods in Enzymology* 178:476–496 (1989).
Better et al., "*Escherichia coli* secretion of an active chimeric antibody fragment" *Science* 240:1041–1043 (1988).
Bevan et al,. "Biosynthesis of immunoglobulins" *Progress In Biophysics and Molecular Biology*, Butler and Noble, Pergamon Press pp. 133–162 (1972).
Birshtein et al., "Effects of immunoglobulin structure on Fc receptor binding: a mouse myeloma variant immunoglobulin with a γ2b–γ2a hybrid heavy chain having a complete γ2a Fc region fails to bind a γ2a Fc receptors on mouse macrophages" *J. Immunol.* 129(2):610–614 (1982).
Blythman et al., "Immunotoxins: hybrid molecules of monclonal antibodies and a toxin subunit specifically kill tumour cells" *Nature* 290:145–146 (1981).
Bobrzecka et al., "The method of controlled rearrangement of protein disulphides and its use for synthesis of chimeric immunoglobulin G" *Immunology Letters* 2:151–155 (1980).
Bock et al., "Cloning and expression of the cDNA for human antithrombin III" *Nucleic Acids Research* 10(24):8113–8125 (1982).

Bock et al., "Hybridization–selected translation of Bombyx mori high–cysteine chorion proteins in *Xenopus laevis* oocytes" *Proc. Natl. Acad. Sci. USA* 79:1032–1036 (1982).

Boss et al., "Assembly of functional antibodies from immunoglobulin heavy and light chains synthesised in E. coli" *Nucleic Acids Research* 12(9):3791–3806 (1984).

Boss et al., "Production of immunoglobulin molecules in *Escherichia coli*" *J. Cell. Biochem.* (Abstract Only) Supplement 7A:140 (0364) (1983).

Bothwell et al., "Dual expression of $\lambda$ genes in the MOPC–315 plasmacytoma" *Nature* 290:65–67 (1981).

Bothwell et al., "Heavy chain variable region contribution to the $NP^b$ family of antibodies: somatic mutation evident in a $\gamma$2a variable region" *Cell* 24:625–637 (1981).

Bothwell et al., "Somatic variants of murine immunoglobulin $\alpha$ light chains" *Nature* 298:380–382 (Jul. 22, 1982).

Boulianne et al., "Production of functional chimaeric mouse/human antibody" *Nature* 312:643–646 (Dec. 13, 1984).

Boulianne et al., "The production of chimeric mouse/human antibodies" *Abstracts of papers presented at the meeting on Cellular and Molecular Biology of Neoplasia* (Abstract only) pp. #25 (1983).

Boyd et al., "Human monoclonal antibodies—production and potential" *Trends in Biotechnology* 2(3):70–77 (1984).

Boyden, Alan, "Homology and Analogy" *Science* 164:455–456 (Apr. 1969).

Boylston et al., "Production of human IgM anti–D in tissue culture by EB–virus–transformed lymphocytes" *Scand. J. Immunol.* 12:355–358 (1980).

Bruggemann et al., "Immunoglobulin V region variants in hybridoma cells. I. Isolation of a variant with altered idiotypic and antigen binding specificity" *EMBO Journal* 1(5):629–634 (1982).

Buchner et al., "Renaturation, purification and characterization of recombinant Fab–fragments produced in *Escherichia coli*" *Bio/Technology* 9:157–162 (1991).

Burrows et al., "Evidence that murine pre–B cells synthesize o heavy chains but no light chains" *Nature* 280:838–841 (Aug. 30, 1979).

Cabilly et al., "Generation of Antibody Activity from Immunoglobulin Polypeptide Chains Produced in *Escherichia coli*" *Proc. Natl. Acad. Sci. USA* 81:3273–3277 (1984).

Chang et al., "Construction and characterization of amplifiable multicopy DNA cloning vehicles derived from the P15A cryptic miniplasmid" *J. Bacteriol.* 134(3):1141–1156 (1978).

Cheng et al., "Effect of deglycosylation on the binding and immunoreactivity of human thyroxine–binding globulin" *Journal of Biological Chemistry* 254(18):8830–8835 (Sep. 25, 1979).

Choi et al., "RNA splicing generates a variant light chain from an aberrantly rearranged κ gene" *Nature* 286:776–779 (Aug. 21, 1980).

Coffino and Laskov, "Immunoglobulin production: method for quantitatively detecting variant myeloma cells" *Science* 167:186–188 (1970).

Coffino et al., "Suppression of Immunoglobulin Synthesis by Cellular Hybridization" *Nature New Biology* 231:87–90 (May 19, 1971).

Cook and Scharff, "Antigen–binding mutants of mouse myeloma cells" *Proc. Natl. Acad. Sci. USA* 7(12):5687–5691 (1977).

Cook et al., "Somatic mutation in a cultured mouse myeloma cell affects antigen binding" *Proc. Natl. Acad. Sci. USA* 79:1240–1244 (1982).

Cotton and Milstein, "Fusion of two immunoglobulin–producing myeloma cells" *Nature* 244:42–43 (Jul. 6, 1973).

Crews et al., "A Single VH Gene Segment Encodes the Immune Response to Phosphorylcholine: Somatic Mutation Is Correlated with the Class of the Antibody" *Cell* 25:59–66 (1981).

Croce et al., "Production of human hybridomas secreting antibodies to measles virus" *Nature* 288:488–489 (1980).

Dangl et al., "Segmental flexibility and complement fixation of genetically engineered chimeric human, rabbit and mouse antibodies" *The EMBO Journal* 7(7):1989–1994 (1988).

Dangl, "Rapid isolation of cloned isotype switch variants using fluorescence activated cell sorting" *Cytometry* 2(6):395–401 (1982).

De Bernardez–Clark and Georgiou, "Inclusion bodies and recovery of proteins from the aggregated state" *Protein Refolding* Chapter 1:1–20 (1991).

De Boer et al., "Construction of a Tandem trp–lac Promoter and a Hybrid trp–lac Promoter for Efficient and Controlled Expression of the Human Growth hormone Gene in *Escherichia coli*" *Promoters, Structure and Function* (Praeger Publishers, R. Rodriguez and M. Chamberline, eds.) pp. 462–481 (1982).

Dildrop et al., "Immunoglobulin V region variants in hybridoma cells. II. Recombination between V genes" *EMBO Journal* 1(5):635–640 (1982).

Dover, Gabby, "Nonhomologous Views of a Terminology Muddle" *Cell* 51:515–516 (Nov. 20, 1987).

Duyvesteyn and De Waard, "A new sequence–specific endonuclease from a thermophilic cyanobacterium, mastigocladus laminosus" *FEBS Letters* 111(2):423–426 (1980).

Duyvesteyn et al., "Sequence–specific endonucleases in strains of anabaena and nostoc" *Arch. Microbiol.* 134:276–281 (1983).

Early and Hood, "Mouse immunoglobulin genes" *Genetic Engineering, Principles and Methods*, Setlow and Hollaender, N.Y. and London, UK:Plenum Press vol. 3:157–188 (1981).

Early et al., "Allelic Exclusion and Nonproductive Immunoglobulin Gene Rearrangements" *Cell* 24:1–3 (Apr. 1981).

Early et al., "An immunoglobulin heavy chain variable region gene is generated from three segments of DNA: $V_H$ D and $J_H$" *Cell* 19:981–992 (1980).

Edelman, G., "Antibody structure and molecular immunology" *Annals of the New York Academy of Sciences* 190:5–25 (1971).

Edwards et al., "A human–human hybridoma system based on a fast–growing mutant of the ARH–77 plasma cell leukemia–derived line" *European J. Immunol.* 12:641–648 (1982).

Ellison et al., "Linkage and sequence homology of two human immunoglobulin gamma heavy chain constant region genes" *Proc. Natl. Acad. Sci. USA* 79:1984–1988 (Mar. 1982).

Ellison et al., "Nucleotide sequence of a human immunoglobulin $C_{\gamma 4}$ gene" *DNA* 1(1):11–18 (1981).

Ellison et al., "The nucleotide sequence of a human immunoglobulin $C_{\gamma 1}$ gene" *Nucleic Acids Research* 10(13):4071–4079 (1982).

Eshhar et al., "Induction of secretion of IgM from cells of the B cell line 38C–13 by somatic cell hybridization" *J. Immunol.* 122(6):2430–2434 (1979).

Feiss et al., "Separate sites for binding and nicking of bacteriophage λ DNA by terminase" *Proc. Natl. Acad. Sci. USA* 80:955–959 (1983).

Fiers et al., "Complete Nucleotide Sequence of SV40 DNA" *Nature* 273:113–120 (May 11, 1978).

Gillies et al., "A tissue–specific transcription enhancer element is located in the major intron of a rearranged immunoglobulin heavy chain gene" *Cell* 33:717–728 (1983).

Gillies et al., "Antigen Binding and Biological Activities of Engineered Mutant Chimeric Antibodies with Human Tumor Specificities" *Hum. Antibod. Hybridomas* 1(1):47–54 (1990).

Givol et al., "Diversity of germ–line immunoglobulin $V_H$ genes" *Nature* 292:426–430 (1981).

Gluzman, Yakov, "SV40–Transformed Simian Cells Support the Replication of Early SV40 Mutants" *Cell* 23:175–182 (Jan. 1981).

Goldsby et al., "Hybrid cell lines with T–cell characteristics" *Nature* 267:707–708 (Jun. 23, 1977).

Graham and van der Eb, "A New Technique for the Assay of Infectivity of Human Adenovirus 5 DNA" *Virology* 52:456–467 (1973).

Gritz and Davies, "Plasmid–encoded hygromycin B resistance: the sequence of hygromycin B phosphotransferase gene and its expression in *Escherichia coli* and *Saccharomyces cerevisiae*" *Gene* 25:179–188 (1983).

Gupta et al., "General Orientation of Human Lymphocyte Subpopulations" *Clinical Immunobiol.*, Bach and Good, Academic Press vol. 4:1–18 (1980).

Hedin et al., "Specificities and Binding Properties of Eight Monoclonal Antibodies Against Carcinoembryonic Antigen" *Molecular Immunology* 19:1641–1648 (1982).

Herlyn et al., "Inhibition of Growth of Colorectal Carcinoma in Nude Mice by Monoclonal Antibody" *Cancer Research* 40:717–721 (Mar. 1980).

Herzenberg et al., "Hybridoma Variants Affecting Isotype, Antigen Binding, and Idiotype" *Biotechnology in Diagnostics*, Koprowski et al. vol. 21:3–16 (1985).

Hieter et al., "Cloned human and mouse kappa immunoglobulin constant and J region genes conserve homology in functional segments" *Cell* 22(Part 1):197–207 (1980).

Honjo et al., "Cloning and complete nucleotide sequence of mouse immunoglobulin γ1 Chain Gene" *Cell* 18:559–568 (1979).

Honjo et al., "Rearrangements of Immunoglobulin Genes during Differentiation and Evolution" *Immunological Rev.* 59:33–67 (1981).

Hood et al., "Antibodies" *Immunology*, Forkner and Moore, Philippines:The Benjamin/Cummings Publishing Co., Inc., Chapter 3, pp. 199–221 (1978).

Horwitz et al., "Secretion of functional antibody and Fab fragment from yeast cells" *Proc. Natl. Acad. Sci. USA* 85:8678–8682 (1988).

Houghton et al., "Detection of cell surface and intracellular antigens by human monoclonal antibodies" *Journal of Experimental Medicine* 158:53–65 (1983).

Howard et al., "A Rapid Method for the Detection of Antibodies to Cell Surface Antigens: A Solid Phase Radioimmunoassay Using Cell Membranes" *Journal of Immunological Methods* 38:75–84 (1980).

Howard et al., "Long–term culture of normal mouse B lymphocytes" *Proc. Natl. Acad. Sci. USA* 78(9):5788–5792 (Sep. 1981).

Hughes and Murray, "The nucleotide sequences recognized by endonucleases AvaI and AvaII from *Anabaena variabilis*" *Biochemical Journal* 185:65–75 (1980).

Hunkapiller et al., "The growing immunoglobulin gene superfamily" *Nature* 323:15–16 (1986).

"Immunoglobulin molecules and genes" *Microbiology Including Immunology and Molecular Genetics*, Third edition, Harper International Edition vol. Chapter 17:338–379.

Inouye et al., "Signal Sequence of Alkaline Phosphatase of *Escherichia coli*" *J. Bacteriol.* 149:434 (1982).

Isenman et al., "The structure and function of immunoglobulin domains" *J. Immunol.* 114(6):1726–1929 (1975).

Itakura and Riggs, "Chemical DNA synthesis and recombinant DNA studies" *Science* 209:1401–1405 (1980).

Jaton et al., "Conformational changes induced in a homogeneous anti–type III pneumococcal antibody by oligosaccharides of increasing size" *Biochemistry* 14(24):5312–5315 (1975).

Johnson et al., "The Complete V Domain Amino Acid Sequences of Two Myeloma Inulin–Binding Proteins" *Journal of Immunology* 128:302–307 (1982).

Jones, P.T. et al., "Replacing the Complementarity–determining Regions in a Human Antibody with Those From a Mouse" *Nature* 321:522–525 (May 29, 1986).

Kabat, E., "Activation of the complement system and its effect on cells" *Structural Concepts in Immunology and Immunochemistry*, Second edition, Holt, Rinehart and Winston vol. Chapter 13:413–435 (1976).

Kaivarainen et al., "Hapten–induced changes in pig anti––Dansyl antibodies revealed by EPR spectra of spin–labelled antibodies" *Immunol. Letters* 3:5–11 (1981).

Kalderon et al., "Deletion loop mutagenesis: a novel method for the construction of point mutations using deletion mutants" *Nucl. Acids Res.* 10:5161–5168 (1982).

Keshet et al, "Cloning of bovine growth hormone gene and its expression in bacteria" *Nucleic Acids Research* 9:19–30 (1981).

Kipps et al., "Allotype Switch Variants in Cultured Monoclonal Producing Hybridomas" *Journal of Cellular Biochemistry* (abstract only) pp. 163 (–1984).

Kitai et al., "Extracellular production of human immunoglobulin G FC region" *Microbiol. Biotechnol.* 28(1):52–56 (1988).

Klein et al., "Expression of biological effector functions by immunoglobulin G molecules lacking the hinge region" *Proc. Natl. Acad. Sci. USA* 78(1):524–528 (1981).

Kohl and Moore, "Human antibody–dependent cellular cytotoxicity and natural killer cytotoxicity to herpes simplex virus–infected autologous and allogeneic cells" *Immunology* 48:187–193 (1983).

Kohler et al., "Derivation of Specific Antibody–producing Tissue Culture and Tumor Lines by Cell Fusion" *European Journal of Immunology* 6:511–519 (1976).

Kohler, G. and Milstein, C., "Continuous Cultures of Fused Cells Secreting Antibody of Predefined Specificity" *Nature* 256:495–497 (Aug. 7, 1975).

Konieczny et al., "The combination of IgM subunits and proteolytic IgG fragments by controlled formation of interchain disulphides" *Haematologia* 14(1):95–99 (1981).

Koskimies, S., "Human lymphoblastoid cell line producing specific antibody against Rh–antigen D" *Scand. J. Immunol.* 11:73–77 (1980).

Kuehl, W.M., "Light chain fragments: aberrant expression of immunoglobulin genes" *TIBS* pp. 206–208 (Aug. 1981).

Kupchik et al., "Monoclonal Antibodies to Carcinoembryonic Antigen Produced by Somatic Cell Fusion" *Cancer Research* 41:3306–3310 (Sep. 1981).

Kwan, "Two Kappa Immunoglobulin Genes Are Expressed in the Myeloma S107" *Cell* 26:57–66 (Oct. 1981).

Larson et al., "*Saccharomyces cerevisiae* actin–*Escherichia coli* lacZ gene fusions: synthetic–oligonucleotide–mediated deletion of the 309 base pair intervening sequence in the actin gene" *Gene* 22:31–39 (1983).

Laskov and Scharff, "Synthesis, assembly, and secretion of gamma globulin by mouse myeloma cells" *Journal of Experimental Medicine* 131(3):515–541 (1970).

Laskov et al., "Induction of amplified synthesis and secretion of IgM by fusion of murine B Lymphoma with myeloma cells" *Proc. Natl. Acad. Sci. USA* 76(2):915–919 (Feb. 1979).

Lau and Doolittle, "Aqu I: a more easily purified isoschizomer of AVA I" *FEBS Letters* 121(2):200–202 (1980).

Leder, P., "The genetics of antibody diversity" *Scientific America* 246:72–83 (1982).

Lee et al., "Characterization of the Gene Encoding Heat–Stable Toxin II and Preliminary Molecule Epidemiological Studies of Enterotoxigenic *Escherichia coli* Heat–Stable Toxin II Producers" *Infection and Immunity* 42:264–268 (Oct. 1983).

Letherbarrow et al., "Effector functions of a monoclonal aglycosylated mouse IgGza:binding and activation of complement component C1 and interaction with human monocyte Fc receptor" *Molec. Immunol.* 22(4):407–415 (1985).

Levy and Miller, "Tumor therapy with monoclonal antibodies" *Fed. Proc.* 42:2650–2656 (1983).

Lewin, Roger, "When Does Homology Mean Something Else?" *Science* 237:1570 (1987).

Liu et al., "Chimeric mouse–human IgG1 antibody that can mediate lysis of cancer cells" *Proc. Natl. Acad. Sci. USA* 84:3439–3443 (May 1987).

Liu, Pinghui V., "Pseudomonas Toxins" *J. Infect. Dis.* 130:S94–S99 (1974).

Maniatis et al. *Molecular Cloning: A Laboratory Manual*, 1st edition, New York:Cold Spring Harbor Lab Press, Chapter 12, pps. selected pages (1982).

Maniatis, T., "Recombinant DNA procedures in the study of eukaryotic genes" *Cell Biol.* 3:563–608 (1980).

Margulies et al., "Regulation of immunoglobulin expression in mouse myeloma cells" *Immunoglobulin Expression* pp. 781–791 (1977).

Margulies et al., "Somatic Cell Hybridization of Mouse Myeloma" *Cell* 8:405–415 (Jul. 1976).

Martinis et al., "Monoclonal antibodies with dual antigen specificity" *Oncology* pp. 311–316.

Mather et al., "Transcriptional regulation of immunoglobulin V genes" *Nucleic Acids Research* 9(24):6855–6867 (1981).

Matsuuchi and Morrison, "Antigen binding variants of mouse plasmacytoma J558" *Fed. Proc.* (Abstract only) 37:1763 (2703) (1978).

Max et al., "Variation in the Crossover Point of Kappa Immunoglobulin Gene V–J Recombination: Evidence from a Cryptic Gene" *Cell* 21:793–799 (Oct. 1980).

McCutchan et al., "Enhancement of the Infectivity of Simian Virus 40 Deoxyribonucleic Acid with Diethylaminoethyl–Dextran" *J. Natl. Cancer Institute* 41:351–356 (1968).

Melchers, F., "Biosynthesis of the carbohydrate portion of immunoglobulin radiochemical and chemical analysis of the carbohydrate moieties of two myeloma proteins purified from different subcellular fractions of plasma cells" *Biochemistry* 10(4):653–659 (1971).

Mertz et al., "Defective Simian Virus 40 Genomes: Isolation and Growth of Individual Clones" *Virology* 62:112–124 (1974).

Messing et al., "A System for Shotgun DNA Sequencing" *Nucleic Acids Research* 9(2):309–321 (1981).

Milstein et al., "Clonal Variants of Myeloma Cells" *Progress in Immunology II* 1:157–168 (1974).

Mohit and Fan, "Hybrid Cell Line from a Cloned Immunoglobulin–Producing Mouse Myeloma and a Nonproducing Mouse Lymphoma" *Science* 171:75–77 (Jan. 8, 1971).

Morrison and Scharff, "Mutational events in mouse myeloma cells" *Critical Reviews in Immunology* 3(1):1–22 (1981).

Morrison et al., "Chimeric Human Antibody Molecules: Mouse Antigen–binding Domains with Human Constant Region Domains" *Proc. Natl. Acad. Sci. USA* 81:6851–6855 (Nov. 1984).

Morrison et al., "Genetically Engineered Antibody Molecules" *Adv. Immunol.* 44:65–92 (1989).

Morrison et al., "Transfectomas Provide Antibodies With Novel Structures and Functions" *Antibodies: Structure, Synthesis, Function, and Immunologic Intervention in Disease*, Szentivanyi et al. pp. 167–178 (1987).

Morrison et al., "Transfer and expression of immunoglobulin genes" *Annual Review of Immunology* 2:239–256 (1984).

Morrison, S. L., "Transfectomas Provide Novel Chimeric Antibodies" *Science* 229:1202–1207 (Sep. 20, 1985).

Movva et al., "Amino Acid Sequence of the Signal Peptide of ompA Protein, a Major Outer Membrane Protein of *Escherichia coli*" *The Journal of Biological Chemistry* 255:27–29 (Jan. 10, 1980).

Nakabayashi et al., "The transforming function of bovine papillomavirus DNA" *Proc. Natl. Acad. Sci. USA* 80:5832–5836 (1983).

Neuberger et al., "A hapten–specific chimaeric IgE antibody with human physiological effector function" *Nature* 314:268–270 (Mar. 21, 1985).

Neuberger et al., "Recombinant Antibodies Possessing Novel Effector Functions" *Nature* 312:604–608 (Dec. 13, 1984).

Neuberger, "Switch from hapten–specific immunoglobulin M to immunoglobulin D secretion in a hybrid mouse cell line" *Proc. Natl. Acad. Sci. USA* 78(2):1138–1142 (1981).

Ochi et al., "Functional immunoglobulin M production after transfection of cloned immunoglobulin heavy and light chain genes into lymphoid cells" *Proc. Natl. Acad. Sci. USA* 80:6351–6355 (1983).

Oi et al., "Correlation between segmental flexibility and effector function of antibodies" *Nature* 307:136–140 (1984).

Oi et al., "Hybridoma Antibody–Producing Switch Variants: A Variant Lacking the CH1 Domain" *Cell Fusion: Gene Transfer and Transformation*, R.F. Beers, Jr. and E.G. Bassett, Raven Press, New York pp. 281–287 (1984).

Oi et al., "Localization of Murine Igh–1ᵃ Allotypic Determinants by Using a Panel of Mouse Myeloma Variant Immunoglobulins" *Journal of Immunology* 130(4):1967–1969 (Apr. 1983).

Oi et al., "Lymphocyte membrane IgG and secreted IgG are structurally and allotypically distinct" *Journal of Experimental Medicine* 151:1260–1274 (1980).

Olsson and Kaplan, "Human–human hybridomas producing monoclonal antibodies of predefined antigenic specificity" *Proc. Natl. Acad. Sci. USA* 77(9):5429–5431 (1980).

Orna Zemel–Dreasen et al., "Secretion and processing of an immunoglobulin light chain in *Escherichia coli*" *Gene* 27(3):315–322 (1984).

Owens and Young, "The genetic engineering of monoclonal antibodies" *J. Immunol. Methods* 168:149–165 (1994).

Palva et al., "Secretion of interferon by *bacillus subtilis*" *Gene* 22:229–235 (1983).

Parham et al., "Isolation of Heavy Chain Class Switch Variants of a Monoclonal Anti–DC1 Hybridoma Cell Line: Effective Conversion of Noncytotoxic $IgG_1$ Antibodies to Cytotoxic $IgG_2$ Antibodies" *Human Immunology* 8:141–151 (1983).

Peden and Nathans, "Local mutagenesis within deletion loops of DNA heteroduplexes" *Proc. Natl. Acad. Sci. USA* 79:7214–7217 (1982).

Periman, "IgG Synthesis in Hybrid Cells from an Antibody–producing Mouse Myeloma and an L Cell Substrain" *Nature* 228:1086–1087 (Dec. 12, 1970).

Perry et al., "Transcription of mouse κ chain genes: implications for allelic exclusion" *Proc. Natl. Acad. Sci. USA* 77(4):1937–1941 (1980).

Picken et al., "Nucleotide sequence of the gene for heat–stable enterotoxin II of *Escherichia coli*" *Infection and Immunity* 42(1):269–275 (1983).

Plaut et al., "Immunoglobulin M: Fixation of human complement by the Fc Fragment" *Science* 176:55–56 (1972).

Ponte et al., "Transcription of immunoglobulin heavy–chain sequences from the excluded allele" *Nature* 291:594–596 (1981).

Raghunathan et al., "Abstract P–D2–01–Influence of variable domain glycosylation on antigen binding:crystal structure of anti–GnRH Fab frament" *Prog. Biophy & Mol. Biol.* 65(5):143–(1996).

Raschke et al., "Assembly and secretion of pentameric IgM in a fusion between a nonsecreting B cell lymphoma and an IgG–secreting plasmacytoma" *Proc. Natl. Acad. Sci. USA* 76(7):3469–3473 (1979).

Rechavi et al., "Evolutionary aspects of immunoglobulin heavy chain variable region ($V_H$ gene subgroups" *Proc. Natl. Acad. Sci. USA* 80:855–859 (1983).

Reeck et al., "'Homology' in Proteins and Nucleic Acids: A Terminology Muddle and a Way out of it" *Cell* 50 (Aug. 28, 1987).

Reth et al., "Analysis of the repertoire of anti–NP antibodies in C57BL/6 mice by cell fusion" *European Journal of Immunology* 8:393–400 (1978).

Rice et al, "Measurement of transient cDNA expression in mammalian cells using flow cytometric cell analysis and sorting" *Cytometry* 12:221–233 (1991).

Riley et al., "Induction of light chain expression in a pre–B cell line by fusion to myeloma cells" *Nature* 289:804–806 (1981).

Robins et al., "Regulated Expression of Human Growth Hormone Genes in Mouse Cells" *Cell* 29:623–631 (1982).

Roizes, "A new specific endonuclease from *Anabaena variabilis*" *FEBS Letters* 104(1):39–44 (1979).

Rouger and Goossens, "Human Monoclonal antibodies against human red blood cells" *Therapeutic Monoclonal Antibodies*, Borrebaeck and Larrick, M Stockton Press pp. 263–286 (1990).

Rybarska et al., "The Hemolytic Activity of (Fab–Fc) Recombinant Immunoglobulins with Specificity for the Sheep Red Blood Cells" *Immunology Letters* 4:279–284 (1982).

Sakano et al., "Domains and the hinge region of an immunoglobulin heavy chain are encoded in separate DNA segments" *Nature* 277:627–633 (1979).

Scharff et al., "Variations in the synthesis and assembly of immunoglobulins by mouse myeloma cells: A Genetic and Biochemical Analysis" *J. Cellular Physiology* 76:331–348 (1970).

Scholm et al., "Generation of human monoclonal antibodies reactive with human mammary carcinoma cells" *Proc. Natl. Acad. Sci. USA* 77(11):6841–6845 (1980).

Schroder et al., "Florescence–activated cell sorting of mouse–human hybrid cells aids in locating the gene for the Leu 7 (HNK–1) antigen to human chromosome 11" *Proc. Natl. Acad. Sci. USA* 80:3421–3424 (Jun. 1983).

Schwaber and Cohen, "Human x mouse somatic cell hybrid clone secreting immunoglobulins of both parental types" *Nature* 244:444–447 (1973).

Schwaber and Cohen, "Pattern of Immunoglobulin synthesis and assembly in a human–mouse somatic cell hybrid clone" *Proc. natl. Acad. Sci. USa* 71(6):2203–2207 (1974).

Schwaber, J., "Immunoglobulin production by a human–mouse somatic cell hybrid" *Experimental Cell Research* 93:343–354 (1975).

Schwartz et al., "Multiple expression of Ig λ–chain encoding RNA species in murine plasmacytoma cells" *J. Immunol.* 126(6):2104–2108 (1981).

Sears et al., "Phase–I clinical trial of monoclonal antibody in treatment of gastrointestinal tumours" *Lancet* pp. 762–765 (1982).

Secher et al., "Somatic mutants and antibody diversity" *Immunological Rev.* 36:51–72 (1977).

Seidman and Leder, "A mutant immunoglobulin light chain is formed by aberrant DNA–and RNA–splicing events" *Nature* 286:779–783 (1980).

Seidman and Leder, "The arrangement and rearrangement of antibody genes" *Nature* 276:790–795 (1978).

Seidman et al., "a κ–immunoglobulin gene is formed by site–specific recombination without further somatic mutation" *Nature* 280:370–375 (1979).

Seidman et al., "Multiple related immunoglobulin variable–region genes identified by cloning and sequence analysis" *Proc. Natl. Acad. Sci. USa* 75(8):3881–3885 (1978).

Sharon et al., "Expression of a $V_H C_\kappa$ chimaeric protein in mouse myeloma cells" *Nature* 309:364–367 (1984).

Shine et al., "Expression of cloned β–endorphin gene sequences by *Escherichia coli*" *Nature* 285:456–461 (1980).

Shulman *9th Annual Meeting of the Clinical Ligand Assay Society* (*Declaration of Marc J. Shulman dated May 21, 1994 with Exhibits A–E*) (Alleged oral presentation Mar. 13–17, 1983, Philadelphia, Pennsylvania) (1983).

Shulman and Kohler, "Fusion of Immunoglobulin Secreting Cells" *Cells of Immunoglobulin Synthesis*, Pernis and Vogel, Academic Press pp. 275–293 (1979).

Siddiqui, M., "Recombinant DNA technology and its application to developmental biology" *J. Craniofacial Genetics and Developmental Biology* 2:75–92 (1982).

Skerra et al., "Secretion and in vivo folding of the Fab fragment of the antibody McPC603 in *Escherichia coli*: influence of disulphides and cis prolines" *Protein Engineering* 4(8):971–979 (1991).

Sninsky et al., "Construction and characterization of a novel two–plasmid system for accomplishing temperature–regulated, amplified expression of cloned adventitious genes in *Escherichia coli*" *Gene* 16:275–286 (1981).

Sogn, J., "Interspecific Hybridomas" *Methods of Hybridoma Formation*, Bartal and Hirshaut, Clifton, New Jersey: Humana Press pp. 317–331 (1987).

Sonenshein et al., "Control of immunoglobulin secretion in the murine plasmacytoma line MOPC 315" *Journal of Experimental Medicine* 148:301–312 (1978).

Stark et al., "Site–directed mutagenesis of ribosomal RNA" *J. Mol. Biol.* 159:417–439 (1982).

Steinmetz et al., "Cloning of V region fragments from mouse liver DNA and localization of repetitive DNA sequences in the vicinity of immunoglobulin gene segments" *Nucleic Acids Research* 8:1709–1720 (1980).

Strominger et al., "An Evaluation of the Significance of Amino Acid Sequence Homologies in Human Histocompatibility Antigens (HLA–A and HLA–B) with Immunoglobulins and Other Proteins, Using Relatively Short Sequences" *Scand. J. Immunol.* 11:573–592 (1980).

Takahashi et al., "Structure of Human Immunoglobulin Gamma Genes: Implications for Evolution of a Gene Family" *Cell* 29:671–679 (1982).

Tanaka et al., "Isolation and characterization of polyoma virus mutants which grow in murine embryonal carcinoma and trophoblast cells" *EMBO Journal* 1(12):1521–1527 (1982).

Tao et al., "Studies of aglycosylated chimeric mouse–human IgG. Role of Carbohydrate in the Structure and Effector Functions Mediated by the Human IgG Constant Region" *Journal of Immunology* 143(8):2595–2601 (Oct. 15, 1989).

Taylor et al., "Selective removal of a heavy–chain glycosylation sites causes immunoglobulin A degradation and reduced secretion" *Molecular & Cellular Biology* 8(10):4197–4203 (1988).

Teng et al., "Construction and testing of mouse–human heteromyelomas for human monoclonal antibody production" *Proc. Natl. Acad. Sci. USA* 80:7308–7312 (1983).

Tonegawa et al., "Cloning of an immunoglobulin variable region gene from mouse embryo" *Proc. Natl. Acad. Sci. USA* 74(8):3518–3522 (1977).

Tonegawa et al., "Sequence of a mouse germ–line gene for a variable region of an immunoglobulin light chain" *Proc. Natl. Acad. Sci. USa* 75(3):1485–1489 (1978).

Tucker et al., "Structure of the constant and 3' untranslated regions of the murine $\gamma 2b$ heavy chain messenger RNA" *Science* 206:1299–1303 (1979).

Uhlen et al., "Gene fusion vectors based on the gene for staphylococcal protein A" *Gene* 23:369–378 (1983).

Underbrink–Lyon et al., "Characterization of a yeast mitochondrial locus necessary for tRNA biosynthesis" *Mol. Gen. Genet.* 191:512–518 (1983).

Uracz et al., "The use of Fab–Fc recombinant antibodies for studying the mechanism of triggering the effector activities of immunoglobulins" *Immunology Letters* 7:215–220 (1984).

van Loghem, E., "Genetic studies on human immunoglobulins" *Handbook of Experimental Immunology*, D.M. Weir, Third Ed. edition, Blackwell Scientific Publications vol. 1:11.1–11.16 (1978).

Wagener et al., "Monoclonal antibodies for carcinoembryonic antigen and related antigens as a model system: a systematic approach for the determination of epitope specificities of monoclonal antibodies" *J. Immunol.* 130(5):2308–2315 (1983).

Wall, R. and Kuehl, M., "Biosynthesis and regulation of immunoglobulins" *Annual Review of Immunology* 1:393–422 (1983).

Wallace et al., "Directed deletion of a yeast transfer RNA intervening sequence" *Science* 209:1396–1400 (1980).

Wallach et al., "Analysis of immunoglobulin mRNA in murine myeloma cell variants defective in the synthesis of the light or heavy polypeptide chains" *J. Immunol.* 128(2):684–689 (1982).

Watson et al., "In vitro growth of B lymphocytes infiltrating human melanoma tissue by transformation with EBV: evidence for secretion of anti–melanoma antibodies by some transformed cells" *J. Immunol.* 130(5):2442–2447 (1983).

Watson, Marion E.E., "Compilation of published signal sequences" *Nucleic Acids Research* 12:5145–5164 (1984).

Weatherall and Clegg, "Recent developments in the molecular genetics of human hemoglobin" *Cell* 16:467–479 (1979).

Weck et al., "Antiviral activities of hybrids of two major human leukocyte interferons" *Nucleic Acids Research* 9(22):6153–6166 (1981).

Weiss and Green, "Human–mouse hybrid cell lines containing partial complements of human chromosomes and functioning human genes" *Proc. Natl. Assoc. Sci. USA* 58:1104–1111 (1967).

Wetzel, R., "Active immunoglobulin fragments synthesized in *E. coli*—from Fab to Scantibodies" *Protein Engineering* 2(3):169–170 (1988).

Whitlock and Witte, "Long–term culture of B lymphocytes and their precursors from murine bone marrow" *Proc. Natl. Acad. Sci. USA* 79:3608–3612 (1982).

Wigler et al., "Transformation of Mammalian Cells with Genes from Procaryotes and Eucaryotes" *Cell* 16:777–785 (Apr. 1979).

Winberry et al., "Immunoglobulin production and secretion by variant clones of the MOPC 315 mouse myeloma cell line" *J. Immunol.* 124(3):1174–1182 (1980).

Winkelhake et al., "Effects of pH treatments and deglycosylation of rabbit immunoglobulin G on the binding of C1q" *Journal of Biological Chemistry* 255(7):2822–2828 (Apr. 10, 1980).

Wood et al., "The synthesis and in vivo assembly of functional antibodies in yeast" *Nature* 314:446–449 (1985).

Word et al., "Expression of surface and secreted $IgG_{2a}$ by a murine B–lymphoma before and after hybridization to myeloma cells" *Molecular Immunology* 18(4):311–322 (1981).

Wright et al., "Antibody variable region glycosylation: position effects on antigen binding and carbohydrate structure" *EMBO Journal* 10(10):2717–2723 (1991).

Yamawaki–Kataoka et al., "Nucleotide sequences of gene segments encoding membrane domains of immunoglobulin γ chains" *Proc. Natl. Acad. Sci. USA* 79:2623–2627 (1982).

Yamawaki–Kataoka et al., "The complete nucleotide sequence of mouse immunoglobulin γ2a gene and evolution of heavy chain genes: further evidence for intervening sequence–mediated domain transfer" *Nucleic Acids Research* 9(6):1365–1381 (1981).

Yamawaki–Kataoka, "Complete nucleotide sequence of immunoglobulin γ2b chain gene cloned from newborn mouse DNA" *Nature* 283:786–789 (1980).

Zakut et al., "Cloning and sequence of the cDNA corresponding to the variable region of immunoglobulin heavy chain MPC11" *Nucleic Acids Research* 8(16):3591–3601 (1980).

Zav'yalov et al., "Correspondence between structure and function of immunoglobulin G subclasses" *Haematologia* 14(1):85–94 (1981).

Fig. 2A.

```
                                             sau3A                                fnu4HI
                                             dpnI                                 bbv             mnlI  hincII                       aluI
       hgaI                                  bclI                                 aluI            sau96  hgaI
501    GCGTCCTGAA CAGTTGGACT GATCAGGACA GCAAAGACAG CACCTACAGC ATGAGCAGCA CCCTCACGTT GACCAAGGAC GAGTATGAAC GACATAACAG
       CGCAGGACTT GTCAACCTGA CTAGTCCTGT CGTTTCTGTC GTGGATGTCG TACTCGTCGT GGGAGTGCAA CTGGTTCCTG CTCATACTTG CTGTATTGTC mnlI                                            hphI                                        ddeI  acyI
             haeIII                                          aluI                                 avaII
             haeI                                                                                        aluI
601    CTATACCTGT GAGGCCACTC ACAAGACATC AACTTCACCC ATTGTCAAGA GCTTCAACAG GAATGAGTGT TAGAGACAAA GGTCCTGAGA CGCCACCACC
       GATATGGACA CTCCGGTGAG TGTTCTGTAG TTGAAGTGGG TAACAGTTCT CGAAGTTGTC CTTACTCACA ATCTCTGTTT CCAGGACTCT GCGGTGGTGG aluI       aluI           mboII  ddeI                      mnlI                                         mnlI
701    AGCTCCCCAG CTCCATCCTA TCTTCCCTTG GAGGCTTCCC CACAAGCGAC CTACCACTGT TGCGGTGCTC CAAACCCTCC CCCACCTCCT
       TCGAGGGGTC GAGGTAGGAT AGAAGGGAAC CTCCGAAGGG GTGTTCGCTG GATGGTGACA ACGCCACGAG GTTTGGGAGG GGGTGGAGG
                        fokI                                                               hgiA       mnlI
                  mnlI  mnlI                                    xmnI                              hinfI
801    TTCTCCTCCT CCTCCCTTTC CTTGGCTTTT ATCATGCTAA TATTTGCAGA AAATATTCAA TAAAGTGAGT CTTTGCACTT GA
       AAGAGGAGGA GGAGGGAAAG GAACCGAAAA TAGTACGATT ATAAACGTCT TTTATAAGTT ATTTCACTCA GAAACGTGAA CT
``` nucleotides: 882

Fig. 2B.

```
        -9                    1
        leu trp leu ser gly val glu gly asp ile val met thr gln ser his lys phe met ser thr ser val gly asp arg val ser
     G  UUG CUG UGG UCU GGU GUU GAA GGA GAC AUU GUG AUG ACC CAG UCU CAC AAA UUC AUG UCC ACA UCA GUA GGA GAC AGG GUC AGC
                          10                              20
        ile thr cys lys ala ser gln asp val gly thr ala ile thr tyr gln ser pro lys leu ile tyr trp
        AUC ACC UGC AAG GCC AGU CAG GAU GUG GGU ACU GCU AUA GCC UGG UAU CAA UCU CCU AAA CUA CUG AUU UAC UGG
              30                              40                              50
        ala ser thr arg his thr gly val pro phe arg asp ser gly ser gly thr asp phe thr leu thr ile ser asn val gln ser
        GCA UCC ACC CGG CAC ACU GGA GUC CCU GAU CGC UUC ACA GGC AGU GGA UCU GGG ACA GAU UUC ACU CUC ACC AUU AGC AAU GUG CAG UCU
                          60                              70                              80
        asp asp leu ala asp tyr phe cys gln gln tyr ser tyr pro leu thr phe gly gly gly thr lys leu glu leu lys arg ala asp
        GAU GAC UUG GCA GAU UAU UUC UGU CAA CAA UAU AGU UAU CCU CUC ACG UUC GGU GGG GGG ACC AAG CUG GAG CUG AAA CGG GCU GAU
              90                              100                             110
        ala ala pro thr val ser ile phe pro pro ser ser glu gln leu thr ser gly gly ala ser val val cys phe leu asn asn phe tyr
        GCA GCA CCA ACU GUA UCC AUC UUC CCA CCA UCC AGU GAG CAG UUA ACA UCU GGA GGU GCC UCA GUC GUG UGC UUC UUG AAC AAC UUC UAC
                          120                             130                             140
        pro lys asp ile asn val lys trp lys ile asp gly ser glu arg gln asn gly val leu asn ser trp thr asp gln asp ser lys asp
        CCC AAA GAC AUC AAU GUC AAG UGG AAG AUU GAU GGC AGU GAA CGA CAA AAU GGC GUC CUG AAC AGU UGG ACU GAU CAG GAC AGC AAA GAC
              150                             160                             170
        ser thr tyr ser met ser ser thr leu thr leu thr lys asp glu tyr glu arg his asn ser tyr thr cys glu ala thr his lys thr
        AGC ACC UAC AGC AUG AGC AGC ACC CUC ACG UUG ACC AAG GAC GAG UAU GAA CGA CAU AAC AGC UAU ACC UGU GAG GCC ACU CAC AAG ACA
                          180                             190                             200
        ser thr ser pro ile val lys ser phe asn arg asn glu cys AM
        UCA ACU UCA CCC AUU GUC AAG AGC UUC AAC AGG AAU GAA UGU UAG  AGACAAAGGUCCUGAGACGCCACCACCAGCUCCAUCCUAUCCUUCCUUCUAA
              210                             214
GGUCUGGAGGCUUCCCACAAGCGACUACCACCACUGUUGCGGUGCGGUGUGCUCCAAACCCUCCUUCUCUCCCUUCCUUGGCUUUUAUCAUGCUAAAUAUUGCUAAAUUGCAGAAAA

UAUUCAAUAAAGUGAGUCUUUGCACUUGA

Fig.3
```

```
                   sau96                              ddeI
            hinfI  avaII mnlI                         aluI                     ahaIII                        sfaNI
      hinfI GAGTCAGCAC TGAACACGGA CCCCTCACGA TGAACTTCGG GCTCAGCTTG ATTTACCTTG TCCTTGTTTT AAAAGTTGTC CAGTGTGAAG TGATGCTGGT
  1         CTCAGTCGTG ACTTGTGCCT GGGGAGTGCT ACTTGAAGCC CGAGTCGAAC TAAATGGAAC AGGAACAAAA TTTTCAACAG GTCACACTTC ACTACGACCA scrFI sau96
            hinfI  hinfI mnlI  avaII                            fnu4HI
            GGAGTCTGGG GGAGTCTTAA TGGAGCCTGG AGGGTCCCTG AAACTCTCCT GTGCAGCCTC TGGATTCACT TTCAGTAGAT ATGCCATGTC TTGGGTTCGC
101         CCTCAGACCC CCTCAGAATT ACCTCGGACC TCCCAGGGAC TTTGAGAGGA CACGTCGGAG ACCTAAGTGA AAGTCATCTA TACGGTACAG AACCCAAGCG hpaII                                                                                           hphI
            hinfI  mnlI                                                                                        hinfI
            CAGACTCCGG AGAAGAGGCT GGAGTGGGTC GCAACCATTA GTAGTGGTGG TAGTTCACAC CTTCCATCCA GACAGTGTGA AGGGCGATTC ACCATCTCCA
201         GTCTGAGGCC TCTTCTCCGA CCTCACCCAG CGTTGGTAAT CATCACCACC ATCAAGTGTG GAAGGTAGGT CTGTCACACT TCCCGCTAAG TGGTAGAGGT
                hinfI  mboII                                                    fokI rsaI                          mnlI                                                   mnlI
                                                            ddeI        mnlI   haeIII
            GAGACAATGC CAAGAACACC CTGTACCTGC AAATGAGCAG TCTGAGGTCT GAGGACACGG CCATGTATTA CTGTGCAAGA CCCCCTCTTA TTTCGTTAGT
301         CTCTGTTACG GTTCTTGTGG GACATGGACG TTTACTCGTC AGACTCCAGA CTCCTGTGCC GGTACATAAT GACACGTTCT GGGGGAGAAT AAAGCAATCA xhoII
                                                                                                                   scrFI
                                                           mnlI                                             sau96  sau3A
                                                           ddeI                                             haeIII ecoRII
                                                           mnlI hphI                                               dpnI
            AGCGGACTAT GCTATGGACT ACTGGGGTCA AGGAACCTCA GTCACCGTCT CCTCAGCCAA AACGACACCC CCATCTGTCT ATCCACTGGC CCCTGGATCT
401         TCGCCTGATA CGATACCTGA TGACCCCAGT TCCTTGGAGT CAGTGGCAGA GGAGTCGGTT TTGCTGTGGG GGTAGACAGA TAGGTGACCG GGGACCTAGA
```

Fig. 4A.

```
                                                                                                                         xhoII
                                                                                                                         sau3A
                                                                           scrFI                                         dpnI
                ncoI          scrFI                                ddeI    ecoRII                           scrFI        bamHI
fnu4HI          hphI  sfaNI   foKI                                 ecoRII  TCAAGGGCTA                       ecoRII       CTGTCCAGCG
bbv             bstEII ecoRII                                      TTTCCCTGAG CCAGTGACAG TGACCTGGAA CTCTGGATCC
GCTGCCCAAA CTAACTCCAT GGTGACCCTG GGATGCCTGG TCAAGGGCTA TTTCCCTGAG CCAGTGACAG TGACCTGGAA CTCTGGATCC CTGTCCAGCG
CGACGGGTTT GATTGAGGTA CCACTGGGAC CCTACGGACC AGTTCCCGAT AAAGGGACTC GGTCACTGTC ACTGGACCTT GAGACCTAGG GACAGGTCGC fnu4HI                                    sau96
      pvuII                                                 bbv  ddeI                                 mnlI
      alul          pstI                          mnlI      ddeI alul                                 haeIII              hphI
      GTGTGCACAC CTTCCCAGCT GTCCTGCAGT CTGACCTCTA CACTCTGAGC AGCTCAGTGA CTGTCCCCTC CAGCCCTCGG CCCAGCGAGA CCGTCACCTG
      CACACGTGTG GAAGGGTCGA CAGGACGTCA GACTGGAGAT GTGAGACTCG TCGAGTCACT GACAGGGGAG GTCGGGAGCC GGGTCGCTCT GGCAGTGGAC
      hgiA scrFI
      haeIII
      ncil hpaII     fnu4HI                                                             scrFI
      bgII hpaII     bbv                                                                ecoRII                ndeI rsaI
      CAACGTTGCC CACCCGGCCA GCAGCACCAA GGTGGACAAG AAAATTGTGC CCAGGGATTG TGGTTGTAAG CCTTGCATAT GTACAGTCCC AGAAGTATCA
      GTTGCAACGG GTGGGCCGGT CGTCGTGGTT CCACCTGTTC TTTTAACACG GGTCCCTAAC ACCAACATTC GGAACGTATA CATGTCAGGG TCTTCATAGT mstII                                                                  sau3A
                                         hphI   hinfI    ddeI                                                          dpnI mnlI
            mboII                        foKI hgiA       ddeI                                            accI          fokI aval
      mboII TCTGTCTTCA AAAGCCCAAG GATGTGCTCA CCATTACTCT GACTCCTAAG GTCACGTGTG TTGTGGTAGA CATCAGCAAG GATGATCCCG
      TCTGTCTTCA AAAGCCCAAG GATGTGCTCA CCATTACTCT GACTCCTAAG GTCACGTGTG TTGTGGTAGA CATCAGCAAG GATGATCCCG
      AGACAGAAGT TTTCGGGTTC CTACACGAGT GGTAATGAGA CTGAGGATTC CAGTGCACAC AACACCATCT GTAGTCGTTC CTACTAGGGC smaI
                                                          scrFI
                                                          scrFI
                                               mnlI       ncil
      sau96                                    hgiA       ncil
      avaII    pvuII                           alul hgaI  hpaII          mnlI                                          ddeI
      AGGTCCAGTT CAGCTGGTTT GTAGATGATG TGGAGGTGCA CACAGCTCAG ACGCAACCCC GGGAGGAGCA GTTCAACAGC ACTTTCCGCT CAGTCAGTGA
      TCCAGGTCAA GTCGACCAAA CATCTACTAC ACCTCCACGT GTGTCGAGTC TGCGTTGGGG CCCTCCTCGT CAAGTTGTCG TGAAAGGCGA GTCAGTCACT
```

*Fig. 4B.*

```
                  scrFI                                              fnu4HI
                  ecoRI                        hincII                 bbv                           taqI
        ACTTCCCATC ATGCACCAGG ACTGGCTCAA TGGCAAGGAG TTCAAATGCA GGGTCAACAG TGCAGCTTTC CCTGCCCCCA CATCTCCAAA TCGAGAAAAC
1001    TGAAGGGTAG TACGTGGTCC TGACCGAGTT ACCGTTCCTC AAGTTTACGT CCCAGTTGTC ACGTCGAAAG GGACGGGGGT GTAGAGGTTT AGCTCTTTTG haeIII
                           rsaI                        mnlI            haeI
        ACCAAAGGCA GACCGAAGGC TCCACACAGTG TACACCATTC CACCTCCCAA GGAGCAGATG GCCAAGGATA AGTCAGTCT GACCTGCATG ATAACAGACT
1101    TGGTTTCCGT CTGGCTTCCG AGGTGTCCAC ATGTGGTAAG GTGGAGGGTT CCTCGTCTAC CGGTTCCTAT TTCAGTCAGA CTGGACGTAC TATTGTCTGA mboII                                 fnu4HI                           ddeI
        mboII                                      bbv
        TCTTCCCTGA AGACATTACT GTGGAGTGGC AGTGGAATGG GCCCATCATG AACACGAATG GCTCTTACTT
1201    AGAAGGGACT TCTGTAATGA CACCTCACCG TCGGTTACC CGGGTAGTAC TTGTGCTTAC CGAGAATGAA mboII
            accI    aluI                                 mboII                              hphI                        ddeI
        CGTCTACAGC AAGCTCAATG TGCAGAAGAG CAACTGGGAG GCAGGAAATA CTTTCACCTG CTCTGTGTTA CATGAGGGCC TGCACAACCA CCATACTGAG
1301    GCAGATGTCG TTCGAGTTAC ACGTCTTCTC GTTGACCCTC CGTCCTTTAT GAAAGTGGAC GAGACACAAT GTACTCCCGG ACGTGTTGGT GGTATGACTC sau3A                    mnlI            sau96                         mnlI
              scrFI                   dpnI                        avaII             hinfI                       mnlI
        AAGAGCCTCT CCCACTCTCC TGGTAAATGA TCCCAGTGTC CTTGGAGCCC TCTGGTCCTA CAGGACTCTG ACACCTACCT CCACCCCTCC CTGTATAAAT
1401    TTCTCGGAGA GGGTGAGAGG ACCATTTACT AGGGTCACAG GAACCTCGGG AGACCAGGAT GTCCTGAGAC TGTGGATGGA GGTGGGGAGG GACATATTTA

AAAGCACCCA GCACTGCCTT GGGAAAAAA
1501    TTTCGTGGGT CGTGACGGAA CCCTTTTT
```

*Fig. 4C.*

```
GAGUCAGCACUGAACACGGACCCCUCACG
                                    met asn phe gly leu ser ile tyr leu val val leu lys val val gln cys glu
                                    AUG AAC UUC GGG CUC AGC AUU UAC CUU GUC GUU UUA AAA GUU CAG UGU GAA
                                                              -10                                          1
         10                                   20                                         30
val met leu val glu ser gly gly gly leu val gln pro gly gly ser leu lys leu ser cys ala
GUG AUG CUG GUG GAG UCU GGG GGA GGC UUA GUC CAG CCU GGA GGG UCC CUG AAA CUC UCC UGU GCA
                          40                                           50
tyr ala met ser trp val arg gln thr pro glu lys arg leu glu trp val ala thr ile ser ser his leu phe pro ser
UAU GCC AUG UCU UGG GUU CGC CAG ACU CCG GAG AAG AGG CUG GAG UGG GUC GCA ACC AUU AGU AGU CAC CUU UUC CCA UCC
          70                                          80
arg gln cys glu gly gly arg phe thr ile ser arg asp asn ala lys asn thr leu tyr leu gln met ser ser leu arg ser glu asp thr
AGA CAG UGU GAA GGG CGA UUC ACC AUC UCG AGA GAC AAU GCC AAG AAC ACC CUG UAC CUG CAA AUG AGC AGU CUG AGG UCU GAG GAC ACG
              100                                         110
ala met tyr tyr cys ala arg pro leu ile ser asp tyr ala met asp tyr trp gly gln gly thr ser val thr val cys leu
GCC AUG UAU UGU GCA AGA CCC CUU AUU UCG GAC UAU GCU AUG GAC UAU UGG GGU CAA GGA ACC UCU GUC ACC GUC UGC CUG
                                    130                                         140
ser ala lys thr thr pro pro ser val tyr pro leu ala pro gly ser ala ala gln thr asn ser met val thr leu gly cys leu
UCA GCC AAA ACG ACA CCC CCA UCU GUC UAU CCA CUG GCC CCU GGA UCU GCU GCC CAA ACU AAC UCC AUG GUG ACC CUG GGA UGC CUG
      160                                         170                                         180
val lys gly tyr phe pro glu pro val thr val thr trp asn ser gly ser leu ser ser gly val his thr phe pro ala val leu gln
GUC AAG GGU UAU UUC CCU GAG CCA GUG ACA GUG ACC UGG AAC UCU GGA UCC CUG UCC AGC GGU GUG CAC ACC UUC CCA GCU GUC CUG CAG
      190                                         200                                         210
ser asp leu tyr thr leu ser ser ser val thr val pro ser ser pro arg pro ser glu thr val thr cys asn val ala his pro ala
UCU GAC CUC UAC ACU CUG AGC AGC UCA GUG ACU GUC CCC UCC AGC CCU AGG CCC AGC GAG ACC GUC ACC UGC AAC GUU GCC CAC CCG GCC
      220                                         230                                         240
ser thr lys val asp lys lys ile val pro arg asp cys gly cys lys pro cys ile cys thr val pro glu val ser ser val phe
AGC ACC AAG GUG GAC AAG AAA AUU GUG CCC AGG GAU UGU GGU UGU AAG CCU UGC AUA UGU ACA GUC CCA GAA GUA UCA UCU GUC UUC
```

Fig. 5A.

```
ile phe pro pro lys asp     250 leu thr ile thr leu thr pro lys val     260 thr cys val val asp ile ser lys asp     270 pro
AUC UUC CCC CCA AAG GAU         CUC ACC AUU ACU CUG ACU CCU AAG GUC         ACG UGU GUU GUA GAC AUC AGC AAG GAU         CCC glu val gln phe ser trp phe val     280 asp val glu val his gln thr ala     290 gln pro arg val glu val gln phe asn ser     300 thr phe arg
GAG GUC CAG UUC AGC UGG UUU GUA         GAU GUA GAG GUG CAC CAG ACA GCU         CAA CCC CGG GUG GAG GAG CAG UUC AAC AGC         ACU UUC CGC ser val ser glu leu pro ile met     310 his gln leu asn gly lys glu phe     320 lys cys arg val asn ser ala phe pro     330 ala pro
UCA GUC AGU GAA CUU CCC AUC AUG         CAC CAG CUG AAU GGC AAG GAG UUC         AAA UGC AGG GUC AAC AGU GCA UUC CCU         GCC CCC ile glu lys thr ile ser lys thr     340 gly gly arg pro lys ala pro gln     350 val tyr thr ile pro pro pro lys glu     360 lys ala asp
AUC GAG AAA ACC AUC UCC AAA ACC         GGG AGA CCG AAG GCU CCA CAG         GUG UAC ACC AUU CCA CCU CCC AAG GAG         AAG GCC GAU lys val ser leu thr cys met ile     370 thr asp phe phe pro glu asp ile     380 thr val glu trp gln trp asn gly gln     390 pro glu asn tyr
AAA GUC AGU CUG ACC UGC AUG AUA         ACA GAC UUC UUC CCU GAA GAC AUU         ACU GUG GAG UGG CAG UGG AAU GGG CAG         CCA GAG AAC UAC lys asn thr gln pro ile met asn     400 thr asn gly ser tyr phe val tyr     410 ser lys leu asn val gln lys ser asn     420 trp glu ala gly asn
AAG AAC ACU CAG CCC AUC AUG AAC         ACG AAU GGC UCU UAC UUC GUC UAC         AGC AAG CUC AAU GUG CAG AAG AGC AAC         UGG GAG GCA GGA AAU thr phe thr cys ser val leu his     430 glu gly leu his asn his his thr     440 glu lys ser leu ser his ser pro gly     447 lys OP
ACU UUC ACC UGC UCU GUG UUA CAU         GAG GGC CUG CAC AAC CAC CAU ACU         GAG AAG AGC CUC UCC CAC UCU CCU GGU         AAA UGA UGGAGCCCCUCUGGUCCUACAGGACUCUGACACCACCCCUCCCCUGUAUAAAUAAAGCACCCAGCACUGCCUUGGGAAAAAUCCCAGUGUCCU
```

Fig. 5B.

METHODS OF PRODUCING IMMUNOGLOBULINS, VECTORS AND TRANSFORMED HOST CELLS FOR USE THEREIN

CROSS-REFERENCE TO RELATED APPLICATIONS

This application is a continuation of U.S. patent application Ser. No. 06/483,457, filed Apr. 8, 1983, now U.S. Pat. No. 4,816,567, issued Mar. 28, 1989.

BACKGROUND OF THE INVENTION

This invention relates to the field of immunoglobulin production and to modification of naturally occurring immunoglobulin amino acid sequences. Specifically, the invention relates to using recombinant techniques to produce both immunoglobulins which are analogous to those normally found in vertebrate systems and to take advantage of these gene modification techniques to construct chimeric or other modified forms.

A. Immunoglobulins and Antibodies

Antibodies are specific immunoglobulin polypeptides produced by the vertebrate immune system in response to challenge by foreign proteins, glycoproteins, cells, or other antigenic foreign substances. The sequence of events which permits the organism to overcome invasion by foreign cells or to rid the system of foreign substances is at least partially understood. An important part of this process is the manufacture of antibodies which bind specifically to a particular foreign substance. The binding specificity of such polypeptides to a particular antigen is highly refined, and the multitude of specificities capable of being generated by the individual vertebrate is remarkable in its complexity and variability. Thousands of antigens are capable of eliciting responses, each almost exclusively directed to the particular antigen which elicited it.

Immunoglobulins include both antibodies, as above described, and analogous protein substances which lack antigen specificity. The latter are produced at low levels by the lymph system and in increased levels by myelomas.

A.1 Source and Utility

Two major sources of vertebrate antibodies are presently utilized—generation in situ by the mammalian B lymphocytes and in cell culture by B-cell hybrids. Antibodies are made in situ as a result of the differentiation of immature B lymphocytes into plasma cells, which occurs in response to stimulation by specific antigens. In the undifferentiated B cell, the portions of DNA coding for the various regions on the immunoglobulin chains are separated in the genomic DNA. The sequences are reassembled sequentially prior to transcription. A review of this process has been given by Gough, *Trends in Biochem Sci*, 6: 203 (1981). The resulting rearranged genome is capable of expression in the mature B lymphocyte to produce the desired antibody. Even when only a single antigen is introduced into the sphere of the immune system for a particular mammal, however, a uniform population of antibodies does not result. The in situ immune response to any particular antigen is defined by the mosaic of responses to the various determinants which are present on the antigen. Each subset of homologous antibody is contributed by a single population of B-cells—hence in situ generation of antibodies is "polyclonal".

This limited but inherent heterogeneity has been overcome in numerous particular cases by use of hybridoma technology to create "monoclonal" antibodies (Kohler, et al., *Eur. J. Immunol.*, 6: 511 (1976)). In this process, splenocytes or lymphocytes from a mammal which has been injected with antigen are fused with a tumor cell line, thus producing hybrid cells or "hybridomas" which are both immortal and capable of producing the genetically coded antibody of the B cell. The hybrids thus formed we segregated into single genetic strains by selection, dilution, and regrowth, and each strain thus represents a single genetic line. They therefore produce immunoreactive antibodies against a desired antigen which are assured to be homogenous, and which antibodies, referencing their pure genetic parentage, are called "monoclonal". Hybridoma technology has to this time been focused largely on the fusion of murine lines, but human-human hybridomas (Olsson, L. et al., *Proc. Natl. Acad. Sci. (USA)*, 77: 5429 (1980)); human-murine hybridomas (Schlom, J., et al. (ibid) 77: 6841 (1980)) and several other xenogenic hybrid combinations have been prepared as well. Alternatively, primary, antibody producing, B cells have been immortalized in vitro by transformation with viral DNA.

Polyclonal, or, much more preferably monoclonal, antibodies have a variety of useful properties similar to those of the present invention. For example, they can be used as specific immunoprecipitating reagents to detect the presence of the antigen which elicited the initial processing of the B cell genome by coupling this antigen-antibody reaction with suitable detection techniques such as labeling with radioisotopes or with enzymes capable of assay (RIA, EMIT, and ELISA). Antibodies are thus the foundation of immuno diagnostic tests for many antigenic substances. In another important use, antibodies can be directly injected into subjects suffering from an attack by a substance or organism containing the antigen in question to combat this attack. This process is currently in its experimental stages, but its potential is clearly seen. Third, whole body diagnosis and treatment is made possible because injected antibodies are directed to specific target disease tissues, and thus can be used either to determine the presence of the disease by carrying with them a suitable label, or to attack the diseased tissue by carrying a suitable drug.

Monoclonal antibodies produced by hybridomas, while theoretically effective as suggested above and clearly preferable to polyclonal antibodies because of their specificity, suffer from certain disadvantages. First, they tend to be contaminated with other proteins and cellular materials of hybridoma, (and, therefore, mammalian) origin. These cells contain additional materials, notably nucleic acid fragments, but protein fragments as well, which are capable of enhancing, causing, or mediating carcinogic responses. Second, hybridoma lines producing monoclonal antibodies tend to be unstable and may alter the structure of antibody produced or stop producing antibody altogether (Kohler, G., et al. *Proc. Natl. Acad. Sci (USA)* 77: 2197 (1980); Morrison, S. L., *J. Immunol.* 123: 793 (1979)). The cell line genome appears to alter itself in response to stimuli whose nature is not currently known, and this alteration may result in production of incorrect sequences. Third, both hybridoma and B cells inevitably produce certain antibodies in glycosylated form (Melchers, F., *Biochemistry*, 10: 653 (1971)) which, under some circumstances, may be undesirable. Fourth, production of both monoclonal and polyclonal antibodies is relatively expensive. Fifth, and perhaps most important, production by current techniques (either by hybridoma or by B cell response) does not permit manipulation of the genome so as to produce antibodies with more effective design components than those normally elicited in response to antigens from the mature B cell in situ. The antibodies of the present invention do not suffer from the foregoing drawbacks, and, furthermore, offer the opportunity to provide molecules of superior design.

Even those immunoglobulins which lack the specificity of antibodies are useful, although over a smaller spectrum of potential uses than the antibodies themselves. In presently understood applications, such immunoglobulins are helpful in proteins replacement therapy for globulin related anemia. In this context, an inability to bind to antigen is in fact helpful, as the therapeutic value of these proteins would be impaired by such functionality. At present, such non-specific antibodies are derivable in quantity only from myeloma cell cultures suitably induced. The present invention offers an alternative, more economical source. It also offers the opportunity of canceling out specificity by manipulating the four chains of the tetramer separately.

A.2 General Structure Characteristics

The basic immunoglobin structural unit in vertebrate systems is now well understood (Edelman, G. M., *Ann. N.Y. Acad. Sci.*, 190: 5 (1971)). The units are composed of two identical light polypeptide chains of molecular weight approximately 23,000 daltons, and two identical heavy chains of molecular weight 53,000–70,000. The four chains are joined by disulfide bonds in a "Y" configuration wherein the light chains bracket-the heavy-chains starting at the mouth of the Y and continuing through the divergent region as shown in FIG. 1. The "branch" portion, as there indicated, is designated the Fab region. Heavy chains are classified as gamma, mu, alpha, delta, or epsilon, with some subclasses among them, and the nature of this chain, as it has a long constant region, determines the "class"of the antibody as IgG, IgM, IgA, IgD, or IgE. Light chains are classified-as either kappa or lambda. Each heavy chain class can be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells. However, if non-covalent association of the chains can be effected in the correct geometry, the aggregate will still be capable of reaction with antigen, or of utility as a protein supplement as a non-specific immunoglobulin.

The amino acid sequence runs from the N-terminal end at the top of the Y to the C-terminal end at the bottom of each chain. At the N-terminal end is a variable region which is specific for the antigen which elicited it, and is approximately 100 amino acids in length, there being slight variations between light and heavy chain and from antibody to antibody. The variable region is linked in each chain to a constant region which extends the remaining length of the chain. Linkage is seen, at the genomic level, as occurring through a linking sequence known currently as the "J" region in the light chain gene, which encodes about 12 amino acids, and as a combination of "D" region and "J" region in the heavy chain gene, which together encode approximately 25 amino acids.

The remaining portions of the chain are referred to as constant regions and within a particular class do not to vary with the specificity of the antibody (i.e., the antigen eliciting it), As stated above, there are five known major classes of constant regions which determine the class of the immunoglobulin molecule (IgG, IgM, IgA, IgD, and IgE corresponding to $\gamma$, $\mu$, $\alpha$, $\delta$, and $\epsilon$ heavy chain constant regions). The constant region or class determines subsequent effector function of the antibody, including activation of complement (Kabat, E. A., *Structural Concepts in Immunology and Immunochemistry*, 2nd Ed., p. 413–436, Holt, Rinehart Winston (1976)), and other cellular responses (Andrews, D. W., et al., *Clinical Immunobiology* pp 1–18, W. B. Sanders (1980); Kohl, S., et al., *Immunology*, 48: 187 (1983)); while the variable region determines the antigen with which it will react.

B. Recombinant DNA Technology

Recombinant DNA technology has reached sufficient sophistication that it includes a repertoire of techniques for cloning and expression of gene sequences. Various DNA sequences can be recombined with some facility, creating new DNA entities capable of producing heterologous protein product in transformed microbes and cell cultures. The general means and methods for the in vitro ligation of various blunt ended or "sticky" ended fragments of DNA, for producing expression vectors, and for transforming organisms are now in hand.

DNA recombination of the essential elements (i.e., an origin of replication, one or more phenotypic selection characteristics, expression control sequence, heterologous gene insert and remainder vector) generally is performed outside the host cell. The resulting recombinant replicable expression vector, or plasmid, is introduced into cells by transformation and large quantities of the recombinant vehicle is obtained by growing the transformants. Where the gene is properly inserted with reference to portions which govern the transcription and translation of the encoded DNA message, the resulting expression vector is useful to produce the polypeptide sequence for which the inserted gene codes, a process referred to as "expression." The resulting product may be obtained by lysis, if necessary, of the host cell and recovery of the product by appropriate purifications from other proteins.

In practice, the use of recombinant DNA technology can express entirely heterologous polypeptides—so-called direct expression—or alternatively may express a heterologous polypeptide fused to a portion of the amino acid sequence of a homologous polypeptide. In the latter cases, the intended bioactive product is sometimes rendered bioinactive within the fused, homologous/heterologous polypeptide until it is cleaved in an extracellular environment.

The art of maintaining cell or tissue cultures as well as microbial systems for studying genetics and cell physiology is well established. Means and methods are available for maintaining permanent cell lines, prepared by successive serial transfers from isolated cells. For use in research, such cell lines are maintained on a solid support in liquid medium, or by growth in suspension containing support nutriments. Scale-up for large preparations seems to pose only mechanical problems.

SUMMARY OF THE INVENTION

The invention relates to antibodies and to non-specific immunoglobulins (NSIs) formed by recombinant techniques using suitable host cell cultures. These antibodies and NSIs can be readily prepared in pure "monoclonal" form. They can be manipulated at the genomic level to produce chimeras of variants which draw their homology from species which differ from each other. They can also be manipulated at the protein level, since all four chains do not need to be produced by the same cell. Thus, there are a number of "types" of immunoglobulins encompassed by the invention.

First, immunoglobulins, particularly antibodies, are produced using recombinant techniques which mimic the amino acid sequence of naturally occurring antibodies produced by either mammalian B cells in situ, or by B cells fused with suitable immortalizing tumor lines, i.e., hybridomas.

Second, the methods of this invention produce, and the invention is directed to, immunoglobulins which comprise polypeptides not hitherto found associated with each other in nature. Such reassembly is particularly useful in producing "hybrid" antibodies capable of binding more than one antigen; and in producing "composite" immunoglobulins wherein heavy and light chains of different origins essentially damp out specificity. Third, by genetic manipulation, "chimeric" antibodies can be formed wherein, for example, the variable regions correspond to the amino acid sequence from one mammalian model system, whereas the constant region mimics the amino acid sequence of another. Again, the derivation of these two mimicked sequences may be from different species. Fourth, also by genetic manipulation, "altered" antibodies with improved specificity and other characteristics can be formed.

Two other types of immunoglobulin-like moieties may be produced: "univalent" antibodies, which are useful as homing carriers to target tissues, and "Fab proteins" which include only the "Fab" region of an immunoglobulin molecule i.e., the branches of the "Y". These univalent antibodies and Fab fragments may also be "mammalian" i.e., mimic mammalian amino acid sequences; novel assemblies of mammalian chains, or chimeric, where for example, the constant and variable sequence patterns may be of different origin. Finally, either the light chain or heavy chain alone, or portions, thereof, produced by recombinant techniques are included in the invention and may be mammalian or chimeric.

In other aspects, the invention is directed to DNA which encodes the aforementioned NSIs, antibodies, and portions thereof, as well as expression vectors or plasmids capable of effecting the production of such immunoglobulins in suitable host cells. It includes the host cells and cell cultures which result from transformation with these vectors. Finally, the invention is directed to methods of producing these NSIs and antibodies, and the DNA sequences, plasmids, and transformed cells intermediate to them.

BRIEF DESCRIPTION OF THE DRAWINGS

FIGS. 2A–B shows the detailed sequence of the cDNA insert of pK17G4 which encodes kappa anti CEA chain.

FIG. 3 shows the coding sequence of the fragment shown in FIG. 2, along with the corresponding amino acid sequence.

FIGS. 4A–C shows the combined detailed sequence of the cDNA inserts of pγ298 and pγ11 which encode gamma anti CEA chain.

FIGS. 5A–B shows the corresponding amino acid sequence encoded by the fragment in FIG. 4.

DETAILED DESCRIPTION

A. Definitions

Figure 1:
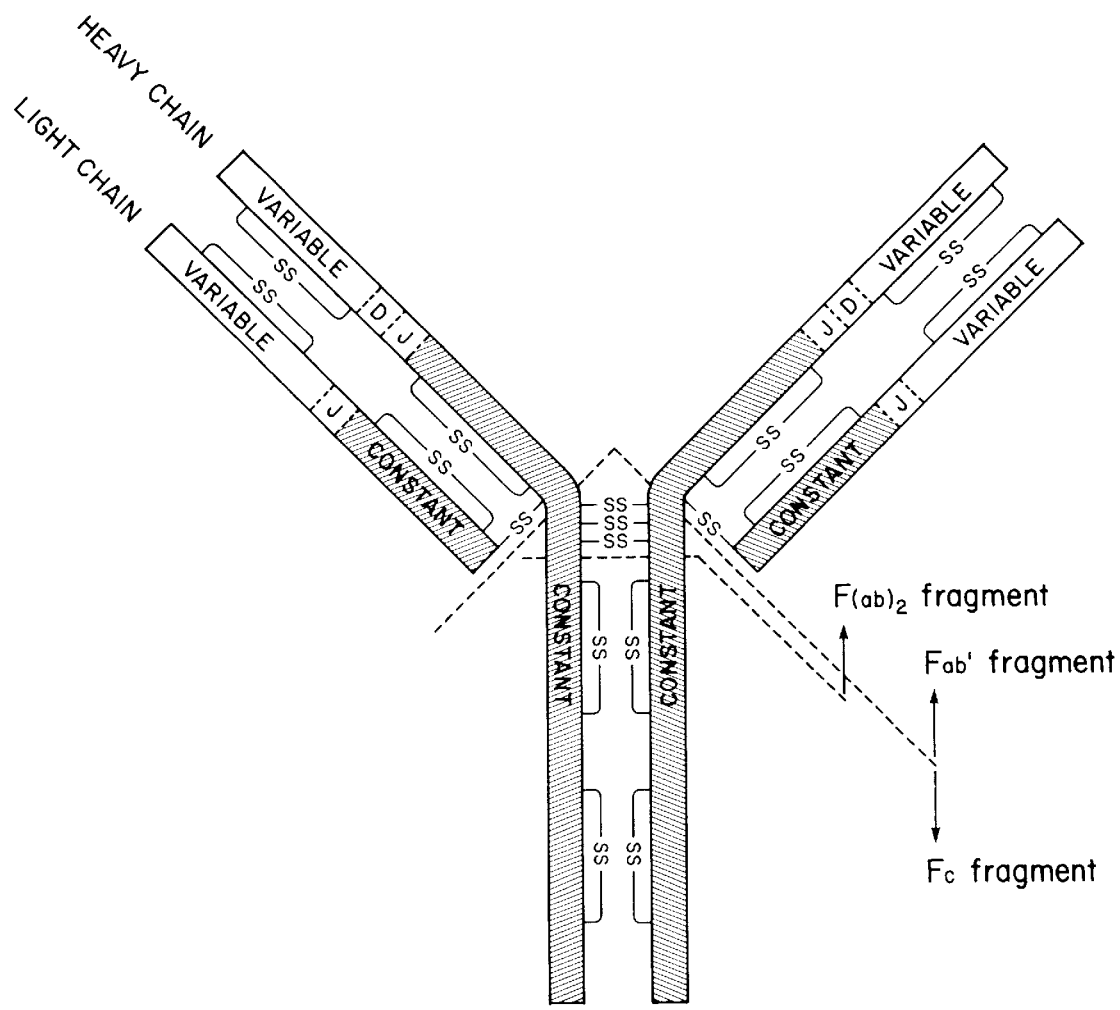
FIG. 1 is a representation of the general structure of immunoglobulins.

As used herein, "antibodies" refers to tetramers or aggregates thereof which have specific immunoreactive activity, comprising light and heavy chains usually aggregated in the "Y" configuration of FIG. 1, with or without covalent linkage between them; "immunoglobulins" refers to such assemblies whether or not specific immunoreactive activity is a property. "Non-specific immunoglobulin" ("NSI") means those immunoglobulins which do not possess specificity—i.e., those which are not antibodies.

"Mammalian antibodies" refers to antibodies wherein the amino acid sequences of the chains are homologous with those sequences found in antibodies produced by mammalian systems, either in situ, or in hybridomas. These antibodies mimic antibodies which are otherwise capable of being generated, although in impure form, in these traditional systems.

"Hybrid antibodies" refers to antibodies wherein chains are separately homologous with referenced mammalian antibody chains and represent novel assemblies of them, so that two different antigens are precipitable by the tetramer. In hybrid antibodies, one pair of heavy and light chain is homologous to antibodies raised against one antigen, while the other pair of heavy and light chain is homologous to those raised against another antigen. This results in the property of "divalence" i.e., ability to bind two antigens simultaneously. Such hybrids may, of course, also be formed using chimeric chains, as set forth below.

"Composite" immunoglobulins means those wherein the heavy and light chains mimic those of different species origins or specificities, and the resultant is thus likely to be a non-specific immunoglobulin (NSI), i.e.—lacking in antibody character.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals while the constant portions are homologous to the sequences in antibodies derived from another. One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source.

However, the definition is not limited to this particular example. It includes any antibody in which either or both of the heavy or light chains are composed of combinations of sequences mimicking the sequences in antibodies of different sources, whether these sources be differing classes, differing antigen responses, or differing species of origin and whether or not the fusion point is At the variable/constant boundary. Thus, it is possible to produce antibodies in which neither the constant nor the variable region mimic known antibody sequences. It then becomes possible, for example, to construct antibodies whose variable region has a higher specific affinity for a particular antigen, or whose constant region can elicit enhanced complement fixation or to make other improvements in properties possessed by a particular constant region.

"Altered antibodies" means antibodies wherein the amino acid sequence has been varied from that of a mammalian or other vertebrate antibody. Because of the relevance of recombinant DNA techniques to this invention, one need not be confined to the sequences of amino acids found in natural antibodies; antibodies can be redesigned to obtain desired characteristics. The possible variations are many and range from the changing of just one or a few amino acids to the complete redesign of, for example, the constant region. Changes in the constant region will, in general, be made in order to improve the cellular process characteristics, such as complement fixation, interaction with membranes, and other effector functions. Changes in the variable region will be made in order to improve the antigen binding characteristics. The antibody can also be engineered so as to aid the specific delivery of a toxic agent according to the "magic bullet" concept. Alterations, can be made by standard recombinant techniques and also by oligonucleotide-directed mutagenesis techniques (Dalbadie-McFarland, et al *Proc. Natl. Acad. Sci. (USA)*, 79:6.409 (1982)).

"Univalent antibodies" refers to aggregations which comprise a heavy chain/light chain dimer bound to the Fc (or stem) region of a second heavy chain. Such antibodies are specific for antigen but have the additional desirable property of targeting tissues with specific antigenic surfaces, without causing its antigenic effectiveness to be impaired—i.e., there is no antigenic modulation. This phenomenon and the property of univalent antibodies in this regard is set forth in Glennie, M. J., et al., *Nature*, 295: 712 (1982). Univalent antibodies have heretofore been formed by proteolysis.

"Fab" region refers to those portions of the chains which are roughly equivalent, or analogous, to the sequences which comprise the Y branch portions of the heavy chain and to the light chain in its entirety, and which collectively (in aggregates) have been shown to exhibit antibody activity. "Fab protein", which protein is one of the aspects of the invention, includes aggregates of one heavy and one light chain (commonly known as Fab'), as well as tetramers which correspond to the two branch segments of the antibody Y, (commonly known as F(ab)$_2$), whether any of the above are covalently or non-covalently aggregated, so long as the aggregation is capable of selectively reacting with a particular antigen or antigen family. Fab antibodies have, as have univalent ones, been formed heretofore by proteolysis, and share the property of not eliciting antigen modulation on target tissues. However, as they lack the "effector" Fc: portion they cannot effect, for example, lysis of the target cell by macrophages.

"Fab protein" has similar subsets according to the definition of the present invention as does the general term "antibodies" or "immunoglobulins". Thus, "mammalian" Fab protein, "hybrid" Fab protein "chimeric" Fab and "altered" Fab protein are defined analogously to the corresponding definitions set forth in the previous paragraphs for the various types of antibodies.

Individual heavy or light chains may of course be "mammalian", "chimeric" or "altered" in accordance with the above. As will become apparent from the detailed description of the invention, it is possible, using the techniques disclosed to prepare other combinations of the four-peptide chain aggregates, besides those specifically defined, such as hybrid antibodies containing chimeric light and mammalian heavy chains, hybrid Fab proteins containing chimeric Fab proteins of heavy chains associated with mammalian light chains, and so forth.

"Expression vector" includes vectors which are capable of expressing DNA sequences contained therein, i.e., the coding sequences are operably linked to other sequences capable of effecting their expression. It is implied, although not always explicitly stated, that these expression vectors must be replicable in the host organisms either as episomes or as an integral part of the chromosomal DNA. Clearly a lack of replicability would render them effectively inoperable. A useful, but not a necessary, element of an effective expression vector is a marker encoding sequence—i.e. a sequence encoding a protein which results in a phenotypic property (e.g. tetracycline resistance) of the cells containing the protein which permits those cells to be readily identified. In sum, "expression vector" is given a functional definition, and any DNA sequence which is capable of effecting expression of a specified contained DNA code is included in this term, as it is applied to the specified sequence. As at present, such vectors are frequently in the form of plasmids, thus "plasmid" and "expression vector" are often used interchangeably. However, the invention is intended to include such other forms of expression vectors which serve equivalent functions and which may, from time to time become known in the art.

"Recombinant host cells" refers to cells which have been transformed with vectors constructed using recombinant DNA techniques. As defined herein, the antibody or modification thereof produced by a recombinant host cell is by virtue of this transformation, rather than in such lesser amounts, or more commonly, in such less than detectable amounts, as would be produced by the untransformed host.

In descriptions of processes for isolation of antibodies from recombinant hosts, the terms "cell" and "cell culture" are used interchangeably to denote the source of antibody unless it is clearly specified otherwise. In other words, recovery of antibody from the "cells" may mean either from spun down whole cells, or from the cell culture containing both the medium and the suspended cells.

B. Host Cell Cultures and Vectors

The vectors and methods disclosed herein are suitable for use in host cells over a wide range of prokaryotic and eukaryotic organisms.

In-general, of course, prokaryotes are preferred for cloning of DNA sequences in constructing the vectors useful in the invention. For example, *E. coli* K12 strain 294 (ATCC No. 31446) is particularly useful. Other microbial strains which may be used include *E. coli* strains such as *E. coli* B, and *E. coli* X1776 (ATTC No. 31537). These examples are, of course, intended to be illustrative rather than limiting.

Prokaryotes may also be used for expression. The aforementioned strains, as well as *E. coli* W3110 (F$^-$, λ$^-$, prototrophic, ATTC No. 27325), bacilli such as *Bacillus subtilus*, and other enterobacteriaceae such as *Salmonella typhimurium* or *Serratia marcesans*, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (Bolivar, et al., *Gene* 2: 95 (1977)). PBR322 contains genes for ampicillin and tetracycline resistance and thus provides easy means for identifying transformed cells. The pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems Chang et al, *Nature* 275: 615 (1978); Itakura, et al, *Science* 198: 1056 (1977); (Goeddel et al, *Nature* 281: 544 (1979)) and a tryptophan (trp) promoter system (Goeddel, et al, *Nucleic kids Res.*, 8: 4057 (1980); EPO Appl Publ No. 0036776). While these are the most commonly used, other microbial promoters have been discovered and utilized., and details concerning their nucleotide sequences have been published, enabling a skilled worker to ligate them functionally with plasmid vectors (Siebenlist, et al, Cell 20: 269 (1980)).

In addition to prokaryates, eukaryotic microbes, such as yeast cultures may also be used. *Saccharomyces cerevisiae*, or common baker's yeast is the most commonly used among eukaryotic microorganisms, although a number of other strains are commonly available. For expression in Saccharomyces, the plasmid YRp7, for example, (Stinchcomb et al, *Nature*, 282: 39 (1979); Kingsman et al, *Gene*, 7: 141 (1979); Tschemper, et al, *Gene*, 10: 157 (1980)) is commonly used. This plasmid already contains the trp1 gene which provides a selection marker for a mutant strain of yeast lacking the ability to grow in tryptophan, for example ATCC No. 44076 or PEP4-1 (Jones, *Genetics*, 85: 12 (1977)). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman, et al., *J. Biol. Chem.*, 255: 2073 (1980)) or other glycolytic enzymes (Hess, et al, *J. Adv. Enzyme Reg.*, 7: 149 (1968); Holland, et al, *Biochemistry*, 17: 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization (Holland, ibid.). Any plasmid vector containing yeast-compatible promoter, origin of replication and termination sequences is suitable.

In addition to microorganisms cultures of cells derived from multicellular organisms may also be used as hosts. In principle, any such cell culture is workable, whether from vertebrate or invertebrate culture. However interest has been greatest in vertebrate cells, and propagation of vertebrate cells in culture (tissue culture) has become a routine procedure in recent years (*Tissue Culture*, Academic Press, Kruse and Patterson, editors (1973)). Examples of such useful host cell lines are VERO and HeLa cells, Chinese hamster ovary (CHO) cell lines, and W138, BHK, COS-7 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication (Fiers, et al, *Nature*, 273: 113 (1978)) incorporated herein by reference. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g. Polyoma, Adeno, VSV, BPV, etc.) source, or may be provided by the host cell chromosomal replication mechanism. If the vector is integrated into the host cell chromosome, the latter is often sufficient.

It will be understood that this invention, although described herein in terms of a preferred embodiment, should not be construed as limited to those host cells, vectors and expression systems exemplified.

C. Methods Employed

C.1 Transformation

If cells without formidable cell wall barriers are used as host cells, transfection is carried out by the calcium phosphate precipitation method as described by Graham and Van der Eb, *Virology*, 52: 546 (1978). However, other methods for introducing DNA into cells such as by nuclear injection or by protoplast fusion may also be used.

If prokaryotic cells or cells which contain substantial cell wall constructions are used, the preferred method of transfection is calcium treatment using calcium chloride as described by Cohen, F. N. et al *Proc. Natl. Acad. Sci. (USA)* 69: 2110 (1972).

C.2 Vector Construction

Construction of suitable vectors containing the desired coding and control sequences employ standard ligation techniques. Isolated plasmids or DNA fragments are cleaved, tailored, and religated in the form desired to form the plasmids required. The methods employed are not dependent on the DNA source, or intended host.

Cleavage is performed by treating with restriction enzyme (or enzymes) in suitable buffer. In general, about 1 µg plasmid or DNA fragments is used with about 1 unit of enzyme in about 20 µl of buffer solution. (Appropriate buffers and substrate amounts for particular restriction enzymes are specified by the manufacturer.) Incubation times of about 1 hour at 37° C. are workable. After incubations, protein is removed by extraction with phenol and chloroform, and the nucleic acid is recovered from the aqueous fraction by precipitation with ethanol.

If blunt ends are required, the preparation is treated for 15 minutes at 15° with 10 units of *E. coli* DNA Polymerase I (Klenow), phenol-chloroform extracted, and ethanol precipitated.

Size separation of the cleaved fragments is performed using 6 percent polyacrylamide gel described by Goeddel, D., et al, *Nucleic Acids Res.*, 8: 4057 (1980) incorporated herein by reference.

For ligation, approximately equimolar amounts of the desired components, suitably end tailored to provide correct matching are treated with about 10 units T4 DNA ligase per 0.5 µg DNA. (When cleaved vectors are used as components, it may be useful to prevent religation of the cleaved vector by pretreatment with bacterial alkaline phosphatase.)

In the examples described below correct ligations for plasmid construction are confirmed by transforming *E. coli* K12 strain 294 (ATCC 31446) with the ligation mixture. Successful transformants were selected by ampicillin or tetracycline resistance depending on the mode of plasmid construction. Plasmids from the transformants were then prepared, analyzed by restriction and/or sequenced by the method of Messing, et al, *Nucleic Acids Res.,* 9:309 (1981) or by the method of Maxam, et al, *Methods in Enzymology,* 65:499 (1980).

D. Outline of Procedures

D.1 Mammalian Antibodies

The first type of antibody which forms a part of this invention, and is prepared by the methods thereof, is "mammalian antibody"-one wherein the heavy and light chains mimic the amino acid sequences of an antibody otherwise produced by a mature mammalian B lymphocyte either in situ or when fused with an immortalized cell as part of a hybridoma culture. In outline, these antibodies are produced as follows:

Messenger RNA coding for heavy or light chain is isolated from a suitable source, either mature B cells or a hybridoma culture, employing standard techniques of RNA isolation, and the use of oligo-dT cellulose chromatography to segregate the poly-A mRNA. The poly-A mRNA may, further, be fractionated to obtain sequences of sufficient size to code for the amino acid sequences in the light or heavy chain of the desired antibody as the case may be.

A cDNA library is then prepared from the mixture of mRNA using a suitable primer, preferably a nucleic acid sequence which is characteristic of the desired cDNA. Such a primer may be hypothesized and synthesized based on the amino acid sequence of the antibody if the sequence is known. In the alternative cDNA from unfractionated poly-A mRNA from a cell line producing the desired antibody or poly-dT may also be used. The resulting cDNA is optionally size fractionated on polyacrylamide gel and then extended with, for example, dC residues for annealing with pBR322 or other suitable cloning vector which has been cleaved by a suitable restriction enzyme, such as Pst I, and extended with dG residues. Alternative means of forming cloning vectors containing the cDNA using other tails and other cloning vector remainder may, of course, also be used but the foregoing is a standard and preferable choice. A suitable host cell strain, typically *E. coli,* is transformed with the annealed cloning vectors, and the successful transformants identified by means of, for example, tetracycline resistance or other phenotypic characteristic residing on the cloning vector plasmid.

Successful transformants are picked and transferred to microtiter dishes or other support for further growth and preservation. Nitrocellulose filter imprints of these growing cultures are then probed with suitable nucleotide sequences containing bases known to be complementary to desired sequences in the cDNA. Several types of probe may be used, preferably synthetic single stranded DNA sequences labeled by kinasing with $ATP^{32}$. The cells fixed to the nitrocellulose filter are lysed, the DNA denatured, and then fixed before reaction with kinased probe. Clones which successfully hybridize are detected by contact with a photoplate, then plasmids from the growing colonies isolated and sequenced by means known in the art to verify that the desired portions of the gene are present.

The desired gene fragments are excised and tailored to assure appropriate reading frame with the control segments when inserted into suitable expression vectors. Typically, nucleotides are added to the 5' end to include a start signal and a suitably positioned restriction endonuclease site.

The tailored gene sequence is then positioned in a vector which contains a promoter in reading frame with the gene and compatible with the proposed host cell. A number of plasmids such as those described in U.S. patent application Ser. Nos. 307,473; 291,892; and 305,657 (EPO Publ. Nos. 0036776; 0048970 and 0051873) have been described which already contain the appropriate promoters, control sequences, ribosome binding sites, and transcription termination sites, as well as convenient markers.

In the present invention, the gene coding for the light chain and that coding for the heaving chain are recovered separately by the procedures outlined above. Thus then may be inserted into separate expression plasmids, or together in the same plasmid, so long as each is under suitable promoter and translation control.

The expression vectors constructed above are then used to transform suitable cells. The light and heavy chains may be transformed into separate cell cultures, either of the same or of differing species; separate plasmids for light and heavy chain may be used to co-transform a single cell culture, or, finally, a single expression plasmid containing both genes and capable of expressing the genes for both light and heavy chain may be transformed into a single cell culture.

Regardless of which of the three foregoing options is chosen, the cells are grown under conditions appropriate to the production of the desired protein. Such conditions are primarily mandated by the type of promoter and control systems used in the expression vector, rather than by the nature of the desired protein. The protein thus produced is then recovered from the cell culture by methods known in the art, but choice of which is necessarily dependent on the form in which the protein is expressed. For example, it is common for mature heterologous proteins expressed in *E. coli* to be deposited within the cells as insoluble particles which require cell lysis and solubilization in denaturant to permit recovery. On the other hand, proteins under proper synthesis circumstances, in yeast and bacterial strains, can be secreted into the medium (yeast and gram positive bacteria) or into the periplasmic space (gram negative bacteria) allowing recovery by less drastic procedures. Tissue culture cells as hosts also appear, in general, to permit reasonably facile recovery of heterologous proteins.

When heavy and light chain are coexpressed in the same host, the isolation procedure is designed so as to recover reconstituted antibody. This can be accomplished in vitro as described below, or might be possible in vivo in a microorganism which secretes the IgG chains out of the reducing environment of the cytoplasm. A more detailed description is given in D.2, below.

D.2 Chain Recombination Techniques

The ability of the method of the invention to produce heavy and light chains or portions thereof, in isolation from each other offers the opportunity to obtain unique and unprecedented assemblies of immunoglobulins, Fab regions, and univalent antibodies. Such preparations require the use of techniques to reassemble isolated chains. Such means are known in the art, and it is, thus, appropriate to review them here.

While single chain disulfide bond containing proteins have been reduced and reoxidized to regenerate in high yield native structure and activity (Freedman, R. B., et al. In *Enzymology of Post Translational Modification of Proteins,* I: 157–212 (1980) Academic Press, NY.), proteins which consist of discontinuous polypeptide chains held together by disulfide bonds are more difficult to reconstruct in vitro after reductive cleavage. Insulin, a cameo case, has received much experimental attention over the years, and can now be reconstructed so efficiently that an industrial process has been built around it (Chance, R. E., et al., In *Peptides: Proceedings of the Seventh Annual American Peptide Symposium* (Rich, D. H. and Gross. E., eds.) 721–728, Pierce Chemical Co., Rockford, Ill. (1981)).

Immunoglobulin has proved a more difficult problem than insulin. The tetramer is stabilized intra and intermolecularly by 15 or more disulfide bonds. It has been possible to recombine heavy and light chains, disrupted by cleavage of only the interchain disulfides, to regain antibody activity even without restoration of the inter-chain disulfides (Edelman, G. M., et al., *Proc. Natl. Acad. Sci. (USA)* 50: 753 (1963)). In addition, active fragments of IgG formed by proteolysis (Fab fragments of ~50,000 MW) can be split into their fully reduced heavy chain and light chain components and fairly efficiently reconstructed to give active antibody (Haber, E., *Proc. Natl. Acad. Sci. (USA)* 52: 1099 (1964); Whitney, P. L., et al., *Proc. Natl. Acad. Sci. (USA)* 53: 524 (1965)). Attempts to reconstitute active antibody from fully reduced native IgG have been largely unsuccessful, presumably due to insolubility of the reduced chains and of side products or intermediates in the refolding pathway (see discussion in Freedman, M. H., et al., *J. Biol. Chem.* 241: 5225 (1966)). If, however, the immunoglobulin is randomly modified by polyalanylation of its lysines before complete reduction, the separated chains have the ability to recover antigen-combining activity upon reoxidation (ibid).

A particularly suitable method for immunoglobulin reconstitution is derivable from the now classical insulin recombination studies, wherein starting material was prepared by oxidative sulfitolysis, thus generating thiol-labile S-sulfonate groups at all cysteines in the protein, non-reductively breaking disulfides (Chance et al. (supra)). Oxidative sulfitolysis is a mild disulfide cleavage reaction (Means, G. E., et al., *Chemical Modification of Proteins,* Holden-Day, San Francisco (1971)) which is sometimes more gentle than reduction, and which generates derivatives which are stable until exposed to mild reducing agent at which time disulfide reformation can occur via thiol-disulfide interchange. In the present invention the heavy and light chain S-sulfonates generated by oxidative sulfitolysis were reconstituted utilizing both air oxidation and thiol-disulfide interchange to drive disulfide bond formation. The general procedure is set forth in detail in U.S. Ser. No. 452,187, filed Dec. 22, 1982 (EPO Appln. No. 83.307840.5), incorporated herein by reference.

D.3 Variants Permitted by Recombinant Technology

Using the techniques described in paragraphs D.1 and D.2, additional operations which were utilized to gain efficient production of mammalian antibody can be varied in quite straightforward and simple ways to produce a great variety of modifications of this basic antibody form. These variations are inherent in the use of recombinant technology, which permits modification at a genetic level of amino acid sequences in normally encountered mammalian immunoglobulin chains, and the great power of this approach lies in its ability to achieve these variations, as well as in its potential for economic and specific production of desired scarce, and often contaminated, molecules. The variations also inhere in the ability to isolate production of individual chains, and thus create novel assemblies.

Briefly, since genetic manipulations permit reconstruction of genomic material in the process of construction of expression vectors, such reconstruction can be manipulated to produce new coding sequences for the components of "natural" antibodies or immunoglobulins. As discussed in further detail below, the coding sequence for a mammalian heavy chain may not be derived entirely from a single source or single species, but portions of a sequence can be recovered by the techniques described in D.1 from differing pools of mRNA, such as murine-murine hybridomas, human-murine hybridomas, or B cells differentiated in response to a series of antigen challenges. The desired portions of the sequences in each case can be recovered using the probe and analysis techniques described in D.1, and recombined in an expression vector using the same ligation procedures as would be employed for portions of the same model sequence. Such chimeric chains can be constructed of any desired length; hence, for example, a complete heavy chain can be constructed, or only sequence for the Fab region thereof.

The additional area of flexibility which arises from the use of recombinant techniques results from the power to produce heavy and light chains or fragments thereof in separate cultures or of unique combinations of heavy and light chain in the same culture, and to prevent reconstitution of the antibody or immunoglobulin aggregation until the suitable components are assembled. Thus, while normal antibody production results automatically in the formation of "mammalian antibodies" because the light and heavy chain portions are constructed in response to a particular determinant in the same cell, the methods of the present invention present the opportunity to assemble entirely new mixtures. Somewhat limited quantities of "hybrid" antibodies have been produced by "quadromas" i.e., fusions of two hybridoma cell cultures which permit random assemblies of the heavy and light chains so produced.

The present invention permits a more controlled assembly of desired chains, either by mixing the desired chains in vitro, or by transforming the same culture with the coding sequences for the desired chains.

D.4 Composite Immunoglobulins

The foregoing procedure, which describes in detail the recombinant production of mammalian antibodies is employed with some modifications to construct the remaining types of antibodies or NSIs encompassed by the present invention. To prepare the particular embodiment of composite non-specific immunoglobulin wherein the homology of the chains corresponds to the sequences of immunoglobulins of different specificities, it is of course, only necessary to prepare the heavy and light chains in separate cultures and reassemble them as desired.

For example, in order to make an anti-CEA light chain/antihepatitis heavy chain composite antibody, a suitable source for the mRNA used as a template for the light chain clone would comprise, for instance, the anti CEA producing cell line of paragraph E.1. The mRNA corresponding to heavy chain would be derived from B cells raised in response to hepatitis infection or from hybridoma in which the B cell was of this origin. It is clear that such composites can be assembled using the methods of the invention almost at will, and are limited only by available sources of mRNA suitable for use as templates for the respective chains. All other features of the process are similar to those described above.

D.5 Hybrid Antibodies

Hybrid antibodies are particularly useful as they are capable of simultaneous reaction with more than one antigen. Pairs of heavy and light chains corresponding to chains of antibodies for different antigens, such as those set forth in paragraph D.4 are prepared in four separate cultures, thus preventing premature assembly of the tetramer. Subsequent mixing of the four separately prepared peptides then permits assembly into the desired tetramers. While random aggregation may lead to the formation of considerable undesired product, that portion of the product in which homologous light and heavy chains are bound to each other and mismatched to another pair gives the desired hybrid antibody.

D.6 Chimeric Antibodies

For construction of chimeric antibodies (wherein, for example, the variable sequences are separately derived from the constant sequences) the procedures of paragraph C.1 and D.2 are again applicable with appropriate additions and modifications. A preferred procedure is to recover desired portions of the genes encoding for parts of the heavy and light chains from suitable, differing, sources and then to religate these fragments using restriction endonucleases to reconstruct the gene coding for each chain.

For example, in a particularly preferred chimeric construction, portions of the heavy chain gene and of the light chain gene which encode the variable sequences of antibodies produced by a murine hybridoma culture are recovered and closed from this culture and gene fragments encoding the constant regions of the heavy and light chains for human antibodies recovered and cloned from, for example, human myeloma cells. Suitable restriction enzymes may then be used to ligate the variable portions of the mouse gene to the constant regions of the human gene for each of the two chains. The chimeric chains are produced as set forth in D.1, aggregated as set forth in D.2 and used in the same manner as the non-chimeric forms. Of course, any splice point in the chains can be chosen.

D.7 Altered Antibodies

Altered antibodies present, in essence, an extension of chimeric ones. Again, the techniques of D.1 and D.2 are applicable; however, rather than splicing portions of the chain(s), suitable amino acid alterations, deletions or additions are made using available techniques such as mutagenesis (supra). For example, genes which encode antibodies having diminished complement fixation properties, or which have enhanced metal binding capacities are prepared using such techniques. The latter type may, for example, take advantage of the known gene sequence encoding metalothionein II (Karin, M., et al., *Nature,* 299: 797 (1982)). The chelating properties of this molecular fragment are useful in carrying heavy metals to tumor sites as an aid in tumor imaging (Scheinberg, D. A., et al., *Science,* 215: 19 (1982).

D.8 Univalent Antibodies

In another preferred embodiment, antibodies are formed which comprise one heavy and light chain pair coupled with the Fc region of a third (heavy) chain. These antibodies have a particularly useful property. They can, like ordinary antibodies, be used to target antigenic surfaces of tissues, such as tumors, but, unlike ordinary antibodies, they do not cause the antigenic surfaces of the target tissue to retreat and become non-receptive. Ordinary antibody use results in aggregation and subsequent inactivation, for several hours, of such surface antigens.

The method of construction of univalent antibodies is a straightforward application of the invention. The gene for heavy chain of the desired Fc region is cleaved by restriction enzymes, and only that portion coding for the desired Fc region expressed. This portion is then bound using the technique of D.2 to separately produced heavy chain the desired pairs separated from heavy/heavy and Fc/Fc combinations, and separately produced light chain added. Pre-binding of the two heavy chain portions thus diminishes the probability of formation of ordinary antibody.

D.9 Fab Protein

Similarly, it is not necessary to include the entire gene for the heavy chain portion. All of the aforementioned variations can be superimposed on a procedure for Fab protein production and the overall procedure differs only in that the portion of the heavy chain coding for the amino terminal 220 amino acids is employed in the appropriate expression vector.

E. Specific Examples of Preferred Embodiments

The invention has been described above in general terms and there follow several specific examples of embodiments which set forth details of experimental procedure in producing the desired antibodies. Example E.1 sets forth the general procedure for preparing anti CEA antibody components, i.e. for a "mammalian antibody". Example E.3 sets forth the procedure for reconstitution and thus is applicable to preparation of mammalian, composite, hybrid and chimeric immunoglobulins, and Fab proteins and univalent antibodies. Example E.4 sets forth the procedure for tailoring the heavy or light chain so that the variable and constant regions may be derived from different sources. Example E.5 sets forth the method of obtaining a shortened heavy chain genome which permits the production of the Fab regions and, in an analogous manner, Fc region.

The examples set forth below are included for illustrative purposes and do not limit the scope of the invention.

E.1 Construction of Expression Vectors for Murine anti-CEA Antibody Chains and Peptide Synthesis Carcinoembryonic antigen (CEA) is associated with the surface of certain tumor cells of human origin (Gold, P., et al., *J. Exp. Med.,* 122: 467 (1965)). Antibodies which bind to CEA (anti-CEA antibodies) are useful in early detection of these tumors (Van Nagell, T. R., et al., *Cancer Res.* 40: 502 (1980)), and have the potential for use in treatment of those human tumors which appear to support CEA at their surfaces. A mouse hybridoma cell line which secretes anti-CEA antibodies of the $Ig\gamma_1$ class, CEA.66-E3, has been prepared as described by Wagener, C, et al., *J. Immunol.* (in press) which is incorporated herein by reference, and was used as mRNA source. The production of anti CEA antibodies by this cell line was determined. The N-terminal sequences of the antibodies produced by these cells was compared with those of monoclonal anti CEA as follows. Purified IgG was treated with PCAse (Podell, D. N., et al., BBRC 81: 176 (1978)), and then dissociated in 6M guanidine hydrochloride, 10 mM 2-mercaptoethanol (1.0 mg of immunoglobulin, 5 min, 100° C. water bath). The dissociated chains were separated on a Waters Associates alkyl phenyl column using a linear gradient from 100 percent A (0.1 percent TFA-water) to 90 percent B (TFA/$H_2O$/MeCN 0.1/9.9/90) at a flow rate of 0.8 ml/min. Three major peaks were eluted and analyzed on SDS gels by silver staining. The first two peaks were pure light chain (MW 25,000 daltons), the third peak showed a (7:3) mixture of heavy and light chain. 1.2 nmoles of light chain were sequenced by the method of Shively, J. E., *Methods in Enzymology,* 79: 31 (1981), with an $NH_2$-terminal yield of 0.4 nmoles. A mixture of heavy and light chains (3 nmoles) was also sequenced, and sequence of light chain was deducted from the double sequence to yield the sequence of the heavy chain.

In the description which follows, isolation and expression of the genes for the heavy and light chains for anti CEA antibody produced by CEA.66-E3 are described. As the constant regions of these chains belong to the gamma and kappa families, respectively, "light chain" and "kappa chain", and "heavy chain" and "gamma chain", respectively, are used interchangeably below.

E.1.1 Isolation of Messenger RNA for Anti CEA Light and Heavy (Kappa and Gamma) Chains Total RNA from CEA.66-E3 cells was extracted essentially as reported by Lynch et al, *Virology*, 98: 251 (1979). Cells were pelleted by centrifugation and approximately 1 g portions of pellet resuspended in 10 ml of 10 mM NaCl, 10 mM Tris HCl (pH 7.4), 1.5 mM $MgCl_2$. The resuspended cells were lysed by addition of non-ionic detergent NP-40 to a final concentration of 1 percent, and nuclei removed by centrifugation. After addition of SDS (pH 7.4) to 1 percent final concentration, the supernatant was extracted twice with 3 ml portions of phenol (redistilled)/chloroform: isoamyl alcohol 25:1 at 4° C. The aqueous phase was made 0.2 M in NaCl and total RNA was precipitated by addition of two volumes of 100 percent ethanol and overnight storage at −20° C. After centrifugation, polyA mRNA was purified from total RNA by oligo-dT cellulose chromatography as described by Aviv and Leder, *Proc. Nat'l, Acad. Sci. (USA)*, 69: 1408 (19672), 142 μg of polyA mRNA was obtained from 1 g cells.

E.1.2 Preparation of *E. coli* Colony Library Containing Plasmids with Heavy and Light DNA Sequence Inserts 5 μg of the unfractionated polyA mRNA prepared in paragraph E.1.1 was used as template for oligo-dT primed preparation of double-stranded (ds) cDNA by standard procedures as described by Goeddel et al., *Nature* 281: 544 (1979) and Wickens et al., *J. Biol. Chem.* 253: 2483 (1978) incorporated herein by reference. The cDNA was size fractionated by 6 percent polyacrylamide gel electrophoresis and 124 ng of ds cDNA greater than 600 base pairs in length was recovered by electroelution. A 20 ng portion of ds cDNA was extended with deoxy C residues using terminal deoxynucleotidyl transferase as described in Chang et al., *Nature* 275: 617 (1978) incorporated herein by reference, and annealed with 200 ng of the plasmid pBR322 (Bolivar et al., *Gene* 2: 95 (1977)) which had been cleaved with Pst I and tailed with deoxy G. Each annealed mixture was then transformed into *E. coli* K12 strain 294 (ATCC No. 31446). Approximately 8500 ampicillin sensitive, tetracycline resistant transformants were obtained.

E.1.3 Preparation of Synthetic Probes

The 14mer, 5' GGTGGGAAGATGGA 3' complementary to the coding sequence of constant region for mouse MOPC21 kappa chain which begins 25 basepairs 3' of the variable region DNA sequence was used as kappa chain probe. A 15 mer, 5' GACCAGGCATCCCAG 3', complementary to a coding sequence located 72 basepairs 3' of the variable region DNA sequence for mouse MOPC21 gamma chain was used to probe gamma chain gene.

Both probes were synthesized by the phosphotriester method described in German Offenlegungschrift 2644432, incorporated herein by reference, and made radioactive by kinasing as follows: 250 ng of deoxyoligonucleotide were combined in 25 μl of 60 mM Tris HCl (pH 8), 10 mM $MgCl_2$, 15 mM beta-mercaptoethanol, and 100 μCi ($\gamma$-$^{32}$P) ATP (Amersham, 5000 Ci/mMole). 5 units of T4 polynucleotide kinase were added and the reduction was allowed to proceed at 37° C. for 30 minutes and terminated by addition of EDTA to 20 mM.

E.1.4 Screening of Colony Library for Kappa or Gamma Chain Sequences

~2000 colonies prepared as described in paragraph E.1.2 were individually inoculated into wells of microtitre dishes containing LB (Miller, Experiments in Molecular Genetics, p. 431-3, Cold Spring Harbor, Lab., Cold Spring Harbor, N.Y. (1972))+5 μg/ml tetracycline and stored at −20° C. after addition of DMSO to 7 percent. Individual colonies from this library were transferred to duplicate sets of Schleicher and Schuell BA85/20 nitrocellulose filters and grown on agar plates containing LB+5 μg/ml tetracycline. After ~10 hours growth at 37° C. the colony filters were transferred to agar plates containing LB+5 μg/ml tetracycline and 12.5 μg/ml chloramphenicol and reincubated overnight at 37° C. The DNA from each colony was then denatured and fixed to the filter by a modification of the Grunstein-Hogness procedure as described in Grunstein et al., *Proc. Natl. Acad. Sci. (USA)* 72: 3961 (1975), incorporated herein by reference. Each filter was floated for 3 minutes on 0.5 N NaOH, 1.5 M NaCl to lyse the colonies and denature the DNA then neutralized by floating for 15 minutes on 3 M NaCl, 0.5 M Tris HCl (pH 7.5). The filters were then floated for an additional 15 minutes on 2XSSC, and subsequently baked for 2 hours in an 80° C. vacuum oven. The filters were prehybridized for ~2 hours at room temperature in 0.9 M NaCl, 1X Denhardts, 100 mM Tris HCl (pH 7.5), 5 mM Na-EDTA, 1 mM ATP, 1 M sodium phosphate (dibasic), 1 mM sodium pyrophosphate, 0.5 percent NP-40, and 200 μg/ml *E. coli* t-RNA, and hybridized in the same solution overnight, essentially as described by Wallace et al. *Nucleic Acids Research* 9: 879 (1981) using ~40×10$^6$ cpm of either the kinased kappa or gamma probe described above.

After extensive washing at 37° C. in 6X SSC, 0.1 percent SDS, the filters were exposed to Kodak XR-5 X-ray film with DuPont Lightning-Plus intensifying screens for 16–24 hours at −80° C. Approximately 20 colonies which hybridized with kappa chain probe and 20 which hybridized with gamma chain probe were characterized.

E.1.5 Characterization of Colonies which Hybridize to Kappa DNA Sequence Probe

Figure 2A:
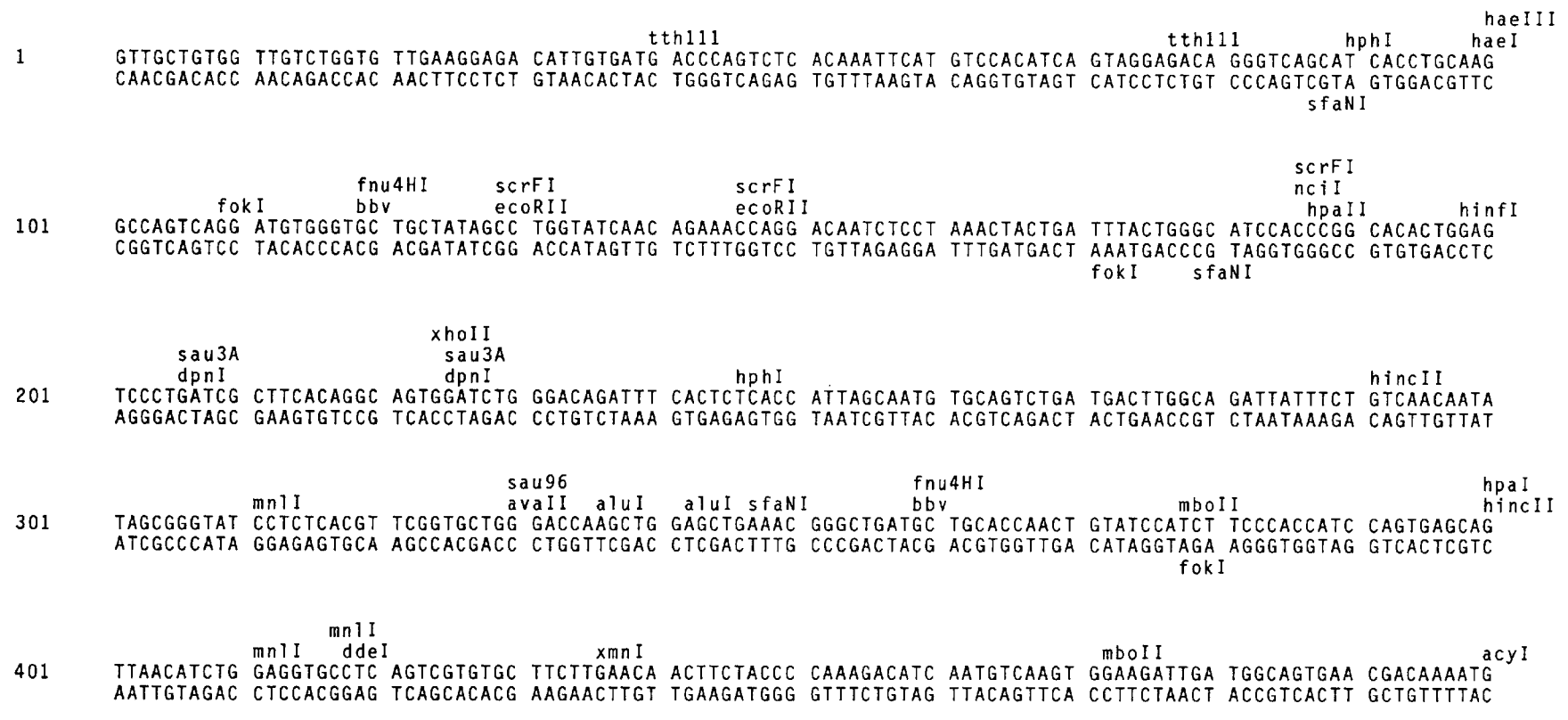

Plasmid DNAs isolated from several different transformants which hybridized to kappa chain probe were cleaved with Pst I and fractionated by polyacrylamide gel electrophoresis (PAGE). This analysis demonstrated that a number of plasmid DNAs contained cDNA inserts large enough to encode full length kappa chain. The complete nucleotide sequence of the cDNA insert of one of these plasmids was determined by the dideoxynucleotide chain termination method as described by Smith, *Methods Enzymol.* 65, 560 (1980) incorporated herein by reference after subcloning restriction endonuclease cleavage fragments into M13 vectors (Messing et al., *Nucleic Acids Research* 9: 309 (1981). FIG. 2 shows the nucleotide sequence of the cDNA insert of pK17G4 and FIG. 3 shows the gene sequence with the corresponding amino acid sequence. Thus, the entire coding region of mouse anti-CEA kappa chain was isolated on this one large DNA fragment. The amino acid sequence of kappa chain, deduced from the nucleotide sequence of the pK17G4 cDNA insert, corresponds perfectly with the first 23 N-terminal amino acids of mature mouse anti-CEA kappa chain as determined by amino acid sequence analysis of purified mouse anti-CEA kappa chain. The coding region of pK17G4 contains 27 basepairs or 9 amino acids of the presequence and 642 basepairs or 214 amino acids of the mature protein. The mature unglycosylated protein (MW 24,553) has a variable region of 119 amino acids, including the J1 joining region of 12 amino acids, and a constant region of 107 amino acids. After the stop codon behind amino acids 215 begins 212 basepairs of 3' untranslated sequence up to the polyA addition. The kappa chain probe used to identify pK17G4 hybridizes to nucleotides 374–388 (FIG. 2).

E.1.6 Characterization of Colonies which Hybridize to Gamma 1 DNA Probe

Plasmid DNA isolated from several transformants positive for hybridization with the heavy chain gamma 1 probe was subjected to Pst I restriction endonuclease analysis as described in E.1.5. Plasmid DNAs demonstrating the largest cDNA insert fragments were selected for further study. Nucleotide sequence coding for mouse heavy (gamma-1) chain, shows an NcoI restriction endonuclease cleavage site near the junction between variable and constant region. Selected plasmid DNAs were digested with both PstI and NcoI and sized on polyacrylamide. This analysis allowed identification of a number of plasmid DNAs that contain NcoI restriction endonuclease sites, although none that demonstrate cDNA insert fragments large enough to encode the entire coding region of mouse anti-CEA heavy chain.

In one plasmid isolated, p γ298 the cDNA insert of about 1300 bp contains sequence information for the 5' untranslated region, the signal sequence and the N-terminal portion of heavy chain. Because pγ298 did not encode the C-terminal sequence for mouse anti-CEA gamma 1 chain, plasmid DNA was isolated from other colonies and screened with PstI and NcoI. The C-terminal region of the cDNA insert of pγ11 was sequence and shown to contain the stop codon, 3' untranslated sequence and that portion of the coding sequence missing from p γ298.

FIG. 4 presents the entire nucleotide sequence of mouse anti-CEA heavy chain (as determined by the dideoxynucleotide chain termination method of Smith, *Methods Enzymol.*, 65: 560 (1980)) and FIG. 5 includes the translated sequence.

The amino acid sequence of gamma 1 (heavy chain) deduced from the nucleotide sequence of the pγ298 cDNA insert corresponds perfectly to the first 23 N-terminal amino acids of mature mouse anti-CEA gamma 1 chain as determined by amino acid sequence analysis of purified mouse anti-CEA gamma-1 chain. The coding region consists of 57 basepairs or 19 amino acids of presequences and 1346 basepairs or 447 amino acids of mature protein. The mature unglycosolated protein (MW 52,258) has a variable region of 135 amino acids, including a D region of 12 amino acids, and a J4 joining region of 13 amino acids. The constant region is 324 amino acids. After the stop codon behind amino acid 447 begins 96 bp of 3' untranslated sequences up to the polyA addition. The probe used to identify pγ298 and pγ11 hybridized to nucleotides 528–542 (FIG. 4).

E.1.7 Construction of a Plasmid for Direct Expression of Mouse Mature Anti-CEA Kappa Chain Gene, pKCEAtrp207-1*

Figure 6:
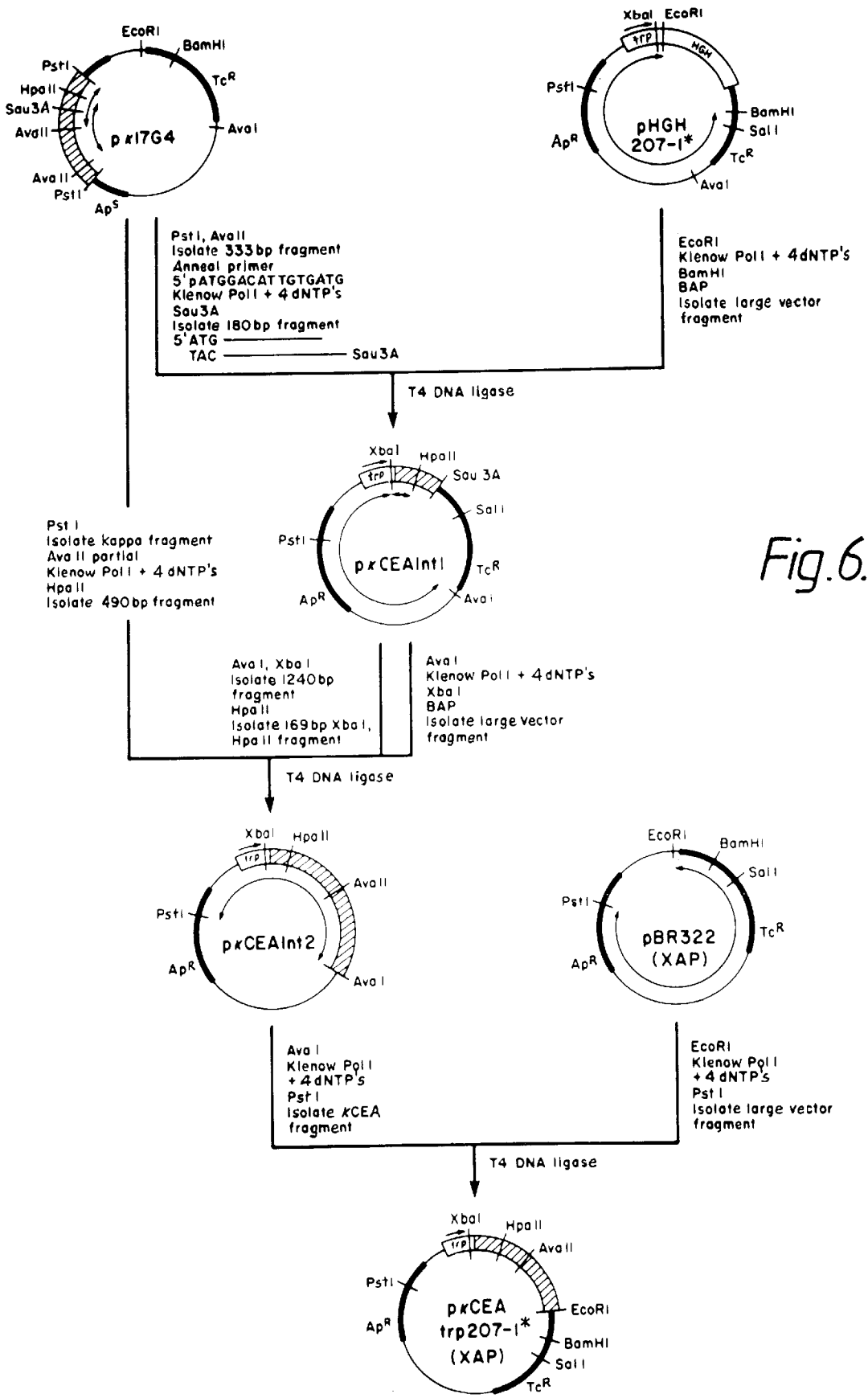
FIGS. 6 and 7 outline the construction of expression vectors for kappa and gamma anti-CEA chains respectively.

FIG. 6 illustrated the construction of pKCEAtrp207-1*

First, an intermediate plasmid pHGH207-1*, having a single trp promoter, was prepared as follows:

The plasmid pHGH 207 (described in U.S. patent application Ser. No. 307,473, filed Oct. 1, 1981 (EPO Publn. No. 0036776)) has a double lac promoter followed by the trp promoter, flanked by EcoR I sites and was used to prepare pHGH207-1. pHGH207 was digested with BamH 1, followed by partial digestion with EcoR I. The largest fragment, which contains the entire trp promoter, was isolated and ligated to the largest EcoR I- BamH I fragment from pBR322, and the ligation mixture used to transform *E. coli* 294. $Tet^R$ $Amp^R$ colonies were isolated, and most of them contained pHGH207-1. pHGH207-1* which lacks the EcoR1 site between the $amp^R$ gene and the trp promoter, was obtained by partial digestion of pHGH207-1 with EcoR I, filling in the ends with Klenow and dNTPs, and religation.

5 µg of pHGH207-1* was digested with EcoRI, and the ends extended to blunt ends using 12 units of DNA Polymerase I in a 50 µl reaction containing 60 mM NaCl, 7 mM $MgCl_2$, 7 mM Tris HCl (pH 7.4) and 1 mM in each dNTP at 37° C. for 1 hour, followed by extraction with phenol/$CHCl_3$ and precipitation with ethanol. The precipitated DNA was digested with BamH I, and the large vector fragment (fragment 1) purified using 5 percent polyacrylamide gel electrophoresis, electroelution, phenol/$CHCl_3$ extraction and ethanol precipitation.

The DNA was resuspended in 50 µl of 10 mM Tris pH 8, 1 mM EDTA and treated with 500 units Bacterial Alkaline Phosphatase (BAP) for 30' at 65° followed by phenol/$CHCl_3$ extraction and ethanol precipitation.

A DNA fragment containing part of the light chain sequence was prepared as follows: 7 µg of pH17G4 DNA was digested with Pst I and the kappa chain containing cDNA insert was isolated by 6 percent gel electrophoresis, and electroelution. After phenol/$CHCl_3$ extraction, ethanol precipitation and resuspension in water, this fragment was digested with Ava II. The 333 bp Pst I-Ava II DNA fragment was isolated and purified from a 6 percent polyacrylamide gel.

A 15 nucleotide DNA primer was synthesized by the phosphotriester method G. O. 2,644,432 (supra) and has the following sequence:

```
          Met Asp Ile Val Met
       5' ATG GAC ATT GTT ATG 3'
```

The 5' methionine serves as the initiation codon. 500 ng of this primer was phosphorylated at the 5' end with 10 units T4 DNA kinase in 20 µl reaction containing 0.5 mM ATP. ~200 ng of the Pst I-Ava II DNA fragment was mixed with the 20 µl of the phosphorylated primer, heated to 95° C. for 3 minutes and quick frozen in a dry-ice ethanol bath. The denatured DNA solution was made 60 mM NaCl, 7 mM $MgCl_2$, 7 mM Tris HCl (pH 7.4), 12 mM in each dNTP and 12 units DNA Polymerase I-Large Fragment was added. After 2 hours incubation at 37° C. this primer repair reaction was phenol/$CHCl_3$ extracted, ethanol precipitated, and digested to completion with Sau 3A. The reaction mixture was then electrophoresed on a 6 percent polyacrylamide gel and ~50 ng of the 182 basepair amino-terminal blunt-end to Sau 3A fragment (fragment 2) was obtained after electroelution.

100 ng of fragment 1 (supra) and 50 ng of fragment 2 were combined in 20 µl of 20 mM Tris HCl (pH 7.5), 10 mM $MgCl_2$, 10 mM DTT, 2.5 mM ATP and 1 unit of T4 DNA ligase. After overnight ligation at 14° C. the reaction was transformed into *E. coli* K12 strain 294. Restriction endonuclease digestion of plasmid DNA from a number of ampicillin resistant transformants indicated the proper construction and DNA sequence analysis proved the desired nucleotide sequence through the initiation codon of this new plasmid, pKCEAInt1 (FIG. 6).

The remainder of the coding sequence of the kappa light chain gene was prepared as follows:

The Pst I cDNA insert fragment from 7 µg of K17G4 DNA was partially digested with Ava II and the Ava II cohesive ends were extended to blunt ends in a DNA Polymerase I large fragment reaction. Following 6 percent polyacrylamide gel electrophoresis the 686 basepair Pst I to blunt ended Ava II DNA fragment was isolated, purified and subjected to Hpa II restriction endonuclease digestion. The 497 basepair Hpa II to blunt ended Ava II DNA fragment (fragment 3) was isolated and purified after gel electrophoresis.

10 µg of pKCEAInt1 DNA was digested with Ava I, extended with DNA polymerase I large fragment, and digested with Xba I. Both the large blunt ended Ava I to Xba I vector fragment and the small blunt ended Ava I to Xba I fragment were isolated and purified from a 6 percent polyacrylamide gel after electrophoresis. The large vector fragment (fragment 4) was treated with Bacterial Alkaline Phosphatase (BAP), and the small fragment was digested with Hpa II, electrophoresed on a 6 percent polyacrylamide and the 169 basepair Xba I-Hpa II DNA fragment (fragment 5) was purified. ~75 ng of fragment 4, ~50 ng of fragment 3 and ~50 ng of fragment 5 were combined in a T4 DNA ligase reaction and incubated overnight at 14°, and the reaction mixture transformed into E. coli K12 strain 294. Plasmid DNA from six ampicillin resistant transformants were analyzed by restriction endonuclease digestion. One plasmid DNA demonstrated the proper construction and was designated pKCEAInt2.

Final construction was effected by ligating the K-CEA fragment, including the trp promoter from pKCEAInt2 into pBR322(XAP). (pBR322(XAP) is prepared as described in U.S. application Ser. No. 452,227, filed Dec. 22, 1982; from pBR322 by deletion of the AvaI-PvuII fragment followed by ligation.)

The K-CEA fragment was prepared by treating pKCEAInt2 with Ava I, blunt ending with DNA polymerase I (Klenow fragment) in the presence of DNTPs, digestion with Pst I and isolation of the desired fragment by gel electrophoresis and electroelution.

The large vector fragment from pBR322(XAP) was prepared by successive treatment with EcoR I, blunt ending with polymerase, and redigestion with Pst I, followed by isolation of the large vector fragment by electrophoresis and electroelution.

The K-CEA and large vector fragments as prepared in the preceding paragraphs were ligated with T4 DNA ligase, and the ligation mixture transformed into E. coli as above. Plasmid DNA from several ampicillin resistant transformants were selected for analysis, and one plasmid DNA demonstrated the proper construction, and was designated pKCEAtrp207-I*.

E.1.8 Construction of a Plasmid Vector for Direct Expression of Mouse Mature Anti-CEA Heavy (Gamma 1) Chain Gene, pγCEAtrp207-1*

Figure 7:
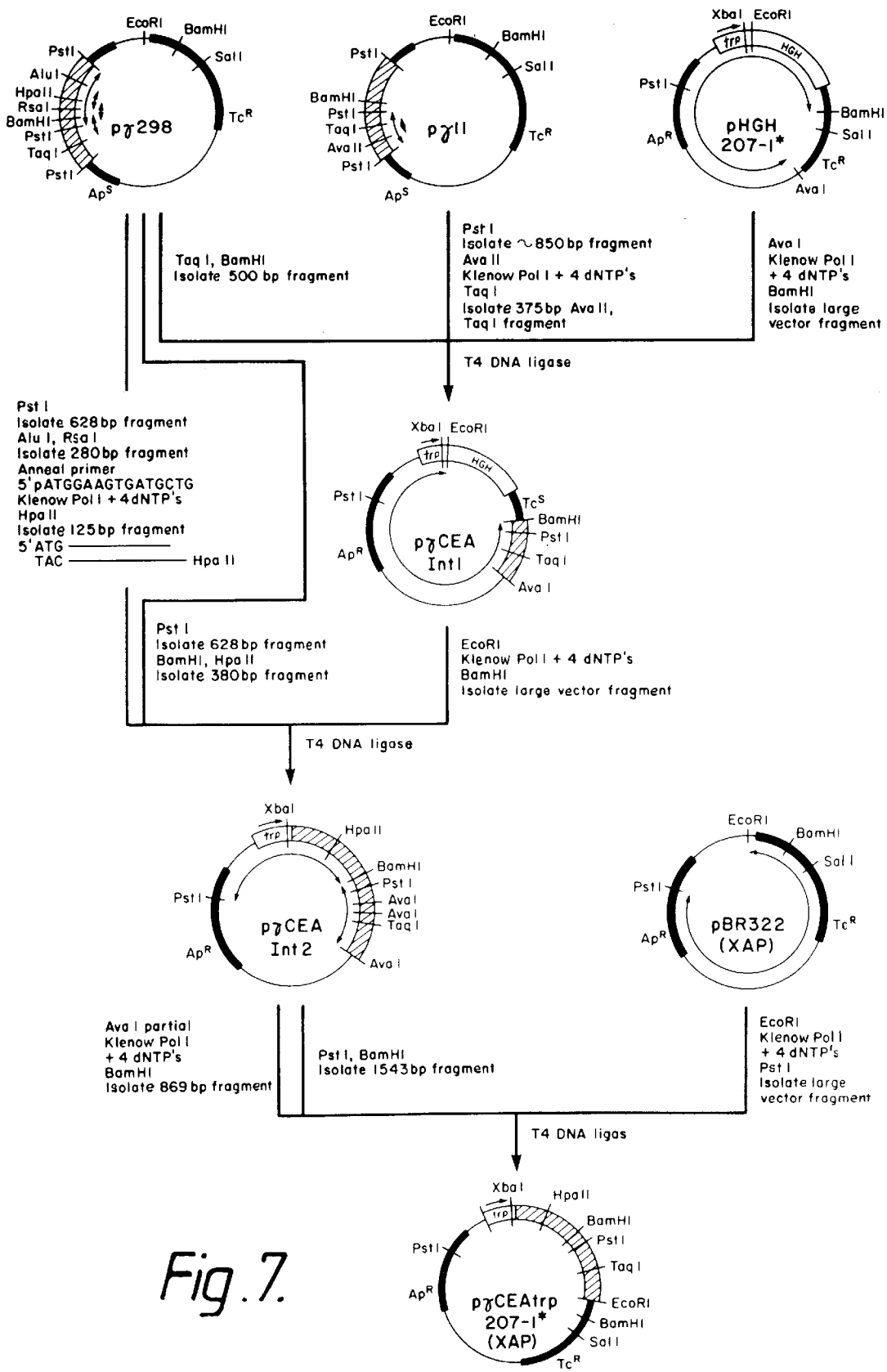

FIG. 7 illustrates the construction of pγCEAtrp207-1*. This plasmid was constructed in two parts beginning with construction of the C-terminal region of the gamma 1 gene.

5 μg of plasmid pHGH207-1* was digested with Ava I, extended to blunt ends with DNA polymerase I large fragment (Klenow fragment), extracted with phenol/CHCl$_3$, and ethanol precipitated. The DNA was digested with BamH I treated with BAP and the large fragment (fragment A) was purified by 6 percent polyacrylamide gel electrophoresis and electroelution.

~5 μg of pγ11 was digested with Pst I and the gamma chain cDNA insert fragment containing the C-terminal portion of the gene was purified, digested with Ava II followed by extension of the Ava II cohesive ends with Klenow, followed by Taq I digestion. The 375 basepair blunt ended Ava II to Taq I fragment (fragment B) was isolated and purified by gel electrophoresis and electroelution.

9 μg of pγ298 was digested with Taq I and BamH I for isolation of the 496 basepair fragment (fragment C).

Approximately equimolar amounts of fragments A, B, and C were ligated overnight at 14° in 20 μl reaction mixture, then transformed into E. coli strain 294. The plasmid DNA from six ampicillin resistant transformants was committed to restriction endonuclease analysis and one plasmid DNA, named pγCEAInt, demonstrated the correct construction of the C-terminal portion of gamma 1 (FIG. 5).

To obtain the N-terminal sequences, 30 μg of pγ298 was digested with Pst I and the 628 basepair DNA fragment encoding the N-terminal region of mouse anti-CEA gamma chain was isolated and purified. This fragment was further digested with Alu I and Rsa I for isolation of the 280 basepair fragment. A 15 nucleotide DNA primer

```
        met glu val met leu
     5' ATG GAA GTG ATG CTG 3'
``` was synthesized by the phosphotriester method (supra).

The 5' methionine serves as the initiation codon. 500 ng of this synthetic oligomer primer was phosphorylated at the 5' end in a reaction with 10 units T4 DNA kinase containing 0.5 mM ATP in 20 μl reaction mixture. ~500 ng of the 280 basepair Alu I-Rsa I DNA fragment was mixed with the phosphorylated primer. The mixture was heat denatured for 3 minutes at 95° and quenched in dry-ice ethanol. The denatured DNA solution was made 60 mM NaCl, 7 mM MgCl$_2$, 7 mM Tris HCl (pH 7.4), 12 mM in each dNTP and 12 units DNA Polymerase I-Large Fragment was added. After 2 hours incubation at 37° C., this primer repair reaction was phenol/CHCl$_3$ extracted, ethanol precipitated, and digested to completion with HpaII. ~50 ng of the expected 125 basepair blunt-end to Hpa II DNA fragment (fragment D) was purified from the gel.

A second aliquot of pγ298 DNA was digested with Pst I, the 628 basepair DNA fragment purified by polyacrylamide gel electrophoresis, and further digested with BamH I and Hpa II. The resulting 380 basepair fragment (fragment E) was purified by gel electrophoresis.

~5 μg of pγCEAIntI was digested with EcoR I, the cohesive ends were made flush with DNA polymerase I (Klenow), further digested with BamH I, treated with BAP and electrophoresed on a 6 percent polyacrylamide gel. The large vector fragment (fragment F) was isolated and purified.

In a three fragment ligation, 50 ng fragment D, 100 ng fragment E, and 100 ng fragment F were ligated overnight at 4° in a 20 μl reaction mixture and used to transform E. coli K12 strain 294. The plasmid DNAs from 12 ampicillin resistant transformants were analyzed for the correct construction and the nucleotide sequence surrounding the initiation codon was verified to be correct for the plasmid named pγCEAInt2.

The expression plasmid, pγCEAtrp207-I* used for expression of the heavy chain gene is prepared by a 3-way ligation using the large vector fragment from pBR322(XAP) (supra) and two fragments prepared from pγCEAInt2.

pBR322(XAP) was treated as above by digestion with EcoR1, blunt ending with DNA polymerase (Klenow) in the presence of dNTPs, followed by digestion with Pst I, and isolation of the large vector fragment by gel electrophoresis. A 1543 base pair fragment from pγCEAInt2 containing trp promoter linked with the N-terminal coding region of the heavy chain gene was isolated by treating pγCEAInt2 with Pst I followed by BamH I, and isolation of the desired fragment using PAGE. The 869 base pair fragment containing the C-terminal coding portion of the gene was prepared by partial digestion of pγCEAInt2 with Ava I, blunt ending with Klenow, and subsequent digestion with BamH I, followed by purification of the desired fragment by gel electrophoresis.

The aforementioned three fragments were then ligated under standard conditions using T4 DNA ligase, and a ligation mixture used to transform E. coli strain 294. Plasmid DNAs from several tetracycline resistant transformants were analyzed; one plasmid DNA demonstrated the proper construction and was designated pγCEAtrp207-1*.

E.1.9 Production of Immunoglobulin Chains by E. coli

E. coli strain W3110 (ATTC No. 27325) was transformed with pγCEAtrp207-1* or pKCEAtrp207-1* using standard techniques.

To obtain double transformants, E. coli strain W3110 cells were transformed with a modified pKCEAtrp207-1*, pKCEAtrp207-1*Δ, which had been modified by cleaving a Pst I-Pvu I fragment from the $amp^R$ gene and religating. Cells transformed with pKCEAtrp207-1*Δ are thus sensitive to ampicillin but still resistant to tetracycline. Successful transformants were retransformed using pγCEAInt2 which confers resistance to ampicillin but not tetracycline. Cells containing both pKCEAtrp207-1*Δ and pγCEAInt2 thus identified by growth in a medium containing both ampicillin and tetracycline.

To confirm the production of heavy and/or light chains in the transformed cells, the cell samples were inoculated into M9 tryptophan free medium containing 10 μg/ml tetracycline, and induced with indoleacrylic acid (IAA) when the OD 550 reads 0.5. The induced cells were grown at 37° C. during various time periods and then spun down, and suspended in TE buffer containing 2 percent SDS and 0.1 M β-mercaptoethanol and boiled for 5 minutes. A 10×volume of acetone was added and the cells kept at 22° C. for 10 minutes, then centrifuged at 12,000 rpm. The precipitate was suspended in O'Farrell SDS sample buffer (O'Farrell, P. H., J. Biol. Chem., 250: 4007 (1975)); boiled 3 minutes, recentrifuged, and fractionated using SDS PAGE (10 percent), and stained with silver stain (Goldman, D. et al., Science 211: 1437 (1981)); or subjected to Western blot using rabbit anti-mouse IgG (Burnett, W. N., et al., Anal. Biochem. 112: 195 (1981)), for identification light chain and heavy chain.

Cells transformed with pγCEAtrp207-1* showed bands upon SDS PAGE corresponding to heavy chain molecular weight as developed by silver stain. Cells transformed with pKCEAtrp207-1* showed the proper molecular weight band for light chain as identified by Western blot; double transformed cells showed bands for both heavy and light chain molecular weight proteins when developed using rabbit anti-mouse IgG by Western blot. These results are shown in FIGS. 8A, 8B, and 8C.

Figure 8A:
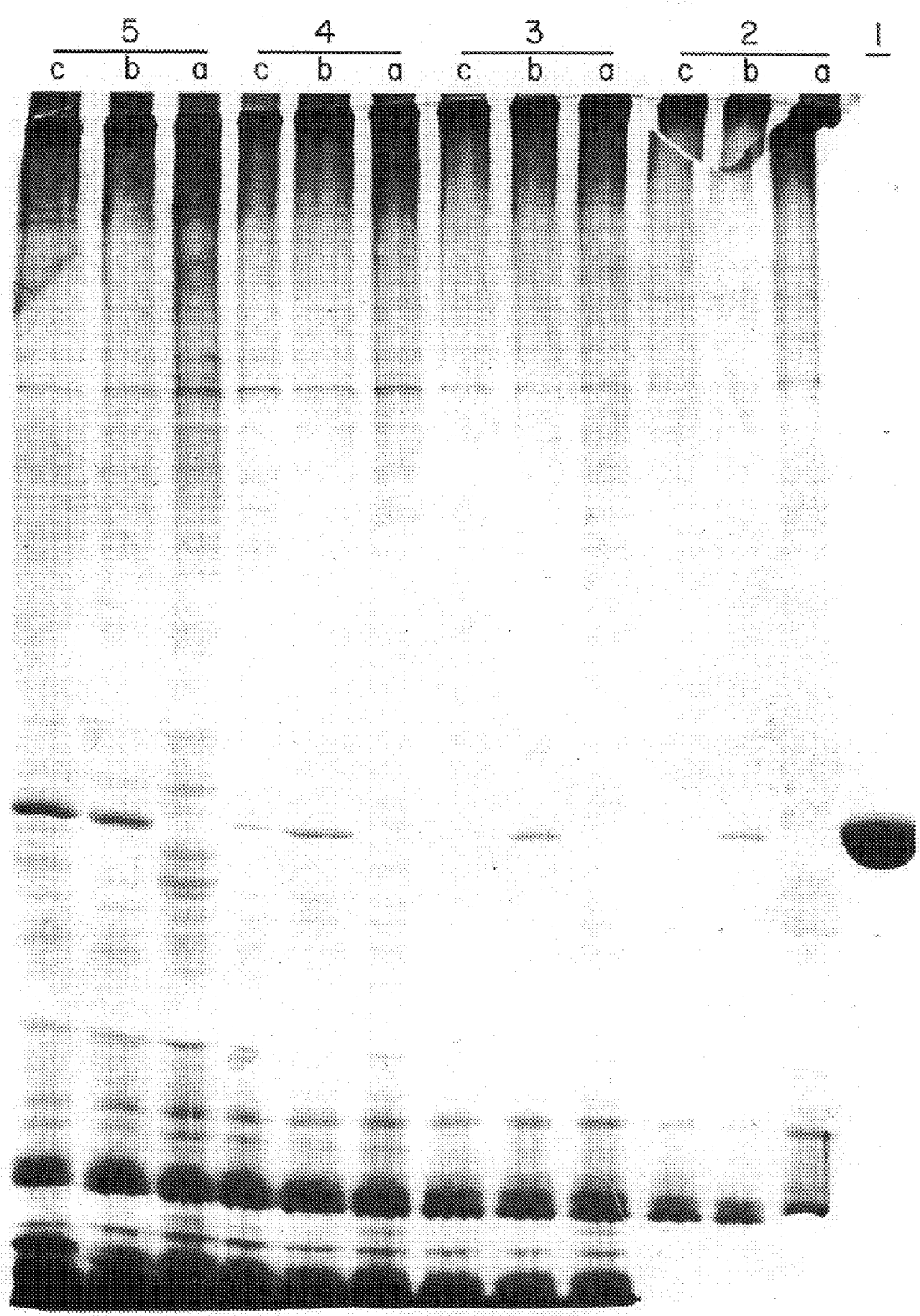
FIGS. 8A, 8B, and 8C show the results of sizing gels run on, extracts of *E. coli* expressing the genes for gamma chain, kappa chain, and both kappa and gamma chains respectively.

FIG. 8A shows results developed by silver stain from cells transformed with pγCEAtrp207-1*. Lane 1 is monoclonal anti-CEA heavy chain (standard) from CEA.66-E3. Lanes 2b–5b are timed samples 2 hrs, 4 hrs, 6 hrs, and 24 hrs after IAA addition. Lanes 2a–5a are corresponding untransformed controls; Lanes 2c–5c are corresponding uninduced transformants.

Figure 8B:
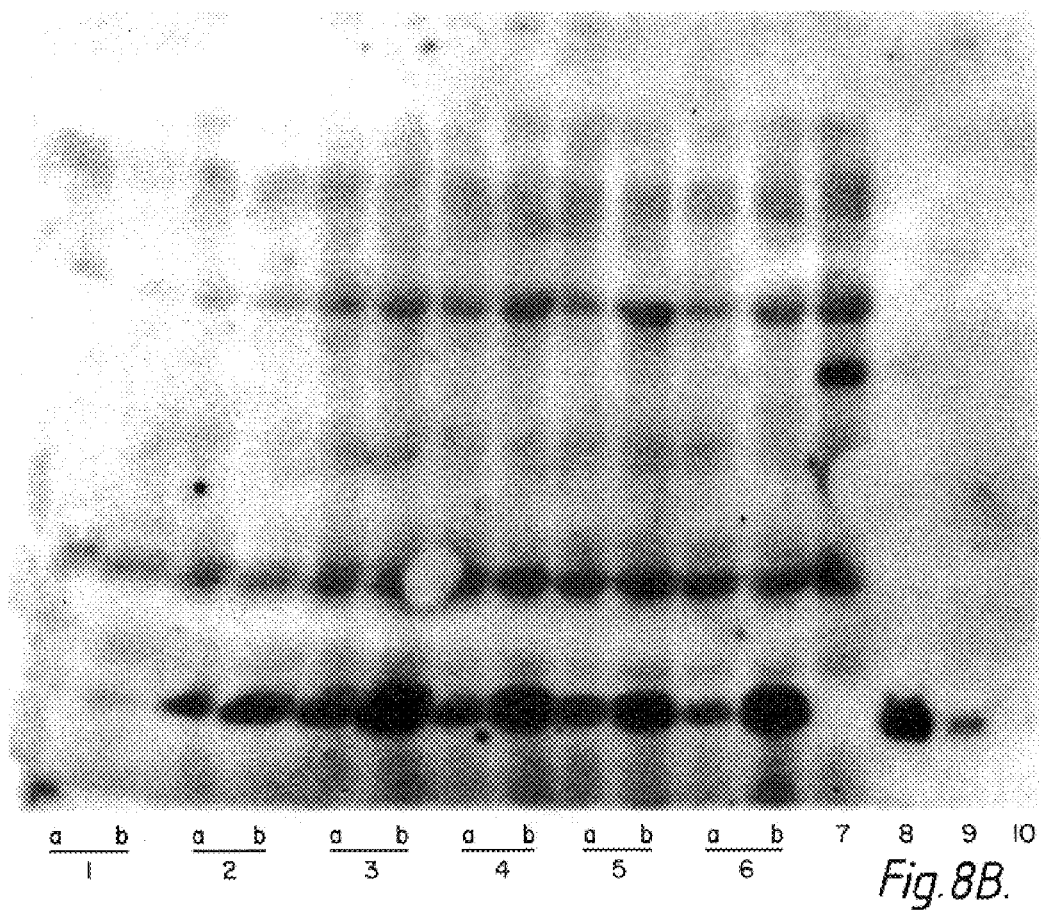

FIG. 8B shows results developed by Western blot from cells transformed with pKCEAtrp207-1*. Lanes 1b–6b are extracts from induced cell immediately, 1 hr, 3.5 hrs, 5 hrs, 8 hrs, and 24 hrs after IAA addition, and 1a–6a corresponding uninduced controls. Lane 7 is an extract from a pγCEAtrp207-1* control, lanes 8, 9, and 10 are varying amounts of anti CEA-kappa chain from CEA.66-E3 cells.

Figure 8C:
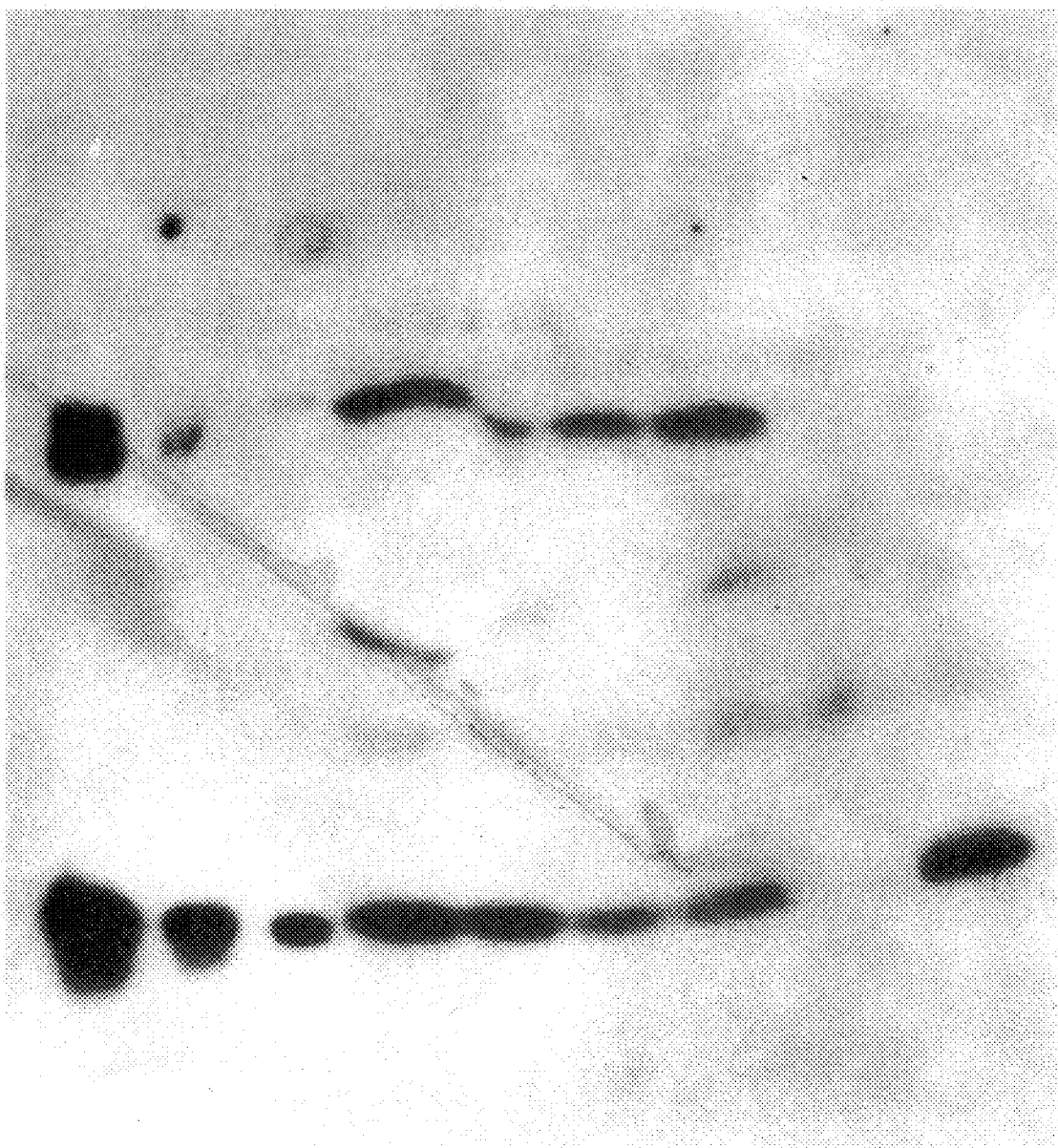

FIG. 8C shows results developed by Western blot from four colonies of double transformed cells 24 hours after IAA addition (lanes 4–7). Lanes 1–3 are varying amounts of monoclonal gamma chain controls, lanes 8 and 9 are untransformed and pγCEAtrp207-1* transformed cell extracts, respectively.

Figure 9:
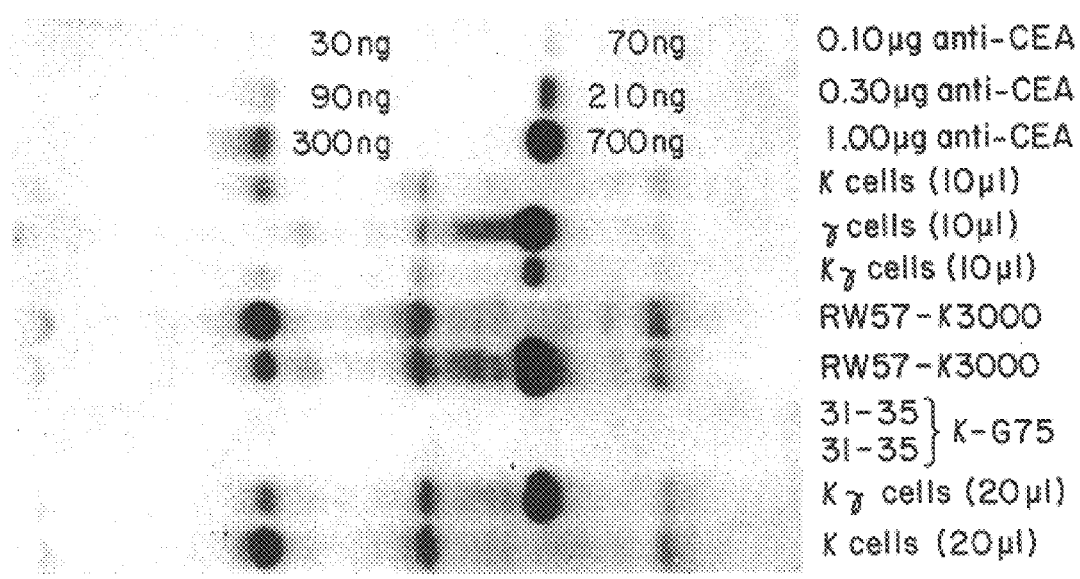
FIG. 9 shows the results of western blots of extracts of cells transformed as those in FIGS. 8.

In another quantitative assay, frozen, transformed E. coli cells grown according to E.1.10 (below) were lysed by heating in sodium dodecyl sulfate (SDS)/β-mercaptoethanol cell lysis buffer at 100°. Aliquots were loaded on an SDS polyacrylamide gel next to lanes loaded with various amounts of hybridoma anti-CEA. The gel was developed by the Western blot, Burnett (supra), using $^{125}$I-labeled sheep anti-mouse IgG antibody from New England Nuclear. The results are shown in FIG. 9. The figure shows that the E. coli products co-migrate with the authentic hybridoma chains, indicating no detectable proteolytic degradation in E. coli. Heavy chain from mammalian cells is expected to be slightly heavier than E. coli material due to glycosylation in the former. Using the hybridoma lanes as a standard, the following estimates of heavy and light chain production were made:

|  | (Per gram of cells) |
| --- | --- |
| E. coli (W3110/pγCEAtrp207-1*) | 5 mg γ |
| E. coli (W3110/pKCEAtrp207-1*) | 1.5 mg K |
| E. coli (W3110/pKCEAtrp207-1*Δ, pγCEAInt2) | 0.5 mg K, 1.0 mg γ |

E.1.10 Reconstitution of Antibody from Recombinant K and Gamma Chains

In order to obtain heavy and light chain preparations for reconstitution, transformed cells were grown in larger batches, harvested and frozen. Conditions of growth of the variously transformed cells were as follows:

E. coli (W3110/pγCEAtrp207-1*) were inoculated into 500 ml LB medium containing 5 μg/ml tetracycline and grown on a rotary shaker for 8 hours. The culture was then transferred to 10 liters of fermentation medium containing yeast nutrients, salts, glucose, and 2 μg/ml tetracycline. Additional glucose was added during growth and at OD 550=20, indoleacrylic (IAA), a trp derepressor, was added to a concentration of 50 μg/ml. The cells were fed additional glucose to a final OD 550=40, achieved approximately 6 hours from the IAA addition.

E. coli (W3110) cells transformed with pKCEA trp 207-1* and double transformed (with pKCEAtrp207-1*Δ and pγCEAInt2) were grown in a manner analogous to that described above except that the OD 550 six hours after IAA addition at harvest was 25–30.

The cells were then harvested by centrifugation, and frozen.

E.2 Assay Method for Reconstituted Antibody

Figure 10:
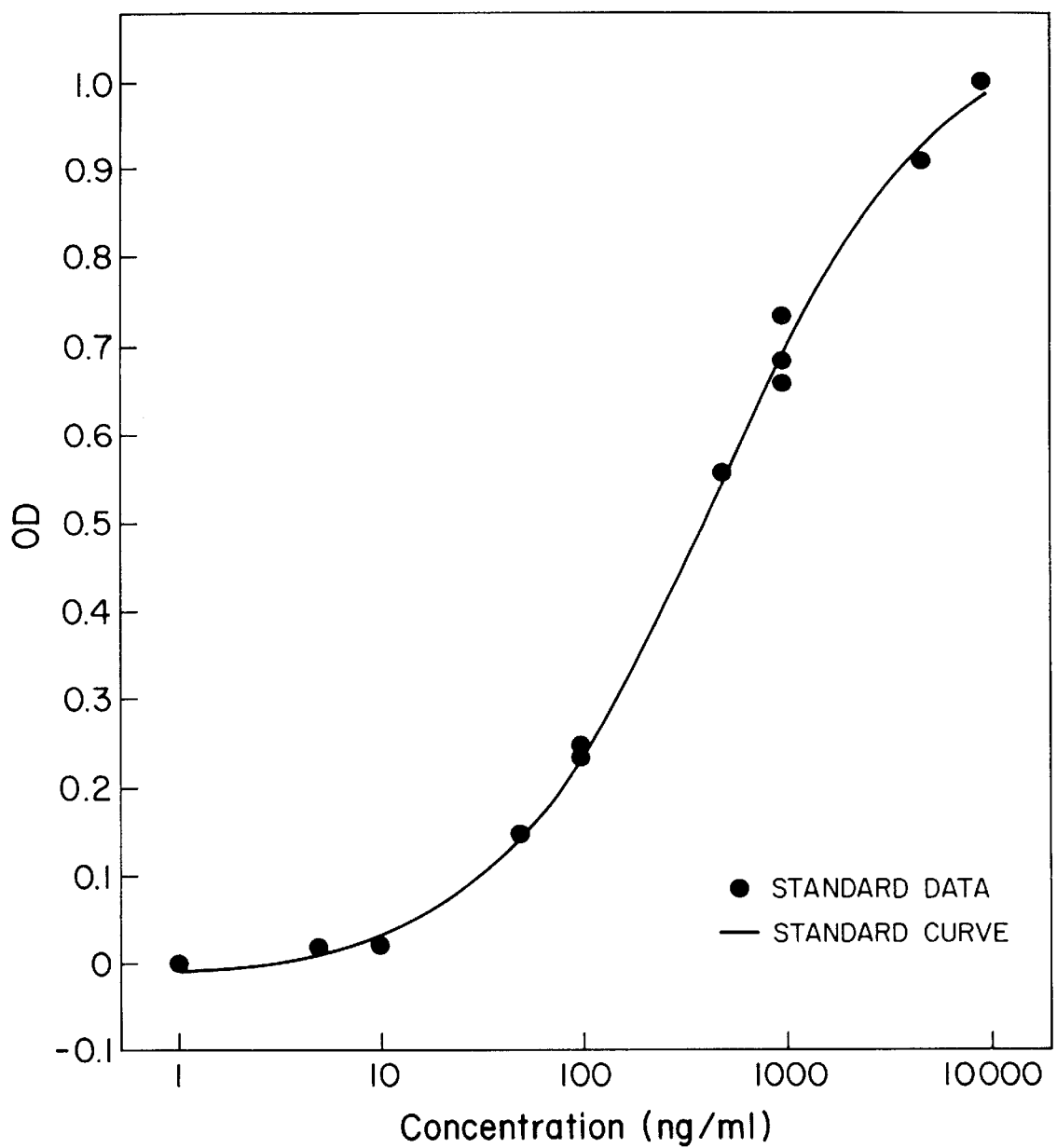
FIG. 10 shows a standard curve for ELISA assay of anti CEA activity.

Anti-CEA activity was determined by ELISA as a criterion for successful reconstitution. Wells of microtiter plates (Dynatech Immulon) were saturated with CEA by incubating 100 μl of 2–5 μg CEA/ml solution in 0.1M carbonate buffer, pH 9.3 for 12 hours at room temperature. The wells were then washed 4 times with phosphate buffered saline (PBS), and then saturated with BSA by incubating 200 μl of 0.5 percent BSA in PBS for 2 hours at 37° C., followed by washing 4 times with PBS. Fifty microliters of each sample was applied to each well. A standard curve (shown in FIG. 10), was run, which consisted of 50 μl samples of 10 μg, 5 μg, 1 μg, 500 ng, 100 ng, 50 ng, 10 ng, 5 ng and 1 ng anti-CEA/ml in 0.5 percent BSA in PBS, plus 50 μl of 0.5 percent BSA in PBS alone as a blank. All of the samples were incubated in the plate for 90 minutes at 37° C.

The plates were then washed 4 times with PBS, and sheep anti-mouse IgG-alkaline phosphate (TAGO, Inc.) was applied to each well by adding 100 μl of an enzyme concentration of 24 units/ml in 0.5 percent BSA in PBS. The solution was incubated at 37° C. for 90 minutes. The plates were washed 4 times with PBS before adding the substrate, 100 μl of a 0.4 mg/ml solution of p-nitrophenylphosphate (Sigma) in ethanolamine buffered saline, pH 9.5. The substrate was incubated 90 minutes at 37° C. for color development.

The $A_{450}$ of each well was read by the Microelisa Auto Reader (Dynatech) set to a threshold of 1.5, calibration of 1.0 and the 0.5 percent BSA in PBS (Blank) well set to 0.000. The $A_{450}$ data was tabulated in RS-1 on the VAX system, and the standard curve data fitted to a four-parameter logistic model. The unknown samples' concentration were calculated based on the $A_{450}$ data.

E.3 Reconstitution of Recombinant Antibody and Assay

Frozen cells prepared as described in paragraph E.1.10 were thawed in cold lysis buffer [10 mM Tris HCl, pH 7.5, 1 mM EDTA, 0.1M NaCl, 1 mM phenylmethylsulfonyl fluoride (PMSF)] and lysed by sonication. The lysate was partially clarified by centrifugation for 20 mins at 30,000 rpm. The supernatant was protected from proteolytic enzymes by an additional 1 mM PMSF, and used immediately or stored frozen at −80° C.; frozen lysates were never thawed more than once.

The S-sulfonate of E. coli produced anti-CEA heavy chain (γ) was prepared as follows: Recombinant E. coli cells transformed with pγCEAtrp207-1* which contained heavy chain as insoluble bodies, were lysed and centrifuged as above; the pellet was resuspended in the same buffer, sonicated and re-centrifuged. This pellet was washed once with buffer, then suspended in 6M guanidine HCl, 0.1M Tris HCl, pH 8, 1 mM EDTA, 20 mg/ml sodium sulfite and 10 mg/ml sodium tetrathionate and allowed to react at 25° for about 16 hrs. The reaction mixture was dialyzed against 8M urea, 0.1M Tris HCl, pH 8, and stored at 4°, to give a 3 mg/ml solution of γ-$SSO_3$.

650 μl of cell lysate from cells of various E. coli strains producing various IgG chains, was added to 500 mg urea. To this was added β-mercaptoethanol to 20 mM, Tris-HCl, pH 8.5 to 50 mM and EDTA to 1 mM, and in some experiments, γ-$SSO_3$ was added to 0.1 mg/ml. After standing at 25° for 30–90 mins., the reaction mixtures were dialyzed at 4° against a buffer composed of 0.1M sodium glycinate, pH 10.8, 0.5M urea, 10 mM glycine ethyl ester, 5 mM reduced glutathione, 0.1 mM oxidized glutathione. This buffer was prepared from $N_2$-saturated water and the dialysis was performed in a capped Wheaton bottle. After 16–48 hours, dialysis bags were transferred to 4° phosphate buffered saline containing 1 mM PMSF and dialysis continued another 16–24 hrs. Dialysates were assayed by ELISA as described in paragraph E.2 for ability to bind CEA. The results below show the values obtained by comparison with the standard curve in x ng/ml anti-CEA. Also shown are the reconstitution efficiencies calculated from the ELISA responses, minus the background (108 ng/ml) of cells producing K chain only, and from estimates of the levels of γ and K chains in the reaction mixtures.

|  | ng/ml anti-CEA | Percent recombination |
| --- | --- | --- |
| E. coli W3110 producing IFN-αA (control) | 0 | — |
| E. coli (W3110/pKCEAtrp207-1*) | 108 | — |
| E. coli (W3110/pKCEAtrp207-1*), plus γ-$SSO_3$ | 848 | 0.33 |
| E. coli (W3110/pKCEAtrp207-1*Δ, pγCEAInt2) | 1580 | 0.76 |
| Hybridoma anti-CEA K-$SSO_3$ and γ-$SSO_3$ | 540 | 0.40 |

E.4 Preparation of Chimeric Antibody

Figure 11:
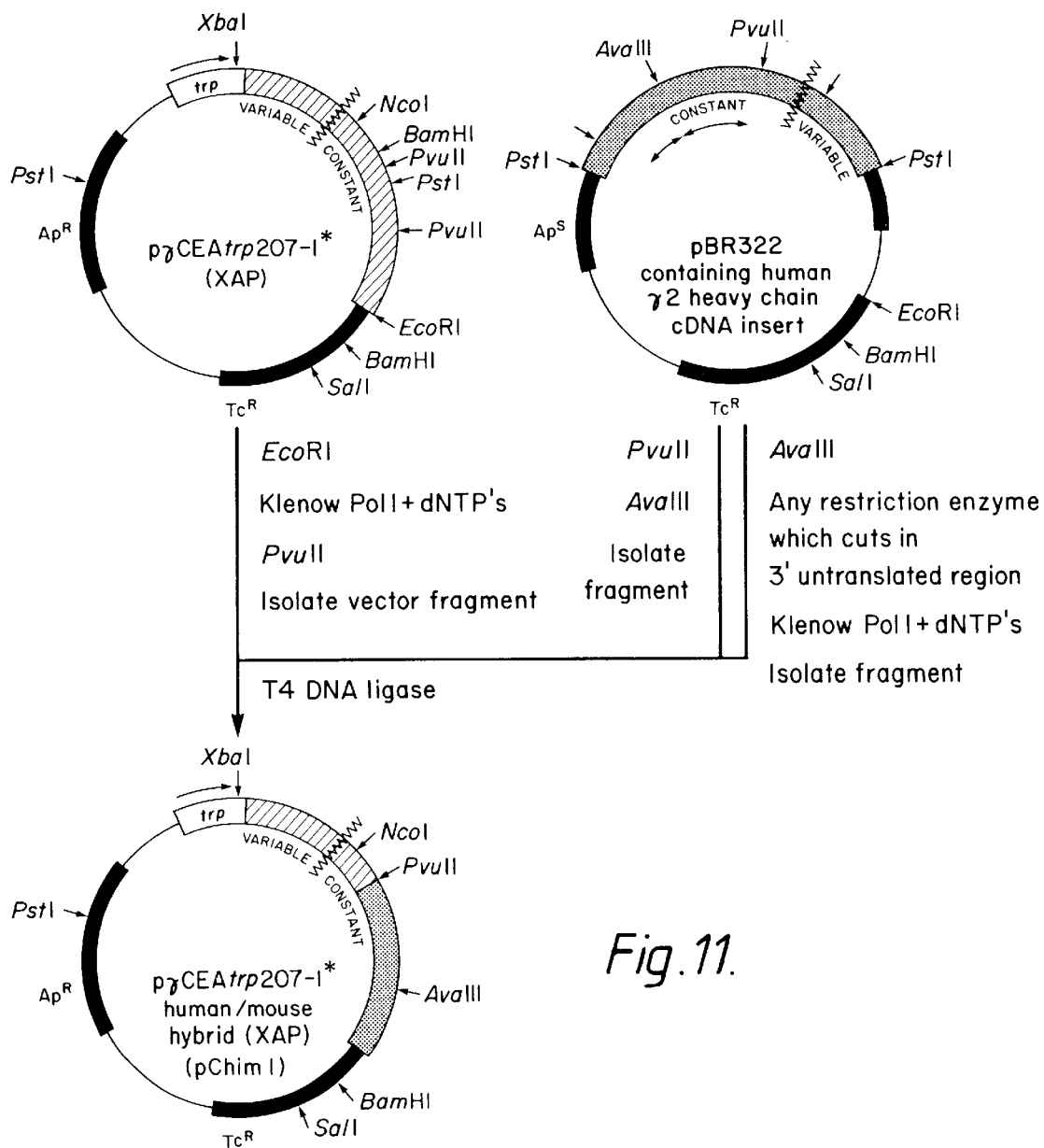
FIGS. 11 and 12 show the construction of a plasmid for expression of the gene encoding a chimeric heavy chain.
Figure 12:
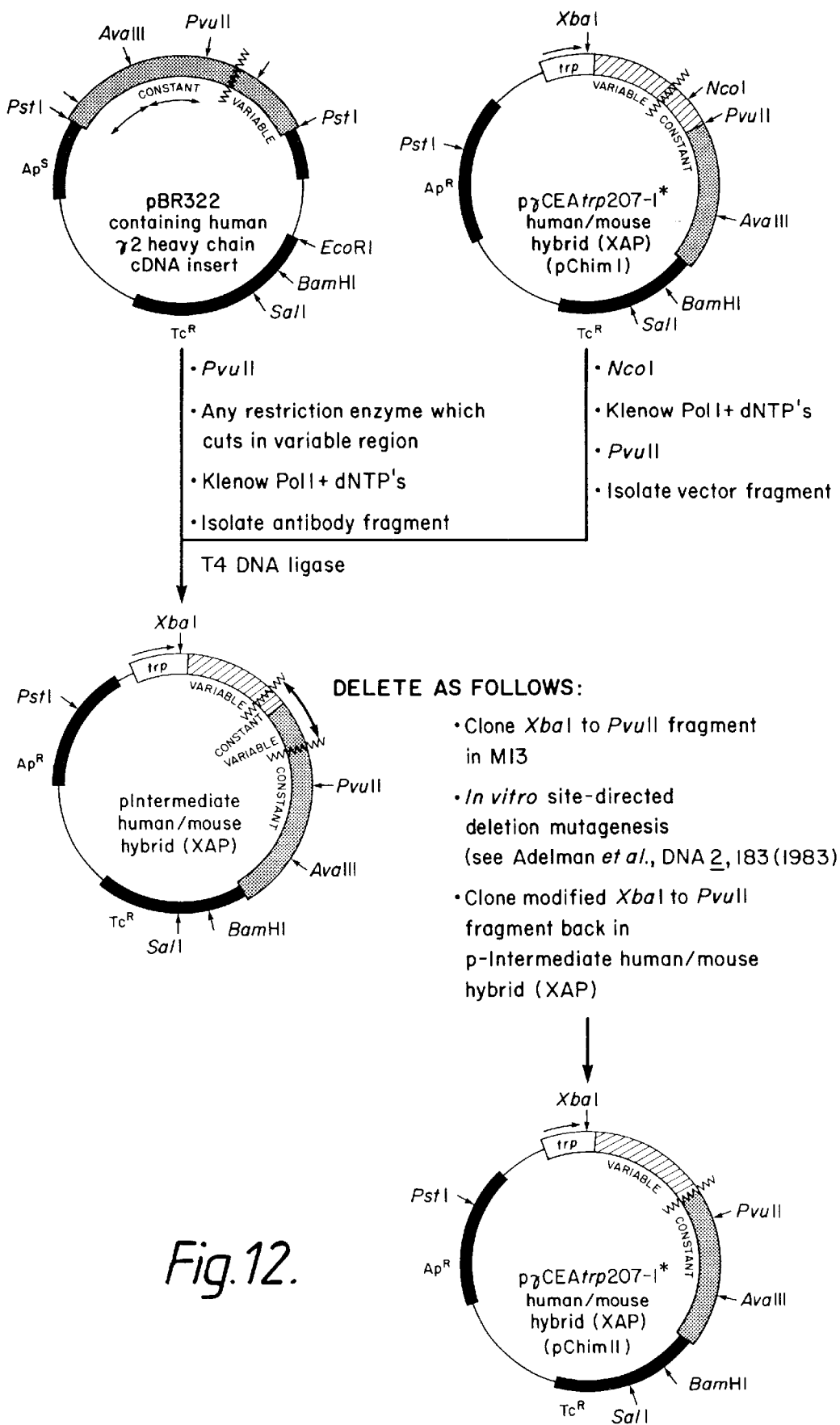

FIGS. 11 and 12 show the construction of an expression vector for a chimeric heavy (gamma) chain which comprises the murine anti CEA variable region and human γ-2 constant region.

A DNA sequence encoding the human gamma-2 heavy chain is prepared as follows: the cDNA library obtained by standard techniques from a human multiple myeloma cell line is probed with 5' GGGCACTCGACACAA 3' to obtain the plasmid containing the cDNA insert for human gamma-2 chain (Takahashi, et al., Cell, 29: 671 (1982), incorporated herein by reference), and analyzed to verify its identity with the known sequence in human gamma-2 (Ellison, J., et al., Proc. Natl. Acad. Sci. (USA), 79: 1984 (1982) incorporated herein by reference).

As shown in FIG. 11, two fragments are obtained from this cloned human gamma 2 plasmid (pγ2). The first fragment is formed by digestion with PvuII followed by digestion with Ava III, and purification of the smaller DNA fragment, which contains a portion of the constant region, using 6 percent PAGE. The second fragment is obtained by digesting the pγ2 with any restriction enzyme which cleaves in the 3' untranslated region of γ2, as deduced from the nucleotide sequence, filling in the Klenow and dNTPs, cleaving with Ava III, and isolating the smaller fragment using 6 percent PAGE. (The choice of a two step, two fragment composition to supply the PvuII-3' untranslated fragment provides a cleaner path to product due to the proximity of the AvaIII site to the 3 terminal end thus avoiding additional restriction sites in the gene sequence matching the 3' untranslated region site.) pγCEA207-1* is digested with EcoR 1, treated with Klenow and dNTPs to fill in the cohesive end, and digested with Pvu II, the large vector fragment containing promoter isolated by 6 percent PAGE.

The location and DNA sequence surrounding the PvuII site in the mouse gamma-1 gene are identical to the location and DNA sequence surrounding the PvuII site in the human gamma-2 gene.

The plasmid resulting from a three way ligation of the foregoing fragments, pChim1, contains, under the influence of trp promoter, the variable and part of the constant region of murine anti-CEA gamma 1 chain, and a portion of the gamma 2 human chain. pChim1 will, in fact, express a chimeric heavy chain when transformed into E. coli, but one wherein the change from mouse to human does not take place at the variable to constant junction.

FIG. 12 shows modification of pChim1 to construct pChim2 so that the resulting protein from expression will contain variable region from murine anti CEA antibody and constant region from the human γ-2 chain. First, a fragment is prepared from pChim1 by treating with Nco I, blunt ending with Klenow and dNTPs, cleaving with Pvu II, and isolating the large vector fragment which is almost the complete plasmid except for short segment in the constant coding region for mouse anti CEA. A second fragment is prepared from the previously described pγ2 by treating with Pvu II, followed by treating with any restriction enzyme which cleaves in the variable region, blunt ending with Klenow and dNTPs and isolating the short fragment which comprises the junction between variable and constant regions of this chain.

Ligation of the foregoing two fragments produces an intermediate plasmid which is correct except for an extraneous DNA fragment which contains a small portion of the constant region of the murine anti CEA antigen, and a small portion of the variable region of the human gamma chain. This repair can be made by excising the Xba I to Pvu II fragment and cloning into M13 phage as described by Messing et al., Nucleic Acids Res. 9: 309 (1981), followed by in vitro site directed deletion mutagenesis as described by Adelman, et al., DNA, in press (1983) which is incorporated herein by reference. The Xba I-Pvu II fragment thus modified is ligated back into the intermediate plasmid to form pChim2. This plasmid then is capable of expressing in a suitable host a cleanly constructed murine variable/human constant chimeric heavy chain.

In an analogous fashion, but using mRNA templates for cDNA construction for human kappa rather than γ chain, the expression plasmid for chimeric light chain is prepared.

The foregoing two plasmids are then double transformed into *E. coli* W3110, the cells grown and the chains reconstituted as set forth in paragraph E.1–E.3 supra.

E.5 Preparation of Altered Murine Anti-CEA Antibody

E.5.1 Construction of Plasmid Vectors for Direct Expression of Altered Murine Anti-CEA Heavy Chain Gene The cysteine residues, and the resultant disulfide bonds in the region of amino acids 216–230 in the constant region of murine anti-CEA heavy chain are suspected to be important for complement fixation (Klein, et al., *Proc. Natl. Acad. Sci., (USA)*, 78: 524 (1981)) but not for the antigen binding property of the resulting antibody. To decrease the probability of incorrect disulfide bond formation during reconstitution according to the process of the invention herein, the nucleotides encoding the amino acid residues 226–232 which includes codons for three cysteines, are deleted as follows:

A "deleter" deoxyoligonucelotide, 5' CTAACACCATGT-CAGGGT is used to delete the relevant portions of the gene from pγCEAtrp207-1* by the procedure of Wallace, et al., *Science*, 209: 1396 (1980) or of Adelman, et al., *DNA* 2, 183 (1983). Briefly, the "deleter" deoxyoligonucelotide is annealed with denatured pγCEAtrp207-1* DNA, and primer repair synthesis carried out in vitro, followed by screening by hybridization of presumptive deletion clones with P³² labelled deleter sequence.

E.5.2 Production of Cysteine Deficient Altered Antibody

The plasmid prepared in E.5.1 is transformed into an *E. coli* strain previously transformed with pKCEAtrp207-1* as described above. The cells are grown, extracted for recombinant antibody chains, and the altered antibody reconstituted as described in E.1.10.

E.6 Preparation of Fab

E.6.1 Construction of a Plasmid Vector for Direct Expression of Murine Anti-CEA Gamma 1 Fab Fragment Gene pγCEAFabtrp207-1*

Figure 13:
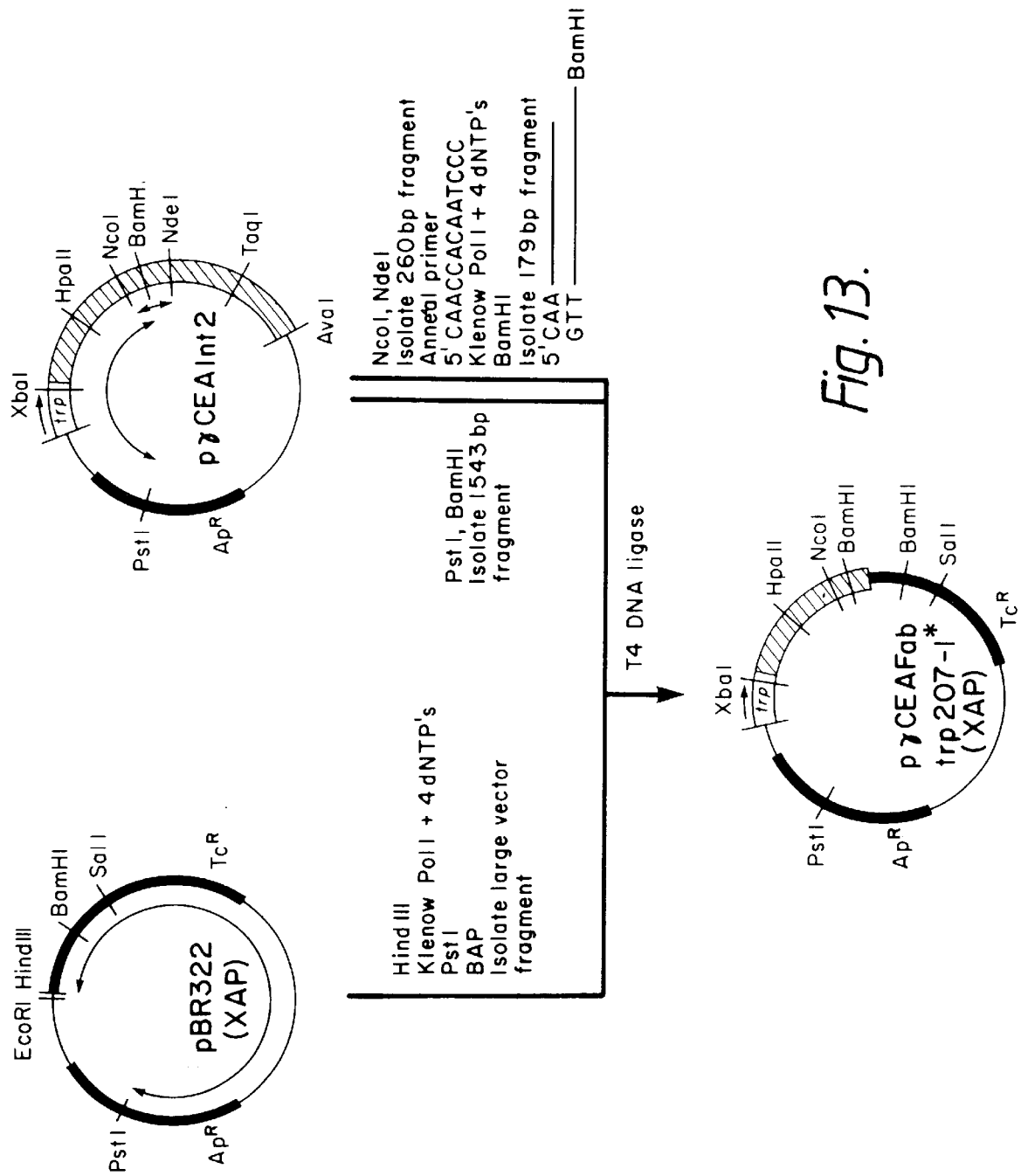
FIG. 13 shows the construction of a plasmid for expression of the gene encoding the Fab region of heavy chain.

FIG. 13 presents the construction of pγCEAFabtrp207-1*. 5 μg of pBR322 was digested with Hind III, the cohesive ends made flush by treating with Klenow and dNTPs; digested with Pst I, and treated with BAP. The large vector fragment, fragment I, was recovered using 6 percent PAGE followed by electroelution.

5 μg of pγCEAtrp207-1* was digested with both BamH I and Pst I and the ~1570 bp DNA fragment (fragment II) containing the trp promoter and the gene sequence encoding the variable region continuing into constant region and further into the anti-CEA gamma 1 chain hinge region, was isolated and purified after electrophoresis.

Expression of the anti-CEA gamma 1 chain Fab fragment rather than complete heavy chain requires that a termination codon be constructed at the appropriate location in the gene. For this, the 260 bp Nco I-Nde I DNA fragment from 20 μg of the pγ298 was isolated and purified. A 13 nucleotide DNA primer, the complement of which encodes the last 3 C-terminal amino acids of the Fab gene and 2 bases of the 3 needed for the stop codon, was synthesized by the phosphotriester method (supra). The probe hybridizes to nucleotides 754 to 767 (FIG. 4) which has the following sequence:

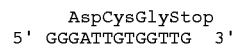

```
          AspCysGlyStop
5' GGGATTGTGGTTG 3'
```

The third base of the stop codon is provided by the terminal nucleotide of the filled-in Hind III site from pBR322 cleavage described above. 500 ng of this primer was used in a primer repair reaction by phosphorylation at the 5' end in a reaction with 10 units T4 DNA kinase containing 0.5 mM ATP in 20 μl, and mixing with ~200 ng of the Nco I-Nde I DNA fragment. The mixture was heat denatured for 3 minutes at 95° and quenched in dry-ice ethanol. The denatured DNA solution was made 60 mM NaCl, 7 mM MgCl₂, 7 mM Tris HCl (pH 7.4), 12 mM in each dNTP and 12 units DNA Polymerase I-Large Fragment was added. After 2 hours incubation at 37° C., this primer repair reaction was phenol/CHCl₃ extracted, ethanol precipitated, digested with BamH I and the reaction electrophoresed through a 6 percent polyacrylamide gel. ~50 ng of the 181 bp blunt end to BamH I DNA fragment, fragment III, was isolated and purified.

~100 ng of fragment I, ~100 ng each of fragments II and III were ligated overnight and transformed into *E. coli* K12 strain 294. Plasmid DNA from several tetracycline resistant transformants was analyzed for the proper construction and the nucleotide sequence through the repair blunt end filled-in Hind III junction was determined for verification of the TGA stop codon.

E.6.2 Production of Fab Protein

The plasmid prepared in E.6.1 is transformed into an *E. coli* strain previously transformed with pKCEAtrp207-1* as described above. The cells are grown, extracted for recombinant antibody chains and the Fab protein reconstituted as described in E.1.10.

What is claimed is:

1. A process for producing an immunoglobulin molecule or an immunologically functional immunoglobulin fragment comprising at least the variable domains of the immunoglobulin heavy and light chains, in a single host cell, comprising the steps of:
   (i) transforming said single host cell with a first DNA sequence encoding at least the variable domain of the immunoglobulin heavy chain and a second DNA sequence encoding at least the variable domain of the immunoglobulin light chain, and
   (ii) independently expressing said first DNA sequence and said second DNA sequence so that said immunoglobulin heavy and light chains are produced as separate molecules in said transformed single host cell.

2. The process according to claim 1 wherein said first and second DNA sequences are present in different vectors.

3. The process according to claim 1 wherein said first and second DNA sequences are present in a single vector.

4. A process according to claim 3 wherein the vector is a plasmid.

5. The process according to claim 4 wherein the plasmid is pBR322.

6. The process according to claim 1 wherein the host cell is a bacterium or yeast.

7. The process according to claim 6 wherein the host cell is *E. coli* or *S. cerevisiae*.

8. A process according to claim 7 wherein the host cell is *E. coli* strain X1776 (ATCC No. 31537).

9. A process according to claim 1 wherein the immunoglobulin heavy and light chains are expressed in the host cell and secreted therefrom as an immunologically functional immunoglobulin molecule or immunoglobulin fragment.

10. A process according to claim 1 wherein the immunoglobulin heavy and light chains are produced in insoluble form and are solubilized and allowed to refold in solution to form an immunologically functional immunoglobulin molecule or immunoglobulin fragment.

11. A process according to claim 1 wherein the DNA sequences code for the complete immunoglobulin heavy and light chains.

12. The process according to claim 1 wherein said first or said second DNA sequence further encodes at least one constant domain, wherein the constant domain is derived from the same source as the variable domain to which it is attached.

13. The process according to claim 1 wherein said first or said second DNA sequence further encodes at least one constant domain, wherein the constant domain is derived from a species or class different from that from which the variable domain to which it is attached is derived.

14. The process according to claim 1 wherein said first and second DNA sequences are derived from one or more monoclonal antibody producing hybridomas.

15. A vector comprising a first DNA sequence encoding at least a variable domain of an immunoglobulin heavy chain and a second DNA sequence encoding at least a variable domain of an immunoglobulin light chain wherein said first DNA sequence and said second DNA sequence are located in said vector at different insertion sites.

16. A vector according to claim 15 which is a plasmid.

17. A host cell transformed with a vector according to claim 15.

18. A transformed host cell comprising at least two vectors, at least one of said vectors comprising a DNA sequence encoding at least a variable domain of an immunoglobulin heavy chain and at least another one of said vectors comprising a DNA sequence encoding at least the variable domain of an immunoglobulin light chain.

19. The process of claim 1 wherein the host cell is a mammalian cell.

20. The transformed host cell of claim 18 wherein the host cell is a mammalian cell.

21. A method comprising
 a) preparing a DNA sequence consisting essentially of DNA encoding an immunoglobulin consisting of an immunoglobulin heavy chain and light chain or Fab region, said immunoglobulin having specificity for a particular known antigen;
 b) inserting the DNA sequence of step a) into a replicable expression vector operably linked to a suitable promoter;
 c) transforming a prokaryotic or eukaryotic microbial host cell culture with the vector of step b);
 d) culturing the host cell; and
 e) recovering the immunoglobulin from the host cell culture, said immunoglobulin being capable of binding to a known antigen.

22. The method of claim 21 wherein the heavy and light chain are the heavy and light chains of anti-CEA antibody.

23. The method of claim 21 wherein the heavy chain is of the gamma family.

24. The method of claim 21 wherein the light chain is of the kappa family.

25. The method of claim 21 wherein the vector contains DNA encoding both a heavy chain and a light chain.

26. The method of claim 21 wherein the host cell is *E. coli* or yeast.

27. The method of claim 26 wherein the heavy chain and light chains or Fab region are deposited within the cells as insoluble particles.

28. The method of claim 27 wherein the heavy and light chains are recovered from the particles by cell lysis followed by solubilization in denaturant.

29. The method of claim 21 wherein the heavy and light chains are secreted into the medium.

30. The method of claim 21 wherein the host cell is a gram negative bacterium and the heavy and light chains are secreted into the periplasmic space of the host cell bacterium.

31. The method of claim 21 further comprising recovering both heavy and light chain and reconstituting light chain and heavy chain to form an immunoglobulin having specific affinity for a particular known antigen.

32. The insoluble particles of heavy chain and light chains or Fab region produced by the method of claim 27.

33. A process for producing an immunoglobulin molecule or an immunologically functional immunoglobulin fragment comprising at least the variable domains of the immunoglobulin heavy and light chains, in a single host cell, comprising:
 independently expressing a first DNA sequence encoding at least the variable domain of the immunoglobulin heavy chain and a second DNA sequence encoding at least the variable domain of the immunoglobulin light chain so that said immunoglobulin heavy and light chains are produced as separate molecules in said single host cell transformed with said first and second DNA sequences.

34. The process of claim 9, further comprising the step of attaching the immunoglobulin molecule or immunoglobulin fragment to a label or drug.

35. The process of claim 10, further comprising the step of attaching the immunoglobulin molecule or immunoglobulin fragment to a label or drug.

36. The process of claim 33, further comprising the step of attaching the immunoglobulin molecule or immunoglobulin fragment to a label or drug.

* * * * *

UNITED STATES PATENT AND TRADEMARK OFFICE
CERTIFICATE OF CORRECTION

PATENT NO.   : 6,331,415 B1
DATED        : December 18, 2001
INVENTOR(S)  : Shmuel Cabilly et al.

It is certified that error appears in the above-identified patent and that said Letters Patent is hereby corrected as shown below:

<u>Title page,</u>
Item [73], Assignee, please insert -- City of Hope, Duarte, CA (US) --.

<u>Column 19,</u>
Line 56, please change "BamH 1" to -- BamH I --.

Signed and Sealed this

Twenty-fifth Day of June, 2002

Attest:

Attesting Officer

JAMES E. ROGAN
Director of the United States Patent and Trademark Office

(12) EX PARTE REEXAMINATION CERTIFICATE (6829th)
United States Patent
Cabilly et al.

(10) Number: US 6,331,415 C1
(45) Certificate Issued: May 19, 2009

(54) METHODS OF PRODUCING IMMUNOGLOBULINS, VECTORS AND TRANSFORMED HOST CELLS FOR USE THEREIN

(75) Inventors: Shmuel Cabilly, Monrovia, CA (US); Herbert L. Heyneker, Burlingame, CA (US); William E. Holmes, Pacifica, CA (US); Arthur D. Riggs, La Verne, CA (US); Ronald B. Wetzel, San Francisco, CA (US)

(73) Assignees: Genentech, Inc., South San Francisco, CA (US); City of Hope, Duarte, CA (US)

Reexamination Request:
No. 90/007,542, May 13, 2005
No. 90/007,859, Dec. 23, 2005

Reexamination Certificate for:
Patent No.: 6,331,415
Issued: Dec. 18, 2001
Appl. No.: 07/205,419
Filed: Jun. 10, 1988

Certificate of Correction issued Jun. 25, 2002.

Related U.S. Application Data

(63) Continuation of application No. 06/483,457, filed on Apr. 8, 1983, now Pat. No. 4,816,567.

(51) Int. Cl.
*C12N 15/13* (2006.01)
*C12N 15/00* (2006.01)
*C12N 15/63* (2006.01)

(52) U.S. Cl. .................. 435/69.6; 435/252.1; 435/252.3; 435/252.33; 435/254.11; 435/254.2; 435/254.21; 435/69.7; 435/70.21; 435/71.2; 435/71.1; 435/70.1; 435/320.1; 435/455; 435/483; 435/485; 435/471; 435/69.1

(58) Field of Classification Search .................. None
See application file for complete search history.

(56) References Cited

U.S. PATENT DOCUMENTS

| | | | |
|---|---|---|---|
| 4,224,404 A | 9/1980 | Viza | |
| 4,348,376 A | 9/1982 | Goldenberg | |
| 4,366,246 A | 12/1982 | Riggs | |
| 4,370,417 A | 1/1983 | Hung | |
| 4,399,216 A | 8/1983 | Axel et al. | |
| 4,419,446 A | 12/1983 | Howley | |
| 4,431,740 A | 2/1984 | Bell | |
| 4,440,859 A | 4/1984 | Rutter | |
| 4,500,637 A | 2/1985 | Neville, Jr. et al. | |
| 4,511,502 A * | 4/1985 | Builder et al. | |
| 4,565,785 A | 1/1986 | Gilbert | |
| 4,599,197 A | 7/1986 | Wetzel | |
| 4,634,665 A | 1/1987 | Axel et al. | |
| 4,642,334 A | 2/1987 | Moore | |
| 4,668,629 A | 5/1987 | Kaplan et al. | |
| 4,713,339 A | 12/1987 | Levinson et al. | |
| 4,766,075 A | 8/1988 | Goeddel et al. | |
| 4,792,447 A | 12/1988 | Uhr et al. | |
| 4,816,567 A | 3/1989 | Cabilly et al. | |
| 4,965,196 A | 10/1990 | Levinson et al. | |
| 5,081,235 A | 1/1992 | Shively et al. | |
| 5,098,833 A | 3/1992 | Lasky et al. | |
| 5,116,964 A | 5/1992 | Capon et al. | |
| 5,137,721 A | 8/1992 | Dallas | |
| 5,179,017 A | 1/1993 | Axel et al. | |
| 5,225,538 A | 7/1993 | Capon et al. | |
| 5,336,603 A | 8/1994 | Capon et al. | |
| 5,420,020 A | 5/1995 | Riggs | |
| 5,428,130 A | 6/1995 | Capon et al. | |
| 5,455,165 A | 10/1995 | Capon et al. | |
| 5,500,362 A | 3/1996 | Robinson et al. | |
| 5,514,582 A | 5/1996 | Capon et al. | |
| 5,561,053 A | 10/1996 | Crowley | |
| 5,583,013 A | 12/1996 | Itakura | |
| 5,585,089 A | 12/1996 | Queen et al. | |
| 5,605,689 A | 2/1997 | Ammann | |
| 5,612,185 A | 3/1997 | Uhr et al. | |
| 5,648,237 A | 7/1997 | Carter | |
| 5,686,072 A | 11/1997 | Uhr et al. | |
| 5,721,108 A | 2/1998 | Robinson et al. | |
| 5,736,137 A | 4/1998 | Anderson et al. | |
| 5,807,715 A | 9/1998 | Morrison et al. | |
| 5,840,545 A | 11/1998 | Moore | |
| 5,846,818 A | 12/1998 | Robinson et al. | |
| 5,877,293 A | 3/1999 | Adair et al. | |
| 5,965,405 A | 10/1999 | Winter | |
| 5,997,867 A | 12/1999 | Waldmann et al. | |
| 6,054,297 A | 4/2000 | Carter et al. | |
| 6,054,561 A | 4/2000 | Ring | |
| 6,120,767 A | 9/2000 | Robinson et al. | |
| 6,204,023 B1 | 3/2001 | Robinson et al. | |
| 6,331,415 B1 | 12/2001 | Cabilly et al. | |
| 6,455,275 B1 | 9/2002 | Axel et al. | |
| 6,548,640 B1 | 4/2003 | Winter | |

FOREIGN PATENT DOCUMENTS

| | | |
|---|---|---|
| EP | 0 036 776 | 3/1981 |
| EP | 044722 | 1/1982 |
| EP | 0 044 722 | 1/1982 |

(Continued)

OTHER PUBLICATIONS

Harvard Journal of Law & Technology 17(2) (Spring 2004), pp. 583–618.*
Jun. 5, 1995 preliminary amendment in the Moore U.S. Appl. No. 08/461,071.*
Declaration of Dr. Richard Axel, submitted Oct. 5, 1989 in U.S. Appl. No. 08/422,187.*

(Continued)

*Primary Examiner*—Padmashri Ponnaluri

(57) ABSTRACT

The invention relates to processes for producing an immunoglobulin or an immunologically functional immunoglobulin fragment containing at least the variable domains of the immunoglobulin heavy and light chains. The processes can use one or more vectors which produce both the heavy and light chains or fragments thereof in a single cell. The invention also relates to the vectors used to produce the immunoglobulin or fragment, and to cells transformed with the vectors.

FOREIGN PATENT DOCUMENTS

| | | |
|---|---|---|
| EP | 060057 | 9/1982 |
| EP | 0 114 506 | 12/1983 |
| EP | 102634 | 3/1984 |
| EP | 0171496 | 2/1986 |
| EP | 173494 | 3/1986 |
| EP | 177343 | 4/1986 |
| EP | 365997 | 5/1990 |
| EP | 0481790 | 4/1992 |
| WO | 81/02426 | 9/1981 |
| WO | WO 82/03088 | 9/1982 |
| WO | 83/00164 | 1/1983 |
| WO | 87/02671 | 5/1987 |
| WO | 89/00999 | 2/1989 |
| WO | 89/01783 | 3/1989 |
| WO | 92/16553 | 10/1992 |
| WO | 93/07899 | 4/1993 |
| WO | 93/10817 | 6/1993 |
| WO | 93/21319 | 10/1993 |
| WO | 97/30087 | 8/1997 |

OTHER PUBLICATIONS

Accolla et al., *Proc. Nat'l Acad. Sci. USA* 77:563 (1980).
Rice and Baltimore, *Proc. Nat'l Acad. Sci. USA* 79:7862 (1982).
Deacon et al., Antibody Synthesis in *Xenopus* Oocytes with Messenger Ribonucleic Acid from Immunized Rats, Biochemical Society Transactions, vol. 4, pp. 818–820 (1976).
Ochi et al., Transfer of a cloned immunoglobulin light–chain gene to mutant hybridoma cells restores specific antibody production, Nature, vol. 302, pp. 340342 (1983).
Oi et al., Immunoglobulin gene expression in transformed lymphoid cells, Proc. Natl. Acad. Sci. USA, vol. 80, pp. 825–829 (1983).
Rice et al., Regulated expression for an immunoglobulin κ gene introduced into a mouse lymphoid cell line, Proc. Natl. Acad. Sci. USA, vol. 79, pp. 7862–7865 (1982).
Valle et al., Synthesis and secretion of mouse immunoglobulin chains from *Xenopus* oocytes, Nature, vol. 291, pp. 338–340 (1981).
Valle et al., Anti–ovalbumin monoclonal antibodies interact with their antigen in internal membranes of *Xenopus* oocytes, Nature, vol. 300, pp. 71–74 (1982).
U.S. Appl. No. 07/233,430, Boss et al.
U.S. Appl. No. 07/930,821, Boss et al.
U.S. Appl. No. 08/320,381, Boss et al.
U.S. Appl. No. 08/450,727, Boss et al.
U.S. Appl. No. 08/452,420, Boss et al.
U.S. Appl. No. 08/453,449, Boss et al.
Abbas et al., Cellular and Molecular Immunology, Second Edition pp. 38–39 (1994).
Abstract, Journal of Nuclear Medicine, May 1990, No. 613 (Exhibit 1177, Int. No. 104,532).
Abstract, The Society of Nuclear Medicine 37th Annual Meeting, Washington Convention Center—Washington, D.C., Tuesday, Jun. 19–Friday, Jun. 22, 1990 (Exhibit 1180, Int. No. 104,532).
Abstract, World Federation of Nuclear Medicine & Biology, Abstract submitted Jan. 15, 1990 (Exhibit 1178, Int. No. 104,532).
Achord et al. 1978. Human 0–glucuronidase: in vivo clearance and in vitro uptake by a glycoprotein recognition system on reticuloendothelial cells. Cell 15:269–278.
Alberts et al. Molecular Biology of The Cell, pp. 285 and 375. Garland Publishing, Inc., (1983).

Alberts, B. Molekularbiologie der Zelle, Weinheim: VCH p. 1075 (1987).
Alt et al. "Immunoglobulin heavy–chain expression and class switching in a murine leukaemia cell line," Nature, vol. 298, p. 325–31, (Mar. 25, 1982).
Andrews, D.W. and J.D. Capra. 1980. Clinical Immunobiology. pp. 1–18, W.B. Sanders.
Arathoon, et al.—Large–Scale Cell Culture in Biotechnology pp. 1390–1395, Science, vol. 232, Jun. 1986 (Exhibit 1157; Int. No. 104,532).
Arthritis & Rheumatism, Abstract Suppl. vol. 39, No. 9, Sep. 1996, p. S244.
Ashford et al. 1993 "Site–specific Glycosylation of Recombinant Rat and Human Soluble CD4 Variants Expressed in Chinese Hamster Ovary Cells", J. Biol. Chem., 268, 3260–3267.
Bagdasarian et al., "Activity of the hybrid trp–lac (tac) promoter of putida. Construction of broad–host–range, controlled–expression vectors" Gen 26 (2–3): 273–282 (Dec. 1983).
Baldwin, R.W. et al. 1990. Monoclonal Antibodies and Immunoconjugates. The Parthenon Publishing Group (UK), p. 209.
Banerji et al., "A Lymphocyte–Specific Cellular Enhancer Is Located Downstream of the Joining Region in Immunoglobulin Heavy Chain Genes," Cell, vol. 33, 729–740 (Jul. 1982).
J. Baselga et al., "Recombinant Humanized Anti–HER2 Antibody (Herceptin™) Enhances the Antitumor Activity of Paclitaxel and Doxorubicin against HER2/neu Overexpressing Human Breast Cancer Xenografts", Cancer Res. (1988) 58: 2825–2831.
Beatty et al., Cancer Research (Suppl). 50:922s–926s (Feb. 1, 1990) (Exhibit 1011; Int. No. 104,532).
Beatty et al., Cancer Research 49:1587–1594 (Mar. 15, 1989) (Exhibit 1010; Int. No. 104,532).
Begent et al., Br. J. Cancer, 62:487 (1990) (Exhibit 1088; Int. No. 104,532).
Benoist, C., et al., "In vivo sequence requirements of the SV40 early promoter region," Nature, 290: 304–310 (1981).
Bergman, Y., et al., "Two regulatory elements for *immunoglobulin kappa* light chain gene expression," *Proc. Natl. Acad. Sci.*, 81: 7041–45 (1984).
Berman et al., Science, Nov. 4, 1983; 222(4623): 524–7.
Bernier, "Proliferative Disorders of the Immune System," Chapter 21 (pp. 622–643) in Bellanti, *Immunology II* (1978).
Bindon et al. (1985). Therapeutic potential of monoclonal antibodies to the leukocyte–common antigen. Synergy and interference in complement–mediated lysis. Transplantation 40(5):538–44 (Exhibit 2072; Int. No. 104,532).
Blatt, C. and J. Haimovich. 1981. The selective effect of tunicamycin on the secretion of IgM and IgG produced by the same cells. European Journal Of Immunology 11:65–66.
Blair, DG, et al., "Activation of the transforming potential of a normal cell sequence: a molecular model for oncogenesis," *Science*, 212: 941–43 (1981).
Breathnach, R., et al. "Corrected splicing of a chicken ovalbumin gene transcript in mouse L cells," *Proc. Natl. Acad. Sci.*, 77: 740–44 (1980).
Bruggemann et al. 1987. Comparison of the effector functions of human immunoglobulins using a matched set of chimeric antibodies. Journal of Experimental Medicine 166(5):1351–61 (Exhibit 2079; Int. No. 104,532).

Byrn, et al., Nature 344:667–670 (Apr. 12, 1990) (Exhibit 1055; Int. No. 104,532).

Cabilly, S. and A.D. Riggs. 1985. Immunoglobulin transcripts and molecular history of a hybridoma that produces antibody to carcinoembryonic antigen. Gene 40(I):157–61 (Exhibit 2073; Int. No. 104,532).

Cabilly, Shmuel, "Growth at sub-optimal temperatures allows the production of functional, antigen-binding Fab fragments in *Escherichia coli*" Gene 85:553–57 (1989).

Cancer Principles & Practice of Oncology, 5th Edition, vol. 1, Chapter 18, pp. 360–372 (Exhibit 1181; Int. No. 104,532).

Carter et al., "High Level *Escherichia coli* Expression and Production of a Bivalent Humanized Antibody Fragment." Bio/Technology 10(2):153–167 (Feb. 1992).

Chang, E., et al., "Transformation by cloned Harvey sarcoma virus DNA: efficiency increased by long terminal repeat DNA," *Science*, 210: 1249–51 (1980).

Chang et al., Proc. Natl. Acad. Sci. USA, vol. 84, pp. 5640–5644 (1987) (Exhibit 1107; Int. No. 104,532).

Clynes et al., 2000 "Inhibitory Fc receptors modulate in vivo cytoxicity against tumor antigens" Nature Med 6: 443–446.

Cobbold et al., Bone Marrow Purging and Processing, pp. 139–154 (Jan. 1, 1990) (Exhibit 1027; Int. No. 104,532).

Cobbold, S.P. and H. Waldmann, "Therapeutic potential of monovalent monoclonal antibodies" Nature 308(5958):460–62 (1984) (Exhibit 2068; Int. No. 104,532).

Code of Medical Ethics and Current Opinions, excerpts from pp. 339–379 (Exhibit 2269; Int. No. 104,532).

Colcher et al., Cancer Res. 49:1738–1745 (1989) (Exhibit 1047; Int. No. 104,532).

Crowe, et al., A Clinical Experimental Immunology, 1992, 87, pp. 105–110 (Exhibit 1070; Int. No. 104,532).

Davies, J., et al., "A new selective agent for eukaryotic cloning vectors," *Am J. Trop. Med. Hyg.*, 29 (5 Suppl): 1089–92 (1980).

Davis et al. 1990, "High Level Expression in Chinese Hamster Ovary Cells of Soluble Forms of CD4 T Lymphocyte Glycoprotein Including Glycosylation Variants." J Biol. Chem. 265, 10410–10418 (Exhibit 2189; Int. No. 104,532).

Davis, "Immunoglobulin molecules and genes" Microbiology Including Immunology and Molecular Genetics, Third edition, 1980, Chapter 17, pp. 338–379, Harper & Row, Hagerstown, MD.

De Waele et al. 1988. Expression in non-lymphoid cells of mouse recombinant immunoglobulin directed against the tumor marker human placental alkaline phosphatase. European Journal of Biochemistry 176:287–295 (Exhibit 2109; Int. No. 104,532).

Dean, C.J. 1994. Preparation and characterization of monoclonal antibodies to proteins and other cellular components. Methods in Molecular Biology 32:361–379 (Exhibit 2026; Int. No. 104,532).

DeBoer, "The tac promoter: A functional hybrid derived from the trp and lac Promoters" Proc. Natl. Acad. Sci. USA 80:21–25 (1983).

Devita et al., Cancer: Principles & Practice of Oncology, 1997, 5th Ed., vol. 1, Chapter 18, VT. DeVita (Ed.), Lippincott–Raven, Philadelphia, PA.

Duda et al., J. Surgical Oncology 44:73–77 (Jun. 1990) (Exhibit 1014; Int. No. 104,532).

Dyer et al., Blood 73:1431–1439 (May 1, 1989) (Exhibit 1025; Int. No. 104,532).

Emery & Adair, Exp. Opin. Invest. Drugs (1994) 3(3):241–251 (Exhibit 1087; Int. No. 104,532).

Estabrook A. and J. A. K. Patterson, "Immunotherapy using monoclonal antibodies," J. of Cutaneous Pathology 10: 559–66 (1983).

Ettinger, et al. Cancer Treatment Reports vol. 83, No. 1, pp. 131–134, Jan. 1979 (Exhibit 1129; Int. No. 104,532).

Finnegan et al., J. Rheumatology 1997, 24:7, 1448–1449 (Exhibit 1069; Int. No. 104,532).

Fittler et al., "Localization in Mouse–L–Cell Chromosomal Sites of Transferred Immunoglobulin Genes," Chromosoma (Berl.) 84, 717–727 (1982).

Fleischman, J. BioScience Reports 5:893–899 (1985) (Exhibit 1080 Case No. CIV S–00–1252 WBS GGH).

Frenkel et al. 1980. Analysis and detection of B cell neoplasms. Blood Cells 6:783–793 (Exhibit 2123; Int. No. 104, 532).

Friend et al., Transplantation 48:248–253 (Aug. 1, 1989) (Exhibit 1023; Int. No. 104,532).

Fundenberg and Koistinen, "Human Allotype Detection by Passive Hemagglutination, with Special Reference to Immunoglobulin A Allotypes" Chapter 103 (pp. 767–774) in Rose and Friedman, *Manual of Clinical Immunology*, Second Edition (1980).

Geisse et al. 1996. Eukaryotic expression systems: a comparison. Protein Expression and Purification 8:271–282 (Exhibit 2025; Int. No. 104,532).

Gillies et al., "Expression of cloned immunoglobulin genes introduced into mouse L cells," Nucl. Acids. Res., vol. 11, No. 22, pp. 7982–7997 (1983).

Glaser et al., "Functional interrelationship between two tandem *E. coli* ribosomal RNA promoters" Nature 302(59031:74–76 (Mar. 3, 1983).

Goeddel et al. 1979. Direct expression in *Escherichia coli* of a DNA sequence coding for human growth hormone. Nature 281(5732):544–8 (Exhibit 2038; Int. No. 104,532).

Goeddel et al., "Synthesis of Human Fibroblast Interferon by *E. coli*" Nucleic Acids Research 8(18):4057–4074 (1980).

Goeddel, Methods in Enzymology, vol. 185, AGene Expression Technology (1990) (Exhibit 1077; Int. No. 104,532).

Gold et al. 1978. Carcinoembryonic antigen (CEA) in clinical medicine. Cancer 42:1399–1405 (Exhibit 2135; Int. No. 104,532).

Goochee et al. 1991, "The Oligosaccharides of Glycoproteins: BioProcess Factors Affecting Oligosaccharide Structure and Their Effect on Glycoprotein Properties", Bio Technology 9, 1347–1355 (Exhibit 2187; Int. No. 104,532).

Goochee, C. F., and T. Monica. 1990. Environmental effects on protein glycosylation. Bio Technology 8:421–427 (Exhibit 2023; Int. No. 104,532).

Goodman and MacDonald, "Cloning of hormone genes from a mixture of cDNA molecules" Methods in Enzymology 68:75–90 (1979).

Greipp, P. 1992. Advances in the diagnosis and management of myeloma. Seminars in Hematology 29(3: Suppl. 2):24–45 (Exhibit 2020; Int. No. 104,532).

Grillo–Lopez et al. 1999. Overview of the clinical development of rituximab: first monoclonal antibody treatment approved for the treatment of lymphoma. Seminars in Oncology 26:66–73 (Exhibit 2144; Int. No. 104,532).

Gross et al, "Bone marrow Purging and Processing," International Symposium on Bone Marrow Purging and Processing (2nd, Apr. 27 and 28, 1989 Cancun, Mexico) Gross et al. (Ed.), Wiley–Liss, NY.

Grossbard, M.L. 1998. Monoclonal Antibody Based Therapy of Cancer. Marcel Dekker, p. 451 (Exhibit 2094; Int. No. 104,532).

Gruss, P., et al., "Simian virus 40 tandem repeated sequences as an element of the early promoter," *Proc. Natl. Acad. Sci.*, 78:943–47 (1981).

Habara et al. "Rauscher Murine Leukemia Virus: Molecular Cloning of Infectious Integrated Proviral DNA," J. of Virology, vol. 44, No. 2, pp. 731–735 (No.v 1982).

Hale et al. 1985. Reactivity of rat monoclonal antibody CAMPATH–I with human leukemia cells and its possible application for autologous bone marrow transplantation. British Journal of Hematology 60(I):41–8 (Exhibit 2074; Int. No. 104,532).

Hale et al. 1988. Remission induction in non Hodgkin lymphoma with reshaped human monoclonal antibody CAMPATH–I H. Lancet 2 (8625): 1394–1399 (Exhibit 2015 and 1024; Int. No. 104,532).

Hale et al., 1990. The Campath–I antigen (CDw52). Tissue Antigens 35:118–127 (Exhibit 2049 Int. No. 104,532).

Hale, "Effects of Monoclonal Anti–lymphocyte Antibodies in Vivo in Monkeys and Humans", Mol Biol Med (1983) 1, 321–334 (Exhibit 2240; Int. No. 104,532).

Hale, Progress Report (May 1990–Dec. 31, 1990), MRC Wellcome Therapeutic Antibody Center (Exhibit 1072; Int. No. 104,532).

Hamilton, R., "Application of engineered chimeric antibodies to the calibration of human antibody standards" Annales de Biologie Clinigue 49 (4):242–248 (1991).

Harris "Expression of Eukaryotic Genes in *E. coli*" Genetic Engineering, R.Williamson, $4^{th}$ edition pp. 127–185 (1983).

Harris, et al., Proceedings of the 34th Oholo Conference, Eilat, Israel (1990) (Exhibit 1073; Int. No. 104,532).

Haynes and Weissmann, "Constitutive, long–term production of human interferons by hamster cells containing multiple copies of a cloned interferon gene," (1983) Nucl. Acid. Res., vol. 11 No. 3, pp. 687–706 (Exhibit 1109; Int. No. 104,532).

Hodge, J.W. 1996. carcinoembryonic antigen as a target for cancer vaccines. Cancer Immunol and Immunother 43:127–134 (Exhbit 2032; Int. No. 104,532).

Hutchins et al., Proc. Natl. Acad. Sci. USA, vol. 92, pp. 11980–11984 (1995).

Huynh et al., 1984. Constructing and screening cDNA libraries in kgt IO and kgtl 1. DNA Cloning, vol. I—A practical Approach 49–78. Glover, D(Editor), IRL Press, Oxford (Exhibit 2050; Int. No. 104,532).

Jackson and Davis, "Quantitation of Immunoglobulins," Chapter 14 (pp. 109–120) in Rose and Friedman, *Manual of Clinical Immunology*, Second Edition (1980).

Jefferis et al. 1998. IgG–Fc–mediated effector functions: molecular definition of interaction sites for effector ligands and the role of glycosylation. Immunological Reviews 163:59–76 (Exhibit 2095; Int. No. 104,532).

Joziasse, et al., 2000 "a3–Galactosylated glycoproteins can bind to the hepaticasialoglycoprotein receptor" Eur. J. Biochem. 267:6501–6508 (Exhibit 1037; Int. No. 104,532).

Kabat et al. Sequences of Proteins of Immunological Interest, Bethesda, MD: National Institute of Health pp. i, xxi, xxii (1983).

Khazaeli, et al., Cancer Research, 51, 5461–5466 (1991) (Exhibit 1074; Int. No. 104,532).

Kabat et al., "Sequences of immunoglobulin chains: tabulation and analysis of amino acid sequences of precursors, V–regions, C–regions, J–chain and [beta]2–microglobulins . . . ," The Kabat Database of Sequences of Proteins of Immunological Interest, 1979, Publication No. 80–2008, p. 185, National Institute of Health, Bethesda, MD. (GNE–MED 52680).

Kaetzel et al. 1985. Expression of biologically active bovine luteinizing hormone in Chinese hamster ovary cells. Proc. Natl. Acad Sci. USA 82:7280–7283 (Exhibit 2152; Int. No. 104,532).

Kagawa Y; J Biol Chem Nov. 25, 1988:263(33):17508–15 (Exhibit 1153; Int. No. 104,532).

Kaufman et al. 1987. Coamplification and coexpression of human tissue–type plasminogen activator and murine dihydrofolate reductase sequences in Chinese hamster ovary cells. Molecular and Cellular Biology 5:1750–1759 (Exhibit 2075; Int. No. 104,532).

Khazaeli et al., Manuscript—Frequent Anti–V Region Immune Response to Mouse B72.3 Monoclonal Antibody (pp. 25–63).

Kipriyanov et al. 1999. Generation of recombinant antibodies. Molecular Biotechnology 12:173–201 (Exhibit 2017; Int. No. 104,532).

Klausner, A. "Genentech makes monoclonal precursors from *E.coli*" Bio/Technology I(5):396–397 (1983).

Kohler, G., et al., "Immunoglobulin chain loss in hybridoma cell lines," *Proc. Natl Acad. Sci.*, 77:2197–99 (1980).

Kohler, G. BioScience Reports 5:533–549 (1985) (Plaintiff Exhibit 1108, Case No. CIV S–00–1252 WBS GGH).

Krag et al., J. Biological Chemistry, vol. 257, No. 14, p. 8424 (1983) (Exhibit 1115; Int. No. 104,532).

Krag, J. Biol. Chem. 254:9167–9177 (1979) (Exhibit 1043; Int. No. 104,532).

Krolick et al. 1982. In vivo therapy of a Murine B cell tumor (BCL I) using antibody–ricin a chain immunotoxins. J Exp. Med. 155:1797–1809 (Exhibit 2122; Int. No. 104,532).

Kyle, "Classification and Diagnosis of Monoclonal Gammopathies," Chapter 16 (pp. 135–150) in Rose and Friedman, *Manual of Clinical Immunology*, Second Edition (1980).

Levy, R. and R.A. Miller. 1983. Biological and clinical implications of lymphocyte hybridomas: tumor therapy with monoclonal antibodies. Ann. Rev. Med–34:107–116 (Exhibit 2121; Int. No. 104,532).

Lifely et al., Glycobiology, vol. 5 No. 8; 813–822, 1995 (Exhibit 1170; Int. No. 104,532).

Lingappa et al. 1980. Signal sequences for early events in protein secretion and membrane assembly. Ann. NYAcad. Sci. 343:356–61 (Exhibit 2147; Int. No. 104,532).

Linscott's Directory (formerly Catalog) of Immunological and Biological Reagents, second edition 1982–83, pp. 1–57.

LoBuglio and Saleh, Am. J. Medical Sciences, Sep. 1992 vol. 304, No. 3, pp. 214–224 (Exhibit 1160; Int. No. 104, 532).

Liu et al., "Expression of mouse: human immunoglobulin heavy–chain cDNA in lymphoid cells" Gene 54(1):33–40 (1987).

M.D. Pegram et al., "Antibody dependent cell–mediated cytotoxicity in breast cancer patients in Phase III clinical trials of a humanized anti–HER2 antibody", Proc Am. Assoc. Cancer Res., 1997, 38:602 (#4044) (Exhibit 2248; Int. No. 104,532).

Ma, S. and W. Nashabeh. 1999. Carbohydrate analysis of a chimeric recombinant monoclonal antibody by capillary electrophoresis with laser–induced fluorescence detection. Analytical Chemistry 71:5185–5192 (Exhibit 2145; Int. No. 104,532).

Maniatis, T., E.F. Fritsch, and J. Sambrook. 1982. Table of Contents; "Extraction, Purification, and Analysis of MRNA from Eukaryotic Cells", 187–209; "Synthesis and Cloning of CDNA", 211–246; and "Construction of Genomic Libraries", 269–307. In Molecular Cloning A Laboratory Manual, New York: Cold Spring Harbor Laboratory (Exhibit 2008; Int. No. 104,532).

Margulies et al., "Regulation of immunoglobulin expression in mouse myeloma cells" Immunoglobulin Expression pp. 781–791 (1977) (GNE–MED 31462).

Marx, J. Science 229:455–456 (1985) (Plaintiff Exhibit No. 1118, Case No. CIV S–00–1252 WBS GGH).

Martinis et al., "Monoclonal antibodies with dual antigen specificity" Oncology pp. 311–316.

Matsuuchi et al. 1981. An analysis of heavy chain glycopeptides of hybridoma antibodies: correlation between antibody specificity and sialic acid content. Journal of Immunology 127(5):2188–90 (Exhibit 2060; Int. No. 104,532).

Mercola et al., "Transcriptional Enhancer Elements in the Mouse Immunoglobulin Heavy Chain Locus," Science, vol. 221, No. 4611, p. 663–65 (Aug. 12, 1983).

Meredith et al., J. Nucl. Med, Jan. 1992, 33:23–29 (pp. 13–19).

Meredith et al., J. Nucl. Med., vol. 33, No. 9: 1648–1653, Sep. 1992.

Meredith, et al., Hum. Antibod. Hybridomas, 1993, 4:190–197 (Exhibit 1083; Int. No. 104,532).

Miles Biochemicals 1979–80, p. 140–142.

Miller et al., "Transfection of human lymphoblastoid cells with herpes simplex viral DNA," Proc. Natl. Acad. Sci., vol. 76, No. 2, pp. 949–953 (Feb. 1979).

Morell et al. 1971. The role of sialic acid in determining the survival of glycoproteins in the circulation. J. Biol Chem. 246:1461–1467 (Exhibit 2117; Int. No. 104,532).

Morrison SL, et al., "A mouse myeloma variant with a defect in light chain synthesis," Eur. J. Immunol., 9:461–65 (1979).

Morrison et al. 1988. Genetically engineered antibody molecules: new tools for cancer therapy. Cancer Investigation 6(2):185–92 (Exhibit 2085; Int. No. 104,532).

Morrison et al. 1988. Production and characterization of genetically engineered antibody molecules. Clinical Chemistry 34(9):1668–75 (Defendant Exhibit 5009, Case No. CIV S–00–1252 WBS GGH).

Morrison, S. Hospital Practice 24(10):65–80 (1989) (GNE–MED 077476).

Morrison, S., "In vitro antibodies: strategies for production and application" Annual Review of Immunology 10:239–265 (1992).

Mulligan, RC, et al., "Selection for animal cells that express the Escherichia coli gene coding for xanthine–guanine phosphoribosyltransferase," Proc. Natl. Acad. Sci., 78 :2072–76 (1980).

Munro, "Uses of chimeric antibodies," Nature 312:597 (1984).

Neuberger, M. TIBS 347–349 (1985) (Plaintiff Exhibit 1130 (Case No. CIV S–00–1252 WBS GGH).

Neuhaus et al., JACC 14:1566–1569 (Nov. 15, 1989) (Exhibit 1032; Int. No. 104,532).

Neumaier et al., Cancer Research 50:2128–2134 (Apr. 1, 1990) (Exhibit 1013; Int. No. 104,532).

Nose, M. and H. Wigzell. 1983. Biological significance of carbohydrate chains on monoclonal antibodies. Proc. Natl. Acad. Sci. USA 80:6632–6636 (Exhibit 2022; Int. No. 104, 532).

Oi et al., "Immunoglobulin Gene Expressin in Transformed Lymphoid Cells," Proc. Natl. Acad. Sci., vol. 80, No. 3, p. 825–59 (Feb. 1, 1983).

Oi & Morrison BioTechniques 4(3):214–221 (1986) (Plaintiff Exhibit 1135, Case No. CIV S–00–1252 WBS GGH).

Oldham, R. 1983. Monoclonal antibodies in cancer therapy. Journal of Clinical Oncology 1:582–590 (Exhibit 2119; Int. 104,532).

Orfila et al., "Immunofluorescence study of "non–idiopathic" renal amyloidosis," Hum. Pathol. 14(4):362–7 (1983).

Peakman et al., Hum. Antibod. Hybridomas 5:65–74 (1994) (Exhibit 1038; Int. No. 104,532).

Page et al., Biotech, 9:64–68 (1991).

Picard et al., "Correct transcription of a cloned mouse immunoglobulin gene in vivo," Proc. Natl. Acad. Sci., vol. 80, pp. 417–421 (Jan. 1983).

Potamianos et al. 2000, Radioimmunoscintigraphy and Radioimmunotherapy in Cancer: Principles and Application, Anticancer Research 20, 925–948 (Exhibit 2185, Int. No. 104,532).

Primus et al., Cancer Immunol. Immunotherapy (1990) 31:349–357 (Exhibit 1164; Int. No. 104,532).

Queen and Baltimore, "Immunoglobulin gene transcription is activated by downstream sequence elements" Cell 33(3):741–748 (Jul. 1983).

Queen, C, "Comparison of mouse and human V–kappa domains" (Submitted by PDL Mar. 27, 1997).

Queen, C., "Comparison of human and mouse VH domains" (Submitted by PDL on Mar. 27, 1997.

Rademacher et al. (1988) Ann. Rev. Biochem. 57:785–838 (Exhibit 2165; Int. No. 104,532).

Raju et al. 2000. Species–specific variation in glycosylation of IgG: evidence for the species–specific sialylation and branch–specific galactosylation and importance for engineering recombinant glycoprotein therapeutics. Glycobiology 10(5):477–486 (Exhibit 2027; Int. No. 104,532).

Reff et al., Blood, vol. 83, No. 2, pp. 435–445 (1994) (Exhibit 1111; Int. No. 104,532).

Renner et al. 1997. Monoclonal antibodies in the treatment of non–Hodgkin's lymphoma: recent results and future prospects. Leukemia 11(2):S55–S59 (Exhibit 2019; Int. No. 104, 532).

Rhodes and Birch Biotechnology 6:518, 521, 523 (1988) (Exhibit 1046; Int. No. 104,532).

Rhodes, Adv. Anim. Cell. Biol. Technol. Bioprocess., 472–74 (1988) (Exhibit 1045; Int. No. 104,532).

Riechmann et al. 1988. Expression of an antibody Fv fragment in myeloma cells. Journal of Molecular Biology 203(3):825–8 (Exhibit 2087; Int. No. 104,532).

Riechmann et al. 1988. Reshaping human antibodies for therapy. Nature 322:323–327 (Exhibit 1022; Int. No. 104, 532).

Rosen et al. 1983. Application of monoclonal antibodies to tumor diagnosis and therapy. Annals of Clinical and Laboratory Science 13:173–184 (Exhibit 2120; Int. No. 104,532).

Routledge et al., Eur. J. Immunol. 1991, 21:2717–2725 (Exhibit 1068; Int. No. 104,532).

Schein et al., "Formation of Soluble Recombinant Proteins in *Escherichia coli* is Favored by Lower Growth Temperature" BioTechnoloqy 6:291–294 (1988).

Schein, Catherine H., "Production of soluble recombinant proteins in bacteria" Bio/Technology 7:1141–1149 (1989).

Sekigawa et al., J. Virology 64:5194–5198 (Oct. 1990) (Exhibit 1056; Int. No. 104,532).

Sheeley et al., Analytical Biochemistry 247, 102–110 (1997) (Exhibit 1096; Int. No. 104,532).

Sidman, C. 1981. Differing requirements for glycosylation in the secretion of related glycoproteins is determined neither by the producing cell nor by the relative number of oligosaccharide units. Journal of Biol. Chem. 256(18):9374–9376 (Exhibit 2100; Int. No. 104,532).

Solomon, "Bence–Jones Proteins and Light Chains of Immunoglobulins," Scand. J. Immunol., vol. 5, 685–695 (1976).

Southern, PJ et al. "Transformation of mammalian cells to antibiotic resistance with a bacterial gene under control of the SV40 early region promoter," *J. Molec. Appl. Genet.*, 1:327–41 (1982).

Spellman et al., 1989, J. Bio. Chem. 264:14100–14111 (Exhibit 1151; Int. No. 104,532).

Stafford and Queen, "Cell–type specific expression of a transfected immunoqlobulin qene" Nature 306(5938)—77–79 (Nov. 3, 1983).

Stevenson et al., 1989, A Chimeric Antibody With Dual Fc Regions (bisFabFc) Prepared by Manipulations at the IgG Hinge, Anti–Cancer Drug Design 3, 219–230 (Exhibit 2182; Int. No. 104,532).

Stevenson et al., Blood 77:1071–1079 (Mar. 1, 1991) (Exhibit 1026; Int. No. 104,532).

Summers et al., "Stable expression in mouse cells of nuclear neoantigen after transfer of a 3.4–megadalton cloned fragment of Epstein–Barr virus DNA," Proc. Natl. Acad. Sci., vol. 79, pp. 5688–5692 (Sep. 1982).

Sun et al. 1987. Chimeric antibody with human constant regions and mouse variable regions directed against carcinoma–associated antigen 17–IA. Proc. Natl. Acad. Sci. 84(I):214–8 (Exhibit 2080; Int. No. 104,532).

T.E. Hotaling et al., "The humanized anti–HER2 antibody rhuMAb HER2 mediates antibody dependent cell–mediated cytotoxicity via FcγR III", Proc. Am. Assoc. Cancer Res., 1996, 37:471 (#3215).

Takeda et al. Nature 314:452–454 (1985) (Plaintiff Exhibit 1171, Case No. CIV S–00–1252 WBS GGH).

Takei et al. 1980. Monoclonal antibody H9/25 reacts with functional subsets of T and B cells: killer, killer percursor and plaque–forming cells. European Journal of Immunology 10(7):503–9 (Exhibit 2042; Int. No. 104,532).

Takeuchi et al., J. Biol. Chem., 263:3657–3663, (Exhibit 1152; Int. No. 104,532).

Tan et al. 1985. A human–mouse chimeric in immunoglobulin gene with a human variable region is expressed in mouse myeloma cells. Journal of immunology 135(5):3564–7 (Exhibit 2078; Int. No. 104,532).

Taniguchi et al., "Expression of the Human Fibroblast Interferon Gene in *Escherichia Coli*", Proc. Natl. Acad. Sci. USA, 77(9):5230–5233 (Sep. 1980).

Tarentino et al. 1974. The release of intact oligosaccharides from specific glycoproteins by Endo–o–N–acetylglucosaminidase H. Journal of Biological Chemistry 249:818–824 (Exhibit 2116; Int. No. 104,532).

Tomimo et al., "Specificity of eluted antibody from renal tissues of patients with IgA nephropathy," Am. J. Kidney Dis. 1(5):276–80 (1982).

Trill et al. 1995. Production of monoclonal antibodies in COS and CHO cells. Current Opinion in Biotechnology 6: 553–560 (Exhibit 2108; Int. No. 104,532).

Tsuchiya et al. 1989. Effects of galactose depletion from oligosaccharide chains on immunological activites of human IgG. Journal of Hematology 16:285–90 (Exhibit 2092; Int. No. 104,532).

Urlaub, G. and L. A. Chasin. 1980. Isolation of Chinese hamster cell mutants deficient in dihydrofolate reductase activity. Proc. Natl. Acad Sci. USA 77:4216–4220 (Exhibit 2031; Int. No. 104,532).

Van Brunt, J. 1986. There's nothing (quite) like the real thing. Bio/Technology 4:835–839 (Exhibit 2024; Int. No. 104,532).

Van Nagell et al. 1980. Radioimmunodetection of primary and metastasis ovarian cancer using radiolabeled antibodies to carcinoembryonic antigen. Cancer Research 40(3):502–6 (Exhibit 2043; Int. No. 104,532).

Verhoeyen et al. 1988. Reshaping human antibodies: grafting an antilysozyme activity. Science 239(4847):1534–6 (Exhibit 2089; Int. No. 104,532).

Villiers et al. "Transcriptional 'enhancers' from SV40 and polyoma virus show a cell type preference," Nucl. Acids Res., vol. 10, No. 24, p. 7965–76 (1982).

Wagener, Shively publication (Bates Nos. 0927–0934) (GNE–MED–01597).

Wallick et al. 1988. Glycosylation of a VH residue of a monoclonal antibody against alpha (1 |6) dextran increases its affinity for antigen. Journal Of Experimental Medicine 168(3):1099–109 (Exhibit 2090; Int. No. 104,532).

Weidle et al. 1987. Expression of antibody CDNA in murine myeloma cells: possible involvement of additional regulatory elements in transcription of in immunoglobulin genes. Gene 60 (2–3):205–216 (Exhibit 2082; Int. No. 104,532).

Weidle et al. 1987. Reconstitution of functionally active antibody directed against creatine kinase from separately expressed heavy and light chains in non–lymphoid cells. Gene 51(I):21–9 (Exhibit 2081; Int. No. 104,532).

White et al., "Biologicals from recombinant microorganisms and animal cells: production and recovery," Proceedings of the 34th [i.e. 35th] OHOLO Conference, Eilat, Isreal, 1990, p. 567, White et al. (Ed.) (Exhibit 1073; Int. No. 104,532).

Whittle et al., Expression in COS cells of a mouse—human chimaeric B72.3 antibody, 1987, pp. 499–505, vol. 1, No. 6.

Wickens et al. 1978. Synthesis of double–stranded DNA complementary to lysozyme, ovomucoid, and ovalbumin mRNAs. Optimization of full length second strand synthesis by *Escherichia coli* DNA polymerase 1. Journal ofbiological Chemistry 253(7):2483–95 (Exhibit 2036; Int. No. 104,532).

Williams et al. Cancer Research (Suppl.) 50:1029s–1030s (Feb. 1, 1990) (Exhibit 1012; Int. No. 104,532).

Wold et al., "Introduction and expression of a rabbit β–globin gene in mouse fibroblasts," Proc. Natl. Acad. Sci., Bol. 76, No. 11 pp. 5694–88 (Nov. 1979).

Wood et al., J. Immunol., vol. 145:3011–3016, No. 9, Nov. 1, 1990 (Exhibit 1089; Int. No. 104,532).

Wright and Morrison, 1994 Effect of Altered CH2–associated Carbohydrate Structure on the Functional Properties and In Vivo Fate of Chimeric Mouse–Human Immunoglobulin GI, J. Exp. Med 180,1087–1096 (Exhibit 2186; Int. No. 104,532).
Zettlmeissl et al. 1987. Expression of biologically active human antithrombin III in Chinese hamster ovary cells. Biol Technology 5:720–5 (Exhibit 1076; Int. No. 104,532).
Rey Nbk #1173 (Bates Nos. 0502, 0504, 0509–0516, 0521–0522, 0525–0528, 0530–0531, 0533–0537, 0541, 0543–0544).
Mumford Nbk #1246 (Bates Nos. 0615, 0617, 0626–0627, 0645).
Perry Nbk #1290 (Bates Nos. 0136a–0136b, 0142–0147, 0149–0154, 0156–0158, 0160–0161, 0164–0173, 0181, 0187–0188, 0190–0192, 0197–0218, 0223, 0237, 0244–0261, 0304–0307).
Wetzel Nbk #1432 (Bates Nos. 0034 0044, 0047, 0049 0050, 0053, 0061 0064, 0077 0081, 0087–0088).
Holmes Spiral #44 (Bates Nos. 0825, 0830, 0837–0838, 0840–0843, 0845–0846, 0848–0849, 0852–0853, 0855, 0858).
Holmes Spiral #5 (Bates Nos. 0876, 0881–0882, 0885–0887, 0889).
Holmes Nbk #1446 (Bates Nos. 0941–0943, 0946–0947, 0950, 0954–0957).
Perry Nbk #1683 (Bates Nos. 0336–0342, 0357–0362).
File History U.S. Appl. No. 08/909,611.
File History of U.S. Patent No. 5,545,404 (U.S. Appl. No. 08/335,400) (Exhibit 2163; Int. No. 104,532).
File History of U.S. Patent No. 5,545,405 (U.S. Appl. No. 08/335,401) (Exhibit 2164; Int. No. 104,532).
Robinson's U.S. Appl. No. 07/016,202, filed Jan. 8, 1987 (Exhibit 2153; Int. No. 104,532).
Robinson's U.S. Appl. No. 08/471,984, filed Jun. 6, 1995 (Exhibit 2154; Int. No. 104,532).
Cabilly U.S. Appl. No. 07/205,419, filed Jun. 10, 1988.
Restriction Requirement (Paper No. 4) dated Mar. 6, 1990 in U.S. Appl. No. 07/205,419.
Restriction Requirement (Paper No. 11) dated Sep. 7, 1990 in U.S. Appl. No. 07/205,419.
Appointment of Associate Attorney, Mar. 25, 1991 in U.S. Appl. No. 07/205,419.
Interview Summary (Paper No. 22) in U.S. Appl. No. 07/205,419.
Amendment After Interference (Paper No. 24) filed Oct. 4, 2001 in U.S. Appl. No. 07/205,419.
Decision Granting Petition to Correct the Assignee on the Correction Page of U.S. Appl. No. 07/205,419, May 7, 2002.
File History of U.S. Patent No. 4,816,397 (Boss et al.).
Declaration of Interference, Feb. 28, 1991 (Int. No. 102,572).
Summary of Times Running, Feb. 28, 1991 (Int. No. 102,572).
Designation of Lead Attorney (Cabilly), Mar. 14, 1991 (Int. No. 102,572).
Submission of Associate Attorneys, Apr. 8, 1991 (Int. No. 102,572).
Revocation of Power of Attorney, Apr. 15, 1991 (Int. No. 102,572).
Boss et al. Substitution of Lead Attorney, Apr. 19, 1991 (Int. No. 102,572).
Associate Power of Attorney, Apr. 19, 1991 (Int. No. 102, 572).
Cabilly et al. Motion for Extension of Time, May 28, 1991 (Int. No. 102,572).
Cabilly et al. Extension of Time–Approved, Jun. 3, 1991 (Int. No. 102,572).
Transmittal of Preliminary Statement of Boss et al. and Notice to Opposing Party, Jun. 4, 1991 (Int. No. 102,572).
Boss et al. Motion for Benefit of its PCT Application (Boss Motion 1), Jun. 4, 1991 (Int. No. 102,572).
Boss et al. Motion for Benefit of its British Application (Boss Motion 2), Jun. 4, 1991 (Int. No. 102,572).
Declaration of Timothy John Roy Harris in Support of Boss Motion for Benefit of its British Application (Boss Motion 2), Jun. 4, 1991 (Int. No. 102,572).
Boss et al. Motion for Judgment of Unpatentability of Cabilly Claims (Boss Motion 3), Jun. 4, 1991 (Int. No. 102, 572).
Certificate of Service and List of Documents Filed, Jun. 4, 1991 (Int. No. 102,572).
Cabilly et al. Notice of Filing of Preliminary Statement, Jun. 4, 1991 (Int. No. 102,572).
Preliminary Statement of the Party Cabilly et al., Jun. 4, 1991 (Int. No. 102,572).
Cabilly et al. Request for the Exercise of Discretion Pursuant to 37 C.F.R. § 1.642, Jun. 4, 1991 (Int. No. 102,572).
Boss et al. Opposition to Cabilly et al. Request Pursuant to 37 C.F.R. § 1.642, Jun. 24, 1991 (Int. No. 102,572).
Opposition to Boss et al. Motion for Judgment of Unpatentability of Cabilly et al. Claims (Boss Motion 3), Jun. 24, 1991 (Int. No. 102,572).
Declaration of Paul Carter In Support Of Cabilly et al Opposition to Boss et al Motion For Judgment Of Unpatentability of Cabilly et al Claims 101–120 (Boss Motion 3), Jun. 24, 1991 (Int. No. 102,572).
Boss et al Reply to Opposition to Boss et al Motion for udgment of Unpatentability of Cabilly Claims, Jul. 9, 1991 (Int. No. 102,572).
Decision on Motions, Jul. 26, 1991 (Int. No. 102,572).
Order Regarding Testimony, Jul. 26, 1991 (Int. No. 102, 572).
Service of Boss et al. Preliminary Statement; Boss et al. Preliminary Statement, Jul. 31, 1991 (Int. No. 102,572).
Service of Cabilly et al. Preliminary Statement, Aug. 13, 1991 (Int. No. 102,572).
"Communication" to PTO from Cabilly et al. (Paper #28); Information Disclosure Statement, Sep. 20, 1991 (Int. No. 102,572).
Cabilly et al. Motion for Extension of Time, Sep. 25, 1991 (Int. No. 102,572).
Decision—dismissal of "Communication" paper, Sep. 26, 1991 (Int. No. 102,572).
Transmittal Letter re: Declarations of Riggs, Shively, Wetzel, Perry, Holmes, Rey, Mumford, Cabilly and Exhibits 1–20, Notice Pursuant to 37 CFR 1.671(e), Oct. 28, 1991 (Int. No. 102,572).
Proposed Revision to Schedule for Records and Briefs, Dec. 3, 1991 (Int. No. 102,572).
Cabilly et al. Notice of Filing Record, Jan. 8, 1992 (Int. No. 102,572).
Motion by the Party Cabilly et al Pursuant to 37 CFR ∈ 1.635 to Replace Exhibits 1–20 Filed on Jan. 8, 1992 With a Corrected Set of Exhibits and for the Return of Exhibits 1–20 Filed 1–20 on Jan. 8, 1992, Jan. 22, 1992 (Int. No. 102,572).
Corrected Submission of Stipulation Concerning Testimony, Feb. 5, 1992 (Int. No. 102,572).

Cabilly et al. Motion for Extension of Time, Feb. 10, 1992 (Int. No. 102,572).
Main Brief at Final Hearing of Junior Party Cabilly et al., Feb. 18, 1992 (Int. No. 102,572).
Transmittal of Brief for the Party Boss et al., Mar. 18, 1992 (Int. No. 102,572).
Brief at Final Hearing for Senior Party Boss et al., Feb. 18, 1992 (Int. No. 102,572).
Reply Brief at Final Hearing of Junior Party Cabilly et al., Apr. 7, 1992 (Int. No. 102,572).
Cabilly et al Motion Pursuant to 37 C.F. R. § 1.635 To Enter Additional Pages Into the Cabilly et al Record, Apr. 14, 1992 (Int. No. 102,572).
Opposition to Cabilly et al Motion Pursuant to 37 C.F. R. §1.635 To Enter Additional Pages Into the Cabilly et al Record, Apr. 22, 1992 (Int. No. 102,572).
Cabilly et al Reply to Boss et al Opposition to Cabilly et al Motion Pursuant to 37 C.F. R. § 1.635 To Enter Additional Pages Into the Cabilly et al Record, May 7, 1992 (Int. No. 102,572).
Notice of Filing Substitute Exhibits 8 and 20 for the Cabilly et al. Record, May 7, 1992 (Int. No. 102,572).
Cabilly et al. Notice of Submission of Replacement Set of Exhibits 1–20, May 7, 1992 (Int. No. 102,572).
Notice of Final Hearing for Mar. 29, 1994 (paper #54), Feb. 4, 1992 (Int. No. 102,572).
Cabilly et al. Supplemental Brief at Final Hearing, Apr. 5, 1992 (Int. No. 102,572).
Final Decision (Priority awarded to Boss et al.) (paper #57), Aug. 13, 1998 (Int. No. 102,572).
Transmittal and Filing of Agreements Under 35 USC §135(c) (Int. No. 102,572).
Communication form BPAI re: Filing of agreements and request to keep separate from interference file acknowledged (paper #59), Sep. 10, 1998 (Int. No. 102,572).
Notice From PTO Requesting Comunication Regarding Appeal, Nov. 19, 1998 (Int. No. 102,572).
Belated Response to Communication Regarding Appeal, Dec. 1, 1998 (Int. No. 102,572).
Boss et al. Power to Inspect and Make Copies, Dec. 9, 1998 (Int. No. 102,572).
Final Order After District Court Judgment, Jul. 25, 2001 (Int. No. 102,572).
Petition Pursuant to 37 C.F.R. § 1.666(b) for Access to Settlement Agreement (filed by Med Immune), May 8, 2002 (Int. No. 102,572).
Order on Petition for Access Pursuant to 35 U.S.C. § 165(c) and 37 C.F.R. § 1.666(b), Jun. 19, 2002 (Int. No. 102,572).
Cabilly et al. Objection to Petition for Access to Settlement Agreement, Jul. 22, 2002 (Int. No. 102,572).
Celltech's Objection to Petition for Access to Settlement Agreement, Jul. 22, 2002 (Int. No. 102,572).
Reply to Objections of Celltech R&D Ltd. and Cabilly et al. to MedImmune's Petition for Access to Settlement Agreement, Aug. 1, 2002 (Int. No. 102,572).
Curriculum Vitae of Art Riggs (Int. No. 102,572).
Proposal to Genentech re: funding for IgG (Bates Nos. 0921–0926) (Int. No. 102,572).
Curriculum Vitae of Jack Shively (Int. No. 102,572).
Curriculum Vitae of Ron Wetzel (Int. No. 102,572).
Curriculum Vitae of William Holmes (Int. No. 102,572).
Curriculum Vitae of Michael Rey (Int. No. 102,572).
Curriculum Vitae of Michael Mumford (Int. No. 102,572).
Curriculum Vitae of Shmuel Cabilly (Int. No. 102,572).
Cabilly Nbk (Bates Nos. 0970–0976, 0982–0987, 0989, 0991–0992, 0994–01001, 01013–01014) (Int. No. 102,572).
Interference Initial Memorandum (Int. No. 104,532).
Glaxo Wellcome Inc.'s Observations, Apr. 18, 2001 (Int. No. 104,532).
Glaxo Wellcome Inc. Miscellaneous Motion 10 (Suppress New Evidence Supporting Cabilly Reply 6), Apr. 18, 2001 (Int. No. 104,532).
Notice Declaring Interference, May 15, 2000 (Int. No. 104, 532).
Cabilly Notice of Real Party in Interest, May 25, 2000 (Int. No. 104,532).
Glaxo Wellcome Inc. Notice of Reap Party in Interest, May 26, 2000 (Int. No. 104,532).
Glaxo Wellcome Inc. Notice of Intent to File Preliminary Motions, Jul. 10, 2000 (Int. No. 104,532).
Glaxo Wellcome Inc. Notice of Related Litigation, Jul. 11, 2000 (Int. No. 104,532).
Glaxo Wellcome Inc. List of Preliminary Motions It Intends to File, Jul. 11, 2000 (Int. No. 104,532).
Cabilly List of Preliminary Motions, Jul. 11, 2000 (Int. No. 104,532).
Cabilly Notice, 37 C.F.R. § 1.660(d), Jul. 11, 2000 (Int. No. 104,532).
Glaxo Wellcome Inc. Miscellaneous Motion 1 (with attachments), Sep. 28, 2000 (Int. No. 104,532).
Glaxo Wellcome Reply to Opposition to Miscellaneous Motion 1, Oct. 10, 2000 (Int. No. 104,532).
Order Denying Glaxo Wellcome Inc. Miscellaneous Motion 1, Oct. 18, 2000 (Int. No. 104,532).
Order Regarding Discovery, Oct. 26, 2000 (Int. No. 104, 532).
Cabilly Preliminary Motion 1, Nov. 1, 2000 (Int. No. 104, 532).
Cabilly Preliminary Motion 2, Nov. 1, 2000 (Int. No. 104, 532).
Cabilly Preliminary Motion 3, Nov. 1, 2000 (Int. No. 104, 532).
Cabilly Preliminary Motion 4, Nov. 1, 2000 (Int. No. 104, 532).
Cabilly Preliminary Motion 5, Nov. 1, 2000 (Int. No. 104, 532).
Cabilly Preliminary Motion 6, Nov. 1, 2000 (Intl. No. 104, 532).
Cabilly Preliminary Motion 7, Nov. 13, 2000 (Int. No. 104, 532).
Cabilly Preliminary Motion 8, Nov. 13, 2000 (Int. No. 104, 532).
Cabilly Preliminary Motion 9, Nov. 13, 2000 (Int. No. 104, 532).
Letter Regarding Error in Notice Declaring Interference, Nov. 1, 2000 (Int. No. 104,532).
Glaxo Wellcome, Inc.'s Preliminary Motion 1, Nov. 1, 2000 (Int. No. 104,532).
Glaxo Wellcome, Inc.'s Preliminary Motion 2, Nov. 1, 2000 (Int. No. 104,532).
Glaxo Wellcome, Inc.'s Preliminary Motion 3, Nov. 1, 2000 (Int. No. 104,532).
Glaxo Wellcome, Inc.'s Preliminary Motion 4, Nov. 1, 2000 (Int. No. 104,532).
Glaxo Wellcome, Inc.'s Preliminary Motion 5, Nov. 1, 2000 (Int. No. 104,532).
Glaxo Wellcome, Inc.'s Preliminary Motion 6, Nov. 1, 2000 (Int. No. 104,532).

Glaxo Wellcome, Inc.'s Preliminary Motion 7, Nov. 1, 2000 (Int. No. 104,532).
Glaxo Wellcome, Inc.'s Preliminary Motion 8, Nov. 1, 2000 (Int. No. 104,532).
Glaxo Wellcome, Inc.'s Preliminary Motion 9, Nov. 1, 2000 (Int. No. 104,532).
Glaxo Wellcome, Inc.'s Preliminary Motion 10, Nov. 1, 2000 (Int. No. 104,532).
Glaxo Wellcome, Inc.'s Preliminary Motion 11, Nov. 1, 2000 (Int. No. 104,532).
Glaxo Wellcome, Inc.'s Preliminary Motion 12, Nov. 1, 2000 (Int. No. 104,532).
Glaxo Wellcome, Inc.'s Preliminary Motion 13, Nov. 1, 2000 (Int. No. 104,532).
Glaxo Wellcome, Inc.'s Preliminary Motion 14, Nov. 1, 2000 (Int. No. 104,532).
Glaxo Wellcome Inc. Preliminary Statement, Nov. 8, 2000 (Int. No. 104,532).
Cabilly Preliminary Statement, Nov. 1, 2000 (Int. No. 104,532).
Glaxo Wellcome Objection to Admissibility of Evidence, Nov. 8, 2000 (Int. No. 104,532).
Cabilly Objection to Evidence, Nov. 13, 2000 (Int. No. 104,532).
Cabilly Miscellaneous Motion 1 (Motion for Permission to Issue a Subpoena, 35 U.S.C. § 24), Dec. 8, 2000 (Int. No. 104,532).
Opposition to Cabilly Miscellaneous Motion 1, Dec. 15, 2000 (Int. No. 104,532).
Decision Granting Cabilly Miscellaneous Motion 1, Dec. 20, 2000 (Int. No. 104,532).
Glaxo Wellcome Inc. Objection to Admissibility of Evidence Dec. 20, 2000 (Int. No. 104,532).
Cabilly Reply to Opposition to Cabilly Miscellaneous Motion 1, Dec. 20, 2000 (Int. No. 104,532).
Cabilly Response to Objections to Admissibility of Evidence, Jan. 16, 2001 (Int. No. 104,532).
Glaxo Wellcome Miscellaneous Motion 2, Jan. 16, 2001 (Int. No. 104,532).
Glaxo Wellcome Miscellaneous Motion 3, Jan. 16, 2001 (Int. No. 104,532).
Glaxo Response to Cabilly's Objection to Evidence, Jan. 16, 2001 (Int. No. 104,532).
Cabilly Opposition 1, Feb. 2, 2001 (Int. No. 104,532).
Cabilly Opposition 2, Feb. 2, 2001 (Int. No. 104,532).
Cabilly Opposition 3, Feb. 2, 2001 (Int. No. 104,532).
Cabilly Response to Glaxo Motion 4, Feb. 2, 2001 (Int. No. 104,532).
Cabilly Opposition 5, Feb. 2, 2001 (Int. No. 104,532).
Cabilly Opposition 6, Feb. 2, 2001 (Int. No. 104,532).
Cabilly Opposition 7, Feb. 2, 2001 (Int. No. 104,532).
Cabilly Opposition 8, Feb. 2, 2001 (Int. No. 104,532).
Cabilly Opposition 9, Feb. 2, 2001 (Int. No. 104,532).
Cabilly Opposition 10, Feb. 2, 2001 (Int. No. 104,532).
Cabilly Opposition 11, Feb. 2, 2001 (Int. No. 104,532).
Cabilly Opposition 12, Feb. 2, 2001 (Int. No. 104,532).
Cabilly Opposition 13, Feb. 2, 2001 (Int. No. 104,532).
Cabilly Opposition 14, Feb. 2, 2001 (Int. No. 104,532).
Glaxo Wellcome Inc. Objection to Admissibility of Evidence, Jan. 23, 2001 (Int. No. 104,532).
Order Denying Glaxo Motions Miscellaneous Motions 1 and 2, Jan. 29, 2001 (Int. No. 104,532).
Glaxo Miscellaneous Motion 4, Feb. 2, 2001 (Int. No. 104,532).
Glaxo Miscellaneous Motion 5, Feb. 2, 2001 (Int. No. 104,532).
Glaxo Opposition to Motion 6, Feb. 2, 2001 (Int. No. 104,532).
Glaxo Wellcome Miscellaneous Motion 6 (Correct Opp. No. 3), Mar. 9, 2001 (Int. No. 104,532).
Glaxo Wellcome Miscellaneous Motion 7 (Correct Opp. No. 5), Mar. 9, 2001 (Int. No. 104,532).
Glaxo Wellcome Miscellaneous Motion 8 (Correct Opp. No. 6), Mar. 9, 2001 (Int. No. 104,532).
Glaxo Wellcome Inc.'s Miscellaneous Motion No. 9, Mar. 16, 2001 (Int. No. 104,532).
Glaxo Opposition to Motion 1, Feb. 2, 2001 (Int. No. 104,532).
Glaxo Opposition to Motion 2, Feb. 2, 2001 (Int. No. 104,532).
Glaxo Opposition to Motion 3, Feb. 2, 2001 (Int. No. 104,532).
Glaxo Opposition to Motion 4, Feb. 2, 2001 (Int. No. 104,532).
Glaxo Opposition to Motion 5, Feb. 2, 2001 (Int. No. 104,532).
Glaxo Wellcome's Supplemental Opposition to Cabilly's Preliminary Motion 6, May 5, 2001 (Int. No. 104,532).
Glaxo Opposition to Motion 7, Feb. 2, 2001 (Int. No. 104,532).
Glaxo Opposition to Motion 8, Feb. 2, 2001 (Int. No. 104,532).
Glaxo Opposition to Motion 9, Feb. 2, 2001 (Int. No. 104,532).
Cabilly Response to Glaxo Miscellaneous Motion 4, Feb. 8, 2001 (Int. No. 104,532).
Glaxo Wellcome Inc. Objection to Admissibility of Evidence, Feb. 9, 2001 (Int. No. 104,532).
Order Granting Glaxo Miscellaneous Motion 4, Feb. 13, 2001 (Int. No. 104,532).
Order Authorizing Deposition Testimony, Mar. 5, 2001 (Int. No. 104,532).
Cabilly Reply 1, Mar. 27, 2001 (Int. No. 104,532).
Cabilly Reply 2, Mar. 27, 2001 (Int. No. 104,532).
Cabilly Reply 3, Mar. 27, 2001 (Int. No. 104,532).
Cabilly Reply 4, Mar. 27, 2001 (Int. No. 104,532).
Cabilly Reply 5, Mar. 27, 2001 (Int. No. 104,532).
Cabilly Reply 6, Mar. 27, 2001 (Int. No. 104,532).
Cabilly Reply 7, Mar. 27, 2001 (Int. No. 104,532).
Cabilly Reply 8, Mar. 27, 2001 (Int. No. 104,532).
Cabilly Reply 9, Mar. 27, 2001 (Int. No. 104,532).
Glaxo Reply 1, Mar. 27, 2001 (Int. No. 104,532).
Glaxo Reply 2, Mar. 27, 2001 (Int. No. 104,532).
Glaxo Reply 3, Mar. 27, 2001 (Int. No. 104,532).
Glaxo Reply 4, Mar. 27, 2001 (Int. No. 104,532).
Glaxo Reply 5, Mar. 27, 2001 (Int. No. 104,532).
Glaxo Reply 6, Mar. 27, 2001 (Int. No. 104,532).
Glaxo Reply 7, Mar. 27, 2001 (Int. No. 104,532).
Glaxo Reply 8, Mar. 27, 2001 (Int. No. 104,532).
Glaxo Reply 9, Mar. 27, 2001 (Int. No. 104,532).
Glaxo Reply 11, Mar. 27, 2001 (Int. No. 104,532).
Glaxo Reply 14, Mar. 27, 2001 (Int. No. 104,532).
Order Granting Glaxo Wellcome Inc. Miscellaneous Motions, Apr. 2, 2001 (Int. No. 104,532).
Cabilly Response to Objection to Admissibility of Evidence, Feb. 22, 2001 (Int. No. 104,532).
Glaxo Wellcome Inc. Objection to Admissibility of Evidence, Apr. 3, 2001 (Int. No. 104,532).

Transcript of teleconference with APJ on Apr. 5, 2001 (Int. No. 104,532).
Order Authorizing Glaxo Supplemental Opposition 6, Apr. 6, 2001 (Int. No. 104,532).
Cabilly Motion to Suppress, 37 C.F.R. § 1.656(h), Apr. 18, 2001 (Int. No. 104,532).
Glaxo Wellcome Inc.'s Request for Defer Decision on Motions Until Final Hearing or to Permit the Filing of Briefs, Apr. 18, 2001 (Int. No. 104,532).
Glaxo Wellcome Inc.'s Miscellaneous Motion 11(Suppression of Certain Deposition Exhibits and Deposition Testimony), Apr. 18, 2001 (Int. No. 104,532).
Glaxo Wellcome Inc.'s Miscellaneous Motion 12 (Suppression of Deposition Testimony), Apr. 18, 2001 (Int. No. 104,532).
Glaxo Wellcome Inc.'s Notice of Change of Real Party in Interest, Apr. 19, 2001 (Int. No. 104,532).
Petition from the Apr. 6, 2001 Order of the APJ Under 37 C.F.R. 1.644(a)(1), Apr. 20, 2001 (Int. No. 104,532).
Memorandum Opinion and Order, Apr. 30, 2001 (Int. No. 104,532).
Order Regarding Glaxo Wellcome Inc. Motions, May 2, 2001 (Int. No. 104,532).
Cabilly's Opposition to Glaxo Miscellaneous Motion 10, May 2, 2001 (Int. No. 104,532).
Cabilly's Opposition to Glaxo Wellcome Misc. Motion 11, May 2, 2001 (Int. No. 104,532).
Cabilly's Opposition to Glaxo Wellcome Misc. Motion 12, May 2, 2001 (Int. No. 104,532).
Glaxo Wellcome Inc.'s Opposition to Cabilly Motion to Suppress (With exhibits attached), May 2, 2001 (Int. No. 104,532).
Cabilly's Reply to Glaxo's Supplemental Opposition to Preliminary Motion 6, Jun. 1, 2001 (Int. No. 104,532).
Glaxo Wellcome Objection to Admissibility of Evidence, Jun. 8, 2001 (Int. No. 104,532).
Glaxo Wellcome's Reply to Cabilly's Opposition to Misc. Motion 10, Jul. 2, 2001 (Int. No. 104,532).
Glaxo Wellcome's Reply to Cabilly's Oppositions to Misc. Motion 11, Jul. 2, 2001 (Int. No. 104,532).
Glaxo Wellcome's Reply to Cabilly's Oppositions to Misc. Motion 12, Jul. 2, 2001 (Int. No. 104,532).
Cabilly Reply to the Opposition to It's Motion to Suppress Evidence, Jul. 2, 2001 (Int. No. 104,532).
Submission of Transcript of Oral Hearing Held Sep. 18, 2001, Sep. 24, 2001 (Int. No. 104,532).
Order Making Visual Aid of Record, Sep 27, 2001 (Int. No. 104,532).
Order Regarding Filing of Glaxo Supplemental Evidence, Nov. 13, 2001 (Int. No. 104,532).
Glaxo Wellcome Inc.'s Submission of Late Evidence, Nov. 15, 2001 (Int. No. 104,532).
Cabilly Motion to Suppress, Nov. 20, 2001 (Int. No. 104,532).
Glaxo Wellcome Inc.'s Opposition to Cabilly Motion to Suppress, Nov. 21, 2001 (Int. No. 104,532).
Cabilly Reply to Glaxo Opposition to Motion To Suppress, Nov. 27, 2001 (Int. No. 104,532).
Decision on Preliminary and Other Motions and Final Judgment, Sep. 4, 2002 (Int. No. 104,532).
Cabilly Exhibit List (Int. No. 104,532).
Notice of Allowability, Paper No. 21 dated Jun. 13, 1995 in U.S. Appl. No. 08/155,864 (Exhibit 1006; Int. No. 104,532).
Notice of Allowability, Paper No. 9 dated Jun. 7, 1995 in U.S. Appl. No. 08/335,400 (Exhibit 1007; Int. No. 104,532).
Notice of Allowability, Paper No. 9 dated Jun. 8, 1995 in U.S. Appl. No. 08/335,401 (Exhibit 1008; Int. No. 104,532).
Declaration of Stephen V. Desiderio, M.D., Ph.D. (Exhibit 1028; Int. No. 104,532).
Declaration of Sharon S. Krag, Ph.D. (Exhibit 1029; Int. No. 104,532).
Declaration of John E. Shively, Ph.D. (Exhibit 1030; Int. No. 104,532).
Activase™ 7 (Alteplase) package insert dated Jun. 1988 (Exhibit 1033; Int. No. 104,532).
Declaration of James Scott Crowe, Paper No. 16, received in executed form in Group 1800 on Nov. 17, 1994 in U.S. Appl. No. 08/155,864 (Exhibit 1034; Int. No. 104,532).
Declaration of Robert Lifely, Paper No. 10, received in executed form in Group 1800 on Apr. 12, 1994 in U.S. Appl. No. 08/155,864 (Exhibit 1035; Int. No. 104,532).
Declaration of Geoffrey Hale, Paper No. 16, received in executed form in Group 1800 on Nov. 17, 1994 in U.S. Appl. No. 08/155,864 (Exhibit 1036; Int. No. 104,532).
Curriculum Vitae of John E. Shively, Ph.D. (Exhibit 1039; Int. No. 104,532).
Curriculum Vitae of Stephen V. Desiderio, M.D., Ph.D. (Exhibit 1040; Int. 104,532).
Curriculum Vitae of Sharon S. Krag, Ph.D. (Int. 104,532).
Citation of Information, dated Sep. 6, 1995 in U.S. Appl. No. 08/335,400 (Exhibit 1049; Int. No. 104,532).
Citation of Information, Paper No. 14 dated Sep. 6, 1995 in U.S. Appl. No. 08/335,401 (Exhibit 1050; Int. No. 104,532).
Examiner Communication, Paper No. 30 dated May 16, 1996 in U.S. Appl. No. 08/155,864 (Exhibit 1051; Int. No. 104,532).
Examiner Communication dated Dec. 29, 1995 in U.S. Appl. No. 08/335, 400 (Exhibit 1052; Int. No. 104,532).
Examiner Communication, Paper No. 15 dated Jan. 5, 1996 in U.S. Appl. No. 08/335,401 (Exhibit 1053; Int. No. 104,532).
Office Action dated Mar. 10, 1992, Paper No. 5 in U.S. Appl. No. 07/770,730, filed Oct. 16, 1991 (Exhibit 1057; Int. No. 104,532).
Preliminary Amendment, Paper No. 9 in U.S. Appl. No. 08/155,864, filed Nov. 23, 1993 in U.S. Appl. No. 08/155,864, filed Nov. 23, 1993.
Preliminary Amendment of Mar. 30, 1994 submitted in U.S. Appl. No. 08/155,864 (Exhibit 1058; Int. No. 104,532).
Declaration of Robert Lifely, submitted in U.S. Appl. No. 08/155,864, dated Jun. 4, 1994 (Exhibit 1059; Int. No. 104,532).
Preliminary Communication, Paper No. 15, received in Group 1800 on Nov. 17, 1994 in U.S. Appl. No. 08/155,864 (Exhibit 1060; Int. No. 104,532).
Declaration of Geoffrey Hale, submitted in U.S. Appl. No. 08/155,864, dated Nov. 16, 1994 (Exhibit 1062; Int. No. 104,532).
Amendment in U.S. Appl. No. 08/155,864 dated Feb. 28, 1995 (Exhibit 1063; Int. No. 104,532).
Office Action dated Jan. 6, 1995, Paper No. 4 in U.S. Appl. No. 08/335,400, filed Nov. 3, 1994 (Exhibit 1064; Int. No. 104,532).
Amendment of May 8, 1995 submitted in U.S. Appl. No. 08/335,400 (Exhibit 1065; Int. No. 104,532).

Office Action dated Jan. 11, 1995, Paper No. 4 in U.S. Appl. No. 08/335,401, filed Nov. 3, 1994 (Exhibit 1066; Int. No. 104,532).
Amendment dated May 8, 1995, Paper No. 7 in U.S. Appl. No. 08/335,400 to Page (Exhibit 1067; Int. No. 104,532).
Second Declaration of Sharon S. Krag, Ph.D. (Exhibit 1071; Int. No. 104,532).
Third Declaration of Sharon S. Krag, Ph.D. (Exhibit 1075; Int. No. 104,532).
Amendment filed in U.S. Appl. No. 08/909,611 (Exhibit 1081; Int. No. 104,532).
Declaration of Steven B. Kelber (Exhibit 1085; Int. No. 104,532).
Protocol UAC 180 of the University of Alabama's Comprehensive Cancer Center, describing Clinical Phase I trials conducted over the period Nov. 1989 through Oct. 1990. (See in particular, § 5.1, p. 9.) (Exhibit 1090; Int. No. 104,532).
Data Report for Protocol UAC 180 dated Aug. 24, 1990: Patient data collected after administration of cB72.3 monoclonal antibody (Exhibit 1093; Int. No. 104,532).
Status Report: Phase I Contract Cancer Therapy Evaluation Program No1–CM–97611 dated Feb. 4, 1991 (pp. 1–12) (Exhibit 1094; Int. No. 104,532).
James Scott Crowe Deposition Transcript (Exhibit 1100; Int. No. 104,532).
Methods in Enzymology, vol. 101, Part C, Table of Contents, p. v–viii (Exhibit 1101; Int. No. 104,532).
Yarranton Deposition Transcript and Supporting Exhibits (Exhibit 1112; Int. No. 104,532).
Second Declaration of Stephen V. Desiderio, M.D., Ph.D. (Exhibit 1113; Int. No. 104,532).
LoBuglio Deposition Transcript (Exhibit 1114; Int. No. 104,532).
Fourth Declaration of Sharon S. Krag, Ph.D. (Exhibit 1117; Int. No. 104,532).
Deposition Transcript of Ellen Vitetta, Jan. 8, 2001 (Exhibit 1120; Int. No. 104,532).
Deposition Transcript of Richard Youle Jan. 3, 2001 (Exhibit 1121; Int. No. 104,532).
Third Declaration of Stephen V. Desiderio, M.D., Ph.D. (Exhibit 1122; Int. No. 104,532).
Deposition Transcript of Sharon Krag Jan. 5, 2001 (Exhibit 1123; Int. No. 104,532).
Deposition Transcript of Stephen Desiderio Dec. 28, 2000 (Exhibit 1125; Int. No. 104,532).
ATCC deposit verification for CEA.66–E3—(Exhibit 1126; Int. No. 104,532).
Chart Entitled "A Human Leucocyte Surface Markers by Immunotech" (Exhibit 1127; Int. No. 104,532).
Excerpts from Prosecution File History of 5,545,403 (U.S. Appl. No. 08/155,864) (not entire file history) (Exhibit 1154; Int. No. 104,532).
Excerpts from Prosecution File History of 5,545,404 (U.S. Appl. No. 08/355,400) (not entire file history) (Exhibit 1155; Int. No. 104,532).
Transcript from Second Deposition of Robert Lifely, Ph.D. (Exhibit 1165; Int. No. 104,532).
Transcript from Deposition of Nicholas Rapson, Ph.D. (Exhibit 1166; Int. No. 104,532).
Transcript from Second Deposition of James Scott Crowe, Ph.D. (Exhibit 1167; Int. No. 104,532).
Transcript from Second Deposition of Richard Youle, Ph.D. (Exhibit 1168; Int. No. 104,532).
Deposition of Vitetta Mar. 18, 2001 (Exhibit 1169; Int. No. 104,532).
Transcript from Second Deposition of Sharon Krag, Ph.D. (Exhibit 1171; Int. No. 104,532).
Deposition Transcript of Mark Sydenham (Exhibit 1172; Int. No. 104,532).
Excerpts from Prosecution File History of U.S. Appl. No. 08/155,864 (Exhibit 1173; Int. No. 104,532).
Declaration of Vladimir Drozdoff, Ph.D. (Exhibit 1174; Int. No. 104,532).
Verdict—United States District Court, District of Delaware (Exhibit 1175; Int. No. 104,532).
Ellen Vitetta Deposition Transcript, May 21, 2001 (Exhibit 1176; Int. No. 104,532).
Linda Thurmond Deposition Transcript, May 18, 2001 (Exhibit 1179; Int. No. 104,532).
Glaxo Wellcome Inc. Exhibit List (Int. No. 104,532).
Office Action dated May 27, 1999 from Cabilly's U.S. Appl. No. 08/909,611 (Paper 14) (Exhibit 2001; Int. No. 104,532).
Declaration of John Ridgway dated Jun. 17, 1999 (with attached Exhibit A) from Cabilly's U.S. Appl. No. 08/908,611 (Paper 15) (Exhibit 2002; Int. No. 104,532).
Interview Summary dated Jun. 22, 1999 from Cabilly's U.S. Appl. No. 08/909,611 (Paper 16) (Exhibit 2003; Int. No. 104,532).
Interview Summary dated Jul. 12, 1999 from Cabilly's U.S. Appl. No. 08/909,611 (Paper 17) (Exhibit 2004; Int. No. 104,532).
Office Action dated Mar. 2, 2000 from Cabilly's U.S. Appl. No. 08/909,611 (Paper 18) (Exhibit 2005; Int. No. 104,532).
Headings in the Cabilly Application (Exhibit 2010; Int. No. 104,532).
Curriculum Vitae of Dr. Richard Youle (Exhibit 2011; Int. No. 104,532).
Declaration 1 of Dr. Richard Youle (Exhibit 2012; Int. No. 104,532).
CD Molecules printout ("Human cell surface molecule recognized by the International Workshops on Human Leukocyte Differentiation Antigens"), Protein Reviews on the Web (Exhibit 2018; Int. No. 104,532).
Vitetta Declaration 1 (Dr. Ellen Vitetta) (Exhibit 2028; Int. No. 104,532).
Lifely Declaration with Exhibits dated Apr. 6, 1994 (Exhibit 2033; Int. No. 104,532).
Medline Abstracts regarding rat anti–CDw52 therapeutic antibodies (Exhibit 2051; Int. No. 104,532).
File History of Page's U.S. Appl. No. 07/777,730, filed Oct. 16, 1991 (Exhibit 2056; Int. No. 104,532).
Curriculum Vitae of Dr. Ellen Vitetta (Exhibit 2058; Int. No. 104,532).
Medline Abstracts regarding murine anti–CD4 therapeutic antibodies (Exhibit 2064; Int. No. 104,532).
Crowe Declaration with Exhibits (Exhibit 2088; Int. No. 104,532).
Cabilly Claims Corresponding to the Count (Exhibit 2096; Int. No. 104,532).
Availability of CEA.66–E3 (Exhibit 2097; Int. No. 104,532).
Declaration 2 of Dr. Richard Youle (Exhibit 2098; Int. No. 104,532).
EPO Communication dated Jun. 2, 1987 during prosecution of Cabilly et al. European Application No. 84302368.0–2105 (Exhibit 2111; Int. No. 104,532).

Jan. 29, 1987 response of Cabilly et al. filed before EPO during prosecution of Cabilly et al. European Application No. 84302368.0–2105 (Exhibit 2112; Int. No. 104,532).
Search results of ATCC product listing of deposited cell lines (Exhibit 2114; Int. No. 104,532).
Legal Analysis Concerning Written Description (Exhibit 2126; Int. No. 104,532).
Amendment dated May 8, 1995, Paper No. 7 in U.S. Appl. No. 08/335,400 (Exhibit 2133; Int. No. 104,532).
Amendment of May 11, 1995 submitted in U.S. Appl. No. 08/335,401 (Exhibit 2134; Int. No. 104,532).
Genentech, Inc.'s released product sales for Rituxan (Exhibit 2139; Int. No. 104,532).
Genentech Reports 25 Percent Increase in Product Sales for Third Quarter (from Genentech web site) (Exhibit 2140; Int. No. 104,532).
Genentech Reports 1999 Year–End Results (from Genentech web site) (Exhibit 2141; Int. No. 104,532).
Cancer data sheet from the National Cancer Institute "CancerNet" internet site (Exhibit 2142; Int. No. 104,532).
FDA Product Description Sheet (Exhibit 2143; Int. No. 104,532).
Datasheet on CD52 from Workshop on Leukocyte Antigens (Exhibit 2146; Int. No. 104,532).
Declaration 3 of Dr. Richard Youle (Exhibit 2148; Int. No. 104,532).
Declaration 4 of Dr. Richard Youle (Exhibit 2130; Int. No. 104,532).
Datasheet on CD4 from Workshop on Leukocyte Antigens (Exhibit 2151; Int. No. 104,532).
File History of Page's U.S. Appl. No. 07/943,146, filed Sep. 10, 1992 (Exhibit 2149; Int. No. 104,532).
File History of Page's U.S. Appl. No. 08/046,893, filed Apr. 15, 1993 (Exhibit 2150; Int. No. 104,532).
Request for Admissions 1–11—Rituxan (Exhibit 2155; Int. No. 104,532).
Herceptin—description sheets (4 pages) (Exhibit 2156; Int. No. 104,532).
Vitetta Declaration 2 (Exhibit 2157; Int. No. 104,532).
Youle Declaration 5 (Exhibit 2159; Int. No. 104,532).
Mark Sydenham Declaration (Exhibit 2160; Int. No. 104,532).
Declaration 2 of J. Scott Crowe (Exhibit 2161; Int. No. 104,532).
Robinson's U.S. Appl. No. 09/021,934, filed Feb. 12, 1998 and selected papers from the file wrapper (Exhibit 2162; Int. No. 104,532).
Hale Declaration (Exhibit 2167; Int. No. 104,532).
Youle Declaration 6 (Exhibit 2169; Int. No. 104,532).
Deposition Transcript of Ellen Vitetta, Ph.D., Jan. 8, 2001 (Exhibit 2170; Int. No. 104,532).
Deposition Transcript of James S. Crowe Dec. 14, 2000 (Exhibit 2171; Int. No. 104,532).
VS Form 16–6A—U.S. Veterinary Permit for Importation and Transportation of Controlled Materials and Organisms and Vectors—Permit No. 27899—Date Issued: Nov. 8, 1991—Re: Campath 1H Monoclonal Antibody (Exhibit 2172; Int. No. 104,532).
Internal Notice of Shipment of Campath 1H May 10, 1990 (Exhibit 2173; Int. No. 104,532).
Deposition Transcript of Stephen V. Desiderio, Dec. 28, 2000 (Exhibit 2177; Int. No. 104,532).
Deposition Transcript of Mark Robert Lifely Jan. 9, 2000 (Exhibit 2180; Int. No. 104,532).
Deposition Transcript of John Shively Jan. 12, 2001 (Exhibit 2181; Int. No. 104,532).
Cabilly Claims 53–67 (Exhibit 2184; Int. No. 104,532).
Mar. 6, 1989 Memorandum from Jeffrey M. Johnston, M.D. Re: Campath and Rheumatoid Arthritis Overview Medical Position (Exhibit 2191; Int. No. 104,532).
Mar. 28, 1989—Lab Meeting—handwritten notes—First Mention of Campath–1H, 3 pages (Exhibit 2190; Int. No. 104,532).
Jul. 13, 1989—handwritten notes—4 pages (Exhibit 2192; Int. 104,532).
Jun. 11, 1990—Laboratory Notebook 90/0522, Iodination of C–I H (Exhibit 2193; Int. No. 104,532).
CV of Linda Thurmond (Exhibit 2194; Int. No. 104,532).
CV of Mark Sydenham (Exhibit 2195; Int. No. 104,532).
131 Declaration of Rapson (Exhibit 2196; Int. No. 104,532).
131 Declaration of Thurmond (Exhibit 2197; Int. No. 104,532).
Declaration 4 of James Scott Crowe (Exhibit 2198; Int. No. 104,532).
P73 Campath–IH Project Team Meeting Minutes—Feb. 6, 1990 (Exhibit 2199; Int. No. 104,532).
Laboratory Notebook (Exhibit 2201; Int. No. 104,532).
Laboratory Notebook (Exhibit 2202; Int. No. 104,532).
Laboratory Notebook (Exhibit 2203; Int. No. 104,532).
Laboratory Notebook—May 23, 1990–Oct. 12, 1990 (Exhibit 2200; Int. No. 104,532).
Laboratory Notebook—Nov. 27, 1991–Dec. 4, 1991 (Exhibit 2204; Int. No. 104,532).
Laboratory Notebook (Exhibit No. 2205; Int. No. 104,532).
Laboratory Notebook (Exhibit No. 2206; Int. No. 104,532).
Laboratory Notebook (Exhibit 2207; Int. No. 104,532).
Laboratory Notebook (Exhibit 2208; Int. No. 104,532).
Laboratory Notebook (Exhibit 2209; Int. No. 104,532).
Laboratory Notebook (Exhibit 2210; Int. No. 104,532).
Laboratory Notebook (Exhibit 2211; Int. No. 104,532).
Laboratory Notebook (Exhibit 2212; Int. No. 104,532).
Laboratory Notebook (Exhibit 2213; Int. No. 104,532).
Laboratory Notebook (Exhibit 2214; Int. No. 104,532).
Laboratory Notebook (Exhibit 2215; Int. No. 104,532).
Laboratory Notebook (Exhibit 2216; Int. No. 104,532).
Laboratory Notebook (Exhibit 2217; Int. No. 104,532).
CV of James S. Crowe (Exhibit 2218; Int. No. 104,532).
Vitetta Declaration 3 (Exhibit 2220; Int. No. 104,532).
Jul. 13, 1989 Memorandum from Jeffrey M. Johnston to Research Committee RE: Campath–1H: A Humanized Anti–lymphocyte monoclonal antibody (Exhibit 2221; Int. No. 104,532).
Thurmond Personal Notebook Entry for Jun. 26, 1989 (Exhibit 2224; Int. No. 104,532).
Thurmond Personal Notebook Entry for Oct. 17, 1994 (Exhibit 2225; Int. No. 104,532).
Youle Declaration 7 (Exhibit 2234; Int. No. 104,532).
Herceptin description sheets from Genentech web site (16 pages) (Exhibit 2235; Int. No. 104,532).
Rituxan description sheets from Genentech web site (11 pages) (Exhibit 2236; Int. No. 104,532).
Reuters news article and San Francisco Chronicle News article (Exhibit 2241; Int. No. 104,532).
Results of Medline search of "therapeutic antibodies" years 1966–1990 (Exhibit 2242; Int. No. 104,532).
Vitetta Declaration 4 (Exhibit 2243; Int. No. 104,532).
Certificate of Correct Inventorship U.S. Patent No. 5,545,405, Jun. 17, 1997 (Exhibit 2245; Int. No. 104,532).

Declaration of Mary Anne Armstrong (Exhibit 2249; Int. No. 104,532).
Declaration of Jeffrey J. Berns (Exhibit 2250; Int. No. 104, 532).
Library of Congress Online Catalog record for Cabilly Exhibit 1074 (Exhibit 2251; Int. No. 104,532).
Library of Congress Online Catalog record for Cabilly Exhibit 1073 (Exhibit 2256; Int. No. 104,532).
National Library of Medicine PubMed Medline record for Cabilly Exhibit 1074 (Exhibit 2252; Int. No. 104,532).
Oct. 17, 1994 Teleconference on Campath Long Term Follow Up (handwritten sheet and translation page) (Exhibit 2253; Int. No. 104,532).
Declaration 3 of Crowe (Exhibit 2254; Int. No. 104,532).
Declaration 2 of Jeffrey J. Berns (Exhibit 2255; Int. No. 104,532).
Excerpts from 21 C.F.R. (Exhibit 2270; Int. No. 104,532).
Vitetta Declaration 5 (Exhibit 2271; Int. No. 104,532).
Supplemental 131 Declaration of Thurmond (Exhibit 2272; Int. No. 104,532).
Horne v. Patton (Exhibit 2273; Int. No. 104,532).
Office Action in U.S. Appl. No. 08/046,893 to Page dated Jun. 23, 1993 (Exhibit 2274; Int. No. 104,532).
Letter dated Apr. 20, 2001 from Jean Harney to Jerry Murphy (Exhibit 2277; Int. No. 104,532).
Excerpts from Lifely Lab notebook ZEIA/90/17 (Exhibit 2278; Int. No. 104,532).
Documents from EP 120694 file, namely Aug. 30, 1988 Celltech's request to amend the application and Jun. 15, 1990 Minutes of the Oral Proceedings.
Declaration of Michael Francis Tuite with CV attached) (May 26, 1995) (EP 120694).
Declaration of Atsuo Ochi (CV attached. Regarding EP 120694 and EP 125023 oppositions)(May 17, 1996).
Declaration of Gabrielle L. Boulianne(Exhibits A–C attached. Regarding EP 120694 and EP 125023 oppositions.) (May 15, 1996).
Minutes from the EP 120694 oral proceedings (Aug. 13, 1996).
Interlocutory Decision in Opposition Proceedings (Article 106(3)EPC) (EP 120694) (Feb. 14, 1997).
Decision of PCR EP 0200362 and decision of PCR EP 0201184. Sections 5 only. Submitted by PDL on Mar. 27, 1997 (Dec. 14, 1995) (EP 120694).
Reasons for the Decision of T612/92 and T694/92. Submitted by PDL on Mar. 27, 1997 (EP 120694).
Appeal No. T400/97–344, Appellant: Genentech, Inc. European Patent No. 120694 (Celltech), European Patent Application No. 84301996.9, Grounds of Appeal (Apr. 1, 1997 Notice of Appeal attached) (Jun. 13, 1997).
Papers relevant to the interpretation of Ellison et al. PNAS 79:1984–1988(1982), Fig. 2 from Ellison paper and pp. 203 & 211 from New England Biolabs Catalog with Ellison paper attached. Ellison paper already cited previously (EP 120694).
European Patent Office communication with copy of EP 120694 maintained patent in amended form (Oct. 17, 2001).
Decision to Maintain the European Patent in Amended Form (Article 102(3) EPC) (Regarding EP 120694) (Mar. 14, 2002).
Jan. 29, 1987 response of Cabilly et al. filed before EPO during prosecution of Cabilly et al. European Application No. 84302368.0–2105 (EP 125023).
Jun. 2, 1987 Communication from EPO Examiner during prosecution of Cabilly et al. European Application No. 84302368.0–2105 (EP 125023).
Opposition to EP 125023 B of Genentech, Patentee's Response to the Opponents' Arguments (Feb. 22, 1993).
Response on behalf of the Patentees to the Further Submissions filed on behalf of Opponents I and IV in connection with Opposition Proceedings to EP–B–0125023 (84302368.0) (Aug. 9, 1994 Declaration of Leon R. Lyle with Exhibits A–B and Aug. 11, 1994 Affidavit of Allan Robert Adler with Exhibits A–E) (Oct. 31, 1995) (EP 125023).
Genentech's request for Opponent IV to provide the subject matter to be presented by Dr. Shulman at the oral proceedings (Mar. 3, 1997) (EP 125023).
Genentech's opposition to PDL's request to admit the entire Boss file as documentations at the oral proceedings (Mar. 18, 1997) (EP 125023).
Documents submitted by Genentech prior to oral proceedings (Mar. 27, 1997) (EP 125023).
Decision Revoking the European Patent (Article 102(1) EPC) (EP 125,023 with Minutes attached) (Oct. 16, 1997).
Appeal T1212/97–334 in Re Genentech EP–B–125023 Substantiation of the Proprietor's Appeal (Feb. 26, 1999).
Genentech's suggestions on the time frame of the oral proceedings (Nov. 18, 1999) (EP 125023).
Opposition to European Patent No. EP–B–0125023 (84302368.0–2106) (Genentech's submission prior to the oral proceedings with affidavit from Christopher Denison dated Apr. 19, 2000 and exhibits attached) (Apr. 20, 2000).
European Patent EP–B–125023 (Genentech, Inc.) Declaration of Dr. Richard Axel dated Apr. 18, 2000 with Exhibit A. Declaration of Paul J. Carter dated Apr. 20, 2000 with Exhibit A and ATCC letter (EP 125023).
Genentech's Submissions in Response to Board of Appeals' Feb. 2, 2000 Communication. Richard Axel's Apr. 18, 2000 Declaration with Exhibit A, Paul J. Carter's Apr. 20, 2000 Declaration with Exhibit A, ATCC letter, Walter Moore's Apr. 21, 2000 Statement and claim requests (Apr. 21, 2000) (EP 125023).
Minutes of the public oral proceedings before the Technical Board of Appeal 3.3.4 of May 22, 2000 (Regarding EP 120694) (May 22, 2000).
Statement By Walter Moore (Regarding the non–availability of the Herzenberg grant application) (Apr. 21, 2000).
Minutes of the public oral proceedings before the Technical Board of Appeal 3.3.4 of May 14, 2001 (EP 0125023) (May 14, 2001).
Decision of the Technical Board of Appeal 3.3.4 of May 14, 2001 (Regarding EP–B–125,023. Sep. 27, 2001 correction to the decision attached.) (May 14, 2001).
FDI Advisory 76–7, Procedure for Requests for Grant Applications and Progress Reports (May 19, 1976 Memo from the NIH Freedom of Information Coordinator at the US Department of Health, Education, and Welfare, and May 10, 1976 letter accompanying the memo) (May 1997).
Public Information Regulation (Paragraphs 5.71(c) and 5.72 (e)only), U.S. Department of Health, Education, and Welfare (Aug. 1974).
Slide entitled "18 Publications Discussing Chimeric Monoclonal Antibodies Before the 1987 Application", presented at Jury trial (2002).
Cabilly, S. (Letter from Shmuel Cabilly to Arthur D. Riggs) (Aug. 5, 1980) (ND Calif, Case No. C98–3926 MMC).

Genentech, Inc.'s Notice of Mot. and Mot. Summ. Adjudication on Diligence (Jul. 28, 2000), *Genentech, Inc.* v. *Celltech Therapeutics, Ltd.*, No. C98–3926 MMC, 2001 U.S. Dist. Lexis 3489 (N.D. Cal. Mar. 16, 2001).
Genentech, Inc.'s Decl. of Kate H. Murashige, Ph.D., *Genentech, Inc.* v. *Celltech Therapeutics, Ltd.*, No. C98–3926 MMC, 2001 U.S. Dist. Lexis 3489 (N.D. Cal. Mar. 16, 2001).
Response of Cabilly et al. filed before EPO during prosecution of Cabilly et al. European Application No. 84302368.0–2105 (Feb. 9, 1988).
Plaintiff MedImmune, Inc.'s First Amended Complaint, Demand for Jury Trial (U.S. District Court, Case No. 03–2567 MRP (CTX) *MedImmune, Inc.* vs. *Genentech, Inc., City of Hope, and Celltech R&D Ltd.*) (Aug. 13, 2003).
Joint Claim Construction Statement (Nov. 7, 2003).
Declaration of Dean G. Dunlavey in Support of Defendant Genentech, Inc.'s Opening Brief Regarding Claim Construction with Exhibits A–P (Dec. 22, 2003).
Joint Statement Responsive to Court's Jan. 28, 2004 Order re: Terms to be Construed at Markman Hearing (Feb. 9, 2004).
Defendant Genentech, Inc.'s Reply Brief Regarding Claim Construction (Feb. 13, 2004).
Supplemental Declaration of Dean G. Dunlavey in Support of Defendant Genentech, Inc.'s Reply Brief Regarding Claim Construction with Exhibit Q (Feb. 13, 2004).
MedImmune, Inc.'s Responses and Objections to Genentech, Inc.'s Second Set of Interrogatories (Feb. 24, 2004).
Deposition Transcript Exhibits 1–29 of Janet Hasak (Feb. 25, 2004).
Deposition Transcript of Exhibits 30–33 of Genentech through witness, Janet Hasak (Feb. 25, 2004).
Deposition Transcript of Genentech through witness, Janet Hasak (Feb. 25, 2004).
Deposition Transcript of Wendy M. Lee and Exhibits 34–47 (Mar. 4, 2004).
Deposition Transcript of Wendy M. Lee and Exhibits 48–60 (Mar. 5, 2004).
Curriculum Vitae of Jeanne Perry.
Reporter's Transcript, Motion to Dismiss, Monday (May 21, 2001).
Memorandum and Order (May 23, 2001).
Expert Report of Deborah L. French, Ph.D., with Exhibits A, B, C (Dec. 6, 2001).
Declaration of Lewis L. Lanier, Ph.D. with Exhibits A–B (Jan. 8, 2002).
Rebuttal Expert Report of Deborah L French, Ph.D. (Jan. 25, 2002).
Lanier deposition transcript (Feb. 14, 2002).
Harris deposition transcript (Feb. 27, 2002).
Transcript of Proceedings Before the Honorable Gregory G. Hollows United States Magistrate Judge Markman Hearing (Mar. 6, 2002) (vols. I–III).
Transcript of Proceedings Before the Honorable Gregory G. Hollows United States Magistrate Judge Markman Hearing (Mar. 7, 2002) (vol. II).
Genentech's Post–Hearing Markman Submission (Mar. 12, 2002).
Magistrate's Findings and Recommendations [Markman Hearing) (Mar. 20, 2002).
Genentech's Objections to Magistrate's Findings & Recommendations [Markman Hearing] (Apr. 1, 2002).
Genentech's Response to Chiron's Objection and Magistrate's Findings & Recommendations [Markman Hearing] Apr. 8, 2002), with attached Exhibits.
Memorandum and Order [Markman] (Apr. 22, 2002).
Genentech's Second Supplemental Response to Chiron's Interrogatory No. 25 (May 13, 2002).
Declaration of Lewis L. Lanier, Ph.D. in Support of Chiron's Oppositions to Genentech's Motions for Summary Judgment (May 20, 2002).
Declaration of William J. Harris, PH.D. in Support of Chiron's Replies to Summary Judgment Oppositions, with Exhibits A–D (May 27, 2002).
Genentech's Reply in Support of its Motion for Summary Judgment re Invalidity for Anticipation and Lack of Priority (May 28, 2002).
Reporter's Transcript, Motion to Preclude Admission of Undisclosed License Agreements and Cross Motions for Summary Judgment (Monday, Jun. 3, 2002).
Memorandum and Order re: Priority, Anticipation, Written Description, Enablement, Best Mode, Utility (Jun. 24, 2002).
Supplemental Expert Report of Deborah L. French Ph.D. (Jul. 3, 2002).
Chiron's Motion for Clarification regarding Memorandum and Order re: Priority, Anticipation, Written Description, Enablement, Best Mode, Utility, or, in the alternative, Motion for Reconsideration (Jul. 3, 2002).
Genentech's Inc.'s Proposed Jury Instructions (Phase I) (Jul. 26, 2002).
Genentech Inc.'s Responsive Trial Brief (Jul. 26, 2002).
Reporter's Daily Transcript Jury Trial (Aug. 6, 2002).
Reporter's Daily Transcript Jury Trial (Aug. 8, 2002).
Reporter's Daily Transcript Jury Trial (Aug. 9, 2002).
Genentech' Inc.'s Memorandum of Points and Authorities in Support of Objections to Chiron's Proposed Limiting Instruction (Aug. 9, 2002).
Genentech Inc.'s Request for a Remedial Jury Instruction, with Exhibits A–C (Aug. 12, 2002).
Reporter's Daily Transcript Jury Trial (Aug. 12, 2002).
Reporter's Daily Transcript Jury Trial (Aug. 13, 2002).
Reporter's Daily Transcript Jury Trial (Aug. 14, 2002).
Reporter's Daily Transcript Jury Trial (Aug. 16, 2002).
Genentech's Objections to Chiron's Proposed Jury Instructions (Phase I) (Aug. 16, 2002).
Genentech's Opposition to Chiron's Motion for Judgment as a Matter of Law Under Fed. R. Civ. P.50(A), with attached testimony cited to therein (Aug. 16, 2002).
Reporter's Daily Transcript Jury Trial (Aug. 20, 2002).
Reporter's Daily Transcript Jury Trial (Aug. 21, 2002).
Reporter's Daily Transcript Jury Trial (Aug. 22, 2002).
Reporter's Daily Transcript, Jury Trial (Sep. 3, 2002).
Memorandum of Points and Authorities Supporting Genentech's Motion for Judgment as a Matter of Law Under Fed. R. Civ. P.50(A) (Sep. 3, 2002).
Reporter's Daily Transcript, Jury Trial (Sep. 4, 2002).
Memorandum and Order Re: Rule 50 Motions (Sep. 11, 2002).
Genentech's Opposition to Chiron's Rule 50/59 Motion, with Attached Appendix of transcript and trial transcript pages cited to therein (Oct. 7, 2002).
Memorandum and Order Re: Renewed Motion for JM0L; Motion for New Trial (Oct. 22, 2002).
Brief of Defendant–Cross–Appellant, Genentech, Inc. (May 12, 2003).

*Chiron Corp. v. Genentech, Inc.*, 363 F.3d 1247 (Fed. Cir. 2004).

Expert Report of Dr. Rodney Kellems filed Aug. 27, 2004 in *In re Columbia University Patent Litigation*, MDL No. 1592.

Rebuttal Expert Report of Dr. Rodney Kellems filed Sep. 17, 2004 in *In re Columbia University Patent Litigation*, MDL No. 1592.

Deposition of Robert E. Kellems, Oct. 2, 2004, taken in *In re Columbia University Patent Litigation*, MDL No. 1592.

Plaintiffs' Joint Contentions On Invalidity to Non–Statutory Double Patenting, served Jul. 23, 2004 in *In re Columbia University Patent Litigation*, MDL No. 1592.

Exhibit 1 to Plaintiffs' Joint Contentions On Invalidity to Non–Statutory Double Patenting, served Jul. 23, 2004 in *In re Columbia University Patent Litigation*, MDL No. 1592.

Exhibit 2 to Plaintiffs' Joint Contentions On Invalidity to Non–Statutory Double Patenting, served Jul. 23, 2004 in *In re Columbia University Patent Litigation*, MDL No. 1592.

Decision on Motions (paper # 258 ), Nov. 30, 2004 (Int. No. 105, 048).

Decision on Priority (paper #39), Sep. 30, 2005 (Int. No. 105, 266).

Decision on Priority (paper #32), Sep. 30, 2005 (Int. No. 105, 267).

Abreau S.L. et al. *Biochem. Biophys. Res. Comm.* 82(4): 1300–1305, Jun. 1978. Intracellular location of human fibroblast interferon messenger RNA.

Adams J.M. et al. *Biochem.* 55: 147–155, 1966. N–formyl-methionyl–tRNA as the initiator of protein synthesis.

Alberts B. et al. Molecular Biology of the Cell. 107–108, 921, 1983.

Alt F. et al. *Cell* 27: 381–390, Dec. 1981. Organization and reorganization of immunoglobulin genes in A–MuLv–transformed cells: rearrangement of heavy but not light chain genes.

Applebaum S.W. et al. *Biochem. J.* 193: 209–216, 1981. The preparation and characterization of locust vitellogenin messenger RNA and the synthesis of its complementary DNA.

Atherton K.T. et al. *J. Gen. Virol.* 29: 297–304, 1975. Interferon induction by viruses and polynucleotides: a differential effect of camptothecin.

Aviv H. et al. *Proc. Natl. Acad. Sci. USA* 68(9): 2303–2307, Sep. 1971. Protein synthesis directed by encephalomyocarditis virus RNA: properties of a transfer RNA–dependent system.

Aviv H. et al. *Proc. Nat. Acad. Sci. USA* 69(6): 1408–1412, Jun. 1972. Purification of biologically active globin messenger RNA by chromatography on oligothymidylic acid–cellulose.

Ballantine J.E.M. et al. *J. Embryol. Exp. Morph.* 51: 137–153, 1979. Changes in protein synthesis during the development of *Xenopus laevis*.

Banerji J. et al. *Cell* 33: 729–740, 1983. A lymphocyte–specific cellular enhancer is located downstream of the joining region in immunoglobulin heavy chain genes.

Bantle J.A. et al. *Analytical Biochem.* 72: 413–427, 1976. Specificity of oligo (dT)–cellulose chromatography in the isolation of polyadenylated RNA.

Beato M. et al. *FEBS Lett.* 59(2): 305–309, Nov. 1975. Translation of the messenger RNA for rabbit uterglobulin in *Xenopus* oocytes.

Bergman W. et al. *J. Biol. Chem.* 254(13): 5690–5694, 1979. Formation of intermolecular disulfide bonds on nascent immunoglobulin polypeptides.

Berridge M.V. et al. *Cell* 8: 283–297, Jun. 1976. Translation of *Xenopus* liver messenger RNA in *Xenopus* oocytes: vitellogenin synthesis and conversion to platelet proteins.

Bevan M.J. *Biochem. J.* 122: 5–11, 1971. The vectoral release of nascent immunoglobulin peptides.

Blobel G. *FEBS Gene Expression*, 1977. Mechanisms for the intracellular compartmentaion of newly synthesized proteins.

Blobel G. et al. *J. Cell Biol.* 67: 835–851, 1975. Transfer of proteins across membranes.

Bole D.G. et al. *J. Cell. Biol.* 102: 1558–1566, 1986. Post-translational association of Immunoglobulin heavy chain binding protein with nascent heavy chains in nonsecreting and secreting hybridomas.

Boss M. et al. *Nucl. Acids. Res.* 12(9): 3791–3806, 1984. Assembly of functional antibodies from immunoglobulin heavy and light chains synthesized in *E. coli*.

Brack C. et al. *Cell* 15: 1–14, Sep. 1978. A complete immunoglobulin gene is created by somatic recombination.

Brinster R.L. et al. *Nature* 306: 332–336, 1983. Expression of a microinjected immunoglobulin gene in the spleen of transgenic mice.

Britten R.J. *Science* 142: 963–965, Nov. 1963. Complementary strand association between nucleic acids and nucleic acid gels.

Browne C.L. *Science* 203: 182–183, Jan. 1979. Ooctye–follicle cell gap junctions in *Xenopus laevis* and the effects of gonadotropin on their permeability.

Burke D. et al. *Nature* 271: 10–11, Jan. 1978. Translation of interferon messenger RNA in vivo and in vitro.

Calos M.P. et al. *Proc. Natl. Acad. Sci. USA* 80: 3015–3019, 1983. High mutation frequency in DNA transfected into mammalian cells.

Campbell P.N. et al. *FEBS Lett.* 72(2): 215–226, Dec. 1976. The role of organelles in the chemical modification of the primary translation products of secretory proteins.

Cattaneo A. et al. *EMBO J.* 6(9): 2753–2758, 1987. Polymeric immunoglobulin M is secreted by transfectants of non–lymphoid cells in the absence of immunoglobulin J chain.

Cavalieri R.L. et al. *Proc. Natl. Acad. Sci. USA* 74(10): 4415–4419. Oct. 1977. Induction and decay of human fibroblast interferon mRNA.

Chan L. et al. *J. Clin. Invest.* 57: 576–585, Mar. 1976. Translation of ovalbumin mRNA in *Xenopus laevis* oocytes.

Chen T.T. et al. *J. Biol. Chem.* 253(15): 5325–5331, 1978. Vittellin and vitellogenin from locusts (*Locusta migratoria*).

Coffino P. et al. *Proc. Natl. Acad. Sci. USA* 68(1): 219–223, Jan. 1971. Rate of somatic mutation in immunoglobulin production by mouse myeloma cells.

Cohn M. *Nucleic Acids in Immunology*, 671–715, 1968. The molecular biology of expectation.

Colman A. *Transcript. Translat.* 2: 49–69, 1984. Expression of exogeneous DNA in *Xenopus* oocytes.

Colman A. Transcription and Translation, a practical approach, edited by B.D. James and S. J. Higgins, 271–302, 1984. Translation of eukaryotic messenger RNA in *Xenopus* oocytes.

Colman A. et al. *Ciba Found. Symp.* 98: 249–67, 1983. The oocyte as a secretory cell.

Colman A. et al. *Cell* 17: 517–526, 1979. Export of proteins from oocytes of *Xenopus laevis*.

Colman A. et al. *Eur. J. Biochem.* 113:339–348, 1981. The influence of topology and glycosylation on the fate of heterologous secretory proteins made in *Xenopus* oocytes.

Colman A. et al. *J. Cell Biol.* 91: 770–780, Dec. 1981. Fate of secretory proteins trapped in oocytes of *Xenopus laevis* by disruption of the cytoskeleton or by imbalanced subunit synthesis.

Colman A. et al. *J. Mol. Biol.* 160: 459–474, 1982. Interaction of Mouse immunoglobulin chains within *Xenopus* oocytes.

Craig R.K. et al. *Biochem. J.* 160: 57–74, 1976. Guinea–pig milk–protein synthesis.

Craig R.K. et al. *Biochem. J.* 173: 633–641, 1978. Separation and partial characterization of guinea–pig caseins.

Darnell J.E. et al. *Proc. Natl. Acad. Sci. USA* 68(6): 1321–1325, Jun. 1971. An adenylic acid–rich sequence in messenger RNA of HeLa cells and its possible relationship to reiterated sites in DNA.

Darnell J.E. et al. *Science* 174: 507–510, Oct. 1971. Polyadenylic acid sequences: role in conversion of nuclear RNA into messenger RNA.

De Robertis E.M. et al. *Sci. Amer.* 75–82, Oct. 1979. Gene transplantation and the analysis of development.

Deacon N.J. et al. *FEBS Lett.* 79(1): 191–194, Jul. 1977. Fucose incorporation into oocyte–synthesized rat immunoglobulins.

Deacon N.J. et al. *Immunol.* 38(1): 137–144, Sep. 1979. Post–translational modification of rat immunoglobulins synthesized in the *Xenopus* oocyte translation system.

Deshpande A. K. et al. *J. Biol. Chem.* 254(18): 8937–8942, Sep. 1979. Translation and stability of rat liver messenger RNA for $\alpha_{2a}$–globulin in *Xenopus* oocyte.

Dicou E. et al. FEBS Lett. 104(2): 275–278, Aug. 1979. Synthesis of *Dyctyosleium discoideum* secretory proteins in *Xenopus laevis* oocytes.

Doel M.T. *Cell* 8: 51–58, May 1976. The translational capacity of deadenylated ovalbumin messenger RNA.

Dryer W.J. et al. *Proc. Natl. Acad. Sci. USA* 54: 864–869, 1965. The molecular basis for antibody formation: a paradox.

Dulis B. *J. Biol. Chem.* 258(4): 2181–2187, 1983. Regulation of protein expression in differentiation by subunit assembly.

Dumont J.N. et al. *J. Morph.* 155(1): 73–98, 1978. Oogenesis in *Xenopus laevis* (Daudin).

Edmonds M. et al. *Proc. Natl. Acad. Sci USA* 68(6): 1336–1340, Jun. 1971. Polyadenylic acid sequences in the heterogeneous nuclear RNA and rapidly–labeled polyribosomal RNA of HeLa Cells: possible evidence for a precursor relationship.

Eppig J.J. et al. *Dev. Biol.* 28: 531–536, 1972. Amino acid pools in developing oocytes of *Xenopus laevis*.

European Patent Office, Case No. T 0400/97 (Celltech Therapeutics Ltd.), Decision of the Technical Board of Appeal, May 24, 2000.

Falcoff E. et al. *Virol.* 75: 384–393, 1976. Intracellular location of newly synthesized interferon in human FS–4 cells.

Falkner G.F. et al. *Nature* 298(5871): 286–288, 1982. Expression of mouse immunoglobulin genes in monkey cells.

Feit H. et al. *J. Neurochem.* 28(4): 697–706, 1977. Comparison of the isoelectric and molecular weight properties of tubulin subunits.

Ford C.C. et al. *J. Embryol. Exp. Morph.* 37: 203–209, 1977. A method for enucleating oocytes of *Xenopus laevis*.

Fraser T. H. et al. *Proc. Natl. Acad. Sci. USA* 75(12): 5936–5940, Dec. 1978. Chicken ovalbumin is synthesized and secreted by ovalbumin is synthesized and secreted by *Escherichia coli*.

Futuichi Y. et al. *Nature* 266: 235–239, Mar. 1977. 5'–terminal structure and mRNA stability.

Gally J.A. et al. *Nature* 227: 341–348, Jul. 1970. Somatic translocation of antibody genes.

Gillies S.D. et al. *Cell* 33: 717–728, Jul. 1983. A tissue–specific transcription enhancer element is locate in the major intron of a rearranged immunoglobulin heavy chain gene.

Gillies S.D. et al. *Nucl. Acids Res.* 11(22): 7981–7997, 1983. Expression of cloned immunoglobulin genes introduced into mouse L cells.

Goldman B.M. *Proc. Nat. Acad. Sci. USA* 75(10): 5066–5070, Oct. 1978. Biogenesis of peroxisomes: intracellular site of synthesis f catalase and uricase.

Goodridge A. et al. *Eur. J. Biochem.* 98(1): 1–8, 1979. Synthesis of albumin and malic enzyme in wheat–germ lysates and *Xenopus laevis* oocytes programmed with chicken–liver messenger RNA.

Grässman A. et al. *Hoppe–Seyler's Z. Physiol. Chem.* 352: 527–532, Apr. 1971. Über die bildung von melanin in muskelzellen nach der direkten übertragung von RNA aus Harding–Passey–melamnomzellen.

Gray W.R. et al. *Science* 465–467, Jan. 1967. Mechanism of antibody synthesis: size differences between mouse kappa chains.

Gurdon J.B. *J. Embryol. exp. Morph.* 20(3): 401–414, Nov. 1968. Changes in somatic cell nuclei inserted into growing and maturing amphibian oocytes.

Gurdon J.B. et al. *Ann. Rev. Genet.* 15: 189–218, 1981. Gene transfer in amphibian eggs and oocytes.

Gurdon J.B. et al. *J. Mol. Biol.* 80: 539–551, 1973. Message stability in injected frog oocytes: long life of mammalian $\alpha$ and $\beta$ globin messages.

Gurdon J.B. et al. *Nature* 233: 177–182, Sep. 1971. Use of frog eggs and oocytes for the study of messenger RNA and its translation in living cells.

Gurdon J.B. et al. *Transcript Translat.*, xvii–xviii, 1984. A practical approach.

Haas I.G. et al. *Nature* 306(24): 387–389, 1983. Immunoglobulin heavy chain binding protein.

Hanks J.H. et al. *Proc. Soc. Exp. Biol. Med.* 71: 196–200, 1949. Relation of oxygen and temperature in the preservation of tissues by refrigeration.

Harry P. et al. *Comp. Biochem. Physiol.* 63B(2): 287–293, 1979. Changes in the pattern of secretion of locust female diglyceride–carrying lipoprotein and vitellogenin by the fat body in vitro during oocyte development.

Hendershot L. et al. *J. Cell. Biochem.* 104: 761–767, 1987. Assembly and secretion of heavy chains that do not associate posttranslationally with immunoglobulin heavy chain–binding protein.

Hendershot L. et al. *Mol. Cell. Biol.* 8(10): 4250–4256, 1988. Identity of the immunoglobulin heavy–chain protein with the 78,000–dalton glucose–regulated protein and the role of posttranslational modifications in its binding function.

Hew C.L. et al. *Biochem. Biophys. Res. Comm.* 71(3), 845–850, 1976. The synthesis of freezing–point–depressing protein of the winter founder *Pseudopleuronectus americanus* in *Xenopus laevis* oocytes.

Higgins S.J. et al. *Biochem. J.* 158: 271–282, 1976. Androgen–dependent synthesis of basic secretory proteins by the rat seminal vesicle.

Higgins S.J. et al. *Biochem. J.* 174: 543–551, 1978. Effects of testosterone on messenger ribonucleic acid and protein synthesis in rat seminal vesicle.

Hood L. et al. *Science* 168: 325–3431979. Mechanism of antibody diversity: germ line basis for variability.

Hood L.E. *Fed. Proc.* 31(1): 177–187, 1972. Two genes, one polypeptide chain—fact or fiction?

Housman D. et al. *Nature* 227: 913–918, 1970. Initiation of Haemoglobin synthesis by methionyl–tRNA.

Huez G. et al. *Nature* 271: 572–573, Feb. 1978. Functional stabilisation of HeLa cell histone messenger RNAs injected into *Xenopus* oocytes by 3'–OH polyadenylation.

Huez G. et al. *Proc. Natl. Acad. Sci. USA* 71(8): 3143–3246, Aug. 1974. Role of the polyadneylate segment in the translation of globin messenger RNA in *Xenopus* oocytes.

Jackson R. C. et al. *Proc. Natl. Acad. Sci.* 74(12): 5598–5602, Dec. 1977. Post–translational cleavage of presecretory proteins with an extract of rough microsomes from dog pancreas containing signal peptidase activity.

Jackson R. et al. *Nature* 227: 672–676, Aug. 1970. Role of methionine in the initiation of haemoglobin synthesis.

Jilka R. L. et al. *Arch. Biochem. Biophys.* 192(1): 290–295, 1979. Synthesis and processing of the mouse MOPC–321 κ Chain in *Xenopus laevis* oocytes.

Jilka R.L. et al. *Biochem. Biophys. Res. Comm.* 79(3): 627–630, 1977. Synthesis and glycosylation of the MOPC–46V immunoglobulin in kappa chain in *Xenopus laevis* oocytes.

Kacian D.L. et al. *Nature* 23(58)5: 167–169, 1972. In vitro synthesis of DNA components of human genes for globins.

Katz F.N. et al. *Proc. Natl. Acad. Sci. USA* 74(8): 3278–3282, Aug. 1977. Membrane in vitro synthesis, glycosylation, and asymmetric insertion of a transmembrane protein.

Kindas–Mügge I. et al. *J. Mol. Biol.* 87: 451–462, 1974. Insect protein synthesis in frog cells: the translation of honey bee promelittin messenger RNA in *Xenopus* oocytes.

Kitajewski J. et al. *Mol. Cell. Biol.* 12(2): 784–790, 1992. Interaction of Wnt–1 proteins with the binding protein BiP.

Koch G. *J. Biol. Chem.* 251(19): 6097–6107, 1976. Synthesis of the mitochondrial inner membrane in cultured *Xenopus laevis* oocytes.

Köhler G. *Proc. Natl. Acad. Sci. USA* 77(4): 2197–99, 1980. Immunoglobulin chain loss in hybridoma lines.

Kortbeek–Jacobs N. et al. *J. Immunol. Meth.* 24(1/2):195–199, 1978. Detection of specific antibody producing cells in porcine colostrum by in ovo translation of their mRNA.

Kourides I.A. et al. *Proc. Natl. Acad. Sci. USA* 76(1): 298–302, Jan. 1979. mRNA–directed biosynthesis of α subunit of thyrotopin: translation in cell–free and whole–cell systems.

Kreil G. *Ann. Rev. Biochem.* 50:317–348, 1981. Transfer of proteins across membranes.

Kvist S. et al. *Cell* 29: 61–69, May 1982. Membrane insertion and oligomeric assembly of HLA–DR histocompatibility antigens.

Labarca C. et al. *Proc. Natl. Acad. Sci. USA* 74(10): 4462–4465, Oct. 1977. mRNA–directed synthesis of catalytically active mouse β–glucuronidase in *Xenopus* oocytes.

Labrie F. *Nature* 221: 1217–1222, Mar. 1969. Isolation of an RNA with the properties of haemoglobin messenger.

Laemmli U.K. *Nature* 227, 680–685, Aug. 1970. Cleavage of structural proteins during the assembly of the head of bacteriophage T4.

Lanclos K.D. *Cell Diff.* 7: 259–270, 1978. Effects of estradiol on early messenger RNA in male *Xenopus laevis* liver.

Lane C. et al. *Eur. J. Biochem.* 101(2): 485–495, 1979. Sequestration and turnover of guinea–pig milk proteins and chicken ovalbumin in *Xenopus* oocytes.

Lane C. et al. *J. Mol. Biol.* 61: 73–91, 1971. Rabbit haemoglobin synthesis in frog cells: the translation of reticulocyte 9 s RNA in frog oocytes.

Lane C.D. *Curr. Top. Dev. Biol.* 18: 89–116, 1983. The fate of genes, messengers, and proteins introduced into *Xenopus* oocytes.

Lane, C.D. et al. *Biochem. Animal Dev.* 145–181, 1975. The injection of RNA into living cells: the use of frog oocytes for the assay of mRNA and the study of the control of gene expression.

Lane C.D. et al. *Eur. J. Biochem.* 111:225–235, 1980. The *Xenopus* oocyte as a surrogate secretory system.

Larkins B.A. et al. *Proc. Natl. Acad. Sci. USA* 76(12): 6448–6452, Dec. 1979. Synthesis and processing of maize storage proteins in *Xenopus laevis* oocytes.

Laskov R. et al. *J. Exp. Med.* 515–541, 1970. Synthesis, assembly, and secretion of gamma globulin by mouse myeloma cells.

Lebreleu B. et al. *Biochem. Biophys. Res. Comm.* 82(2): 665–673, 1978. Translation of mouse interferon mRNA *Xenopus laevis* oocytes.

Lederberg J. *Science* 1649–1653, Jun. 1959. Genes and antibodies.

Lee S.Y. et al. *Proc. Natl. Acad. Sci. USA* 68(6): 1331–1335, Jun. 1971. A polynucleotide segment rich in adenylic acid in the rapidly–labeled polyribosomal RNA component of mouse sarcoma 180 ascites cells.

Lennox E.S. et al. *Cold Spring Harbor Symposia on Quantitative Biology* 32: 249–254, 1967. A search for biosynthetic subunits of light and heavy chains of immunoglobulins.

Lim L. et al. *Biochim. Biophys. Acta* 361: 241–247, 1974. Isolation of microsomal poly(a)–RNA from rat brain directing the synthesis of the myelin encephalitogenic protein in *Xenopus* oocytes.

Lim L. et al. *Nature* 227: 710–712, 1970. Adenine–rice polymer associated with rabbit reticulocyte messenger RNA.

Lingappa V.R. et al. *J. Cell Biol.* 79: 567–572, Nov. 1978. Nascent chicken ovalbumin contains the functional equivalent of a signal sequence.

Lingappa V.R. et al. *Nature* 281: 117–121, Sep. 1979. Chicken ovalbumin contains an internal signal sequence.

Lingappa V.R. et al. *Proc. Natl. Acad. Sci. USA* 74(7): 2432–2436, Jun. 1977. Nascent prehormones are intermediates in the biosynthesis of authentic bovine pituitary growth hormone and prolactin.

Lisowska–Bernstein B. et al. *Proc. Natl. Acad. Sci. USA* 66(2): 425–532, Jun. 1970. Synthesis of immunoglobulin heavy and light chains by the free ribosomes of a mouse plasma cell tumor.

Liu C.P. et al. *Proc. Natl. Acad. Sci. USA* 76(9): 4503–4506, Sep. 1979. Biological detection of specific mRNA molecules by microinjection.

Lockard R.E. et al. *Nucl. Acids Res.* 5(9): 3237–3247, Sep. 1978. Requirement for 7–methylguanosine in translation of globin mRNA in vivo.

Mach B. et al. *Mol. Biol. Rep.* 1: 3–6, 1973. Different size of the product of the 14s light chain mRNA translated in vitro and in amphibian oocytes.

Mains P.E. et al. *J. Biol. Chem.* 258(8): 5027–5033, 1983. The requirement of light chain for the surface deposition of the heavy chain of immunoglobulin M.

Maizel J.V. *Methods in Virology*, 5: 179–246, 1971. Polyacrylamide gel electrophoresis of viral proteins.

Masui Y. *J. Exp. Zool.* 166(3): 365–376, 1967. Relative roles of the pituitary, follicle cells, and progesterone in the induction of oocyte maturation in *Ranna pipiens*.

Mechler B. et al. *J. Cell Biol.* 67: 1–15, 1975. Membrane–bound ribosomes of myeloma cells.

*MedImmune, Inc. v. Genentech, Inc.*, No. 05–608 (U.S.), Brief for Petitioner.

*MedImmune, Inc. v. Genentech, Inc.*, No. 05–608 (U.S.), Brief for Respondent City of Hope.

*MedImmune, Inc. v. Genentech, Inc.*, No. 05–608 (U.S.), Brief of Respondent Genentech, Inc.

*MedImmune, Inc. v. Genentech, Inc.*, No. 05–608 (U.S.), Reply Brief for Petitioner.

*MedImmune, Inc. v. Genentech, Inc.*, No. 05–608 (U.S.), transcript of oral argument.

Miflin B.J. et al. *Seed Prot. Improv.* 1: 137–159, 1979. The biology and biochemistry of cereal seed prolamins.

Mills F.C. et al. *Nature* 306: 809–812, Dec. 1983. DNase I hypersensitive sites in the chromatin of human µ immunoglobulin heavy–chain genes.

Moar V.A. et al. *J. Mol. Biol.* 61: 93–103, 1971. Translational capacity of living frog eggs and oocytes, as judged by messenger RNA injection.

Morrison S. *Ann. Rev. Immunol.* 2: 239–56, 1984. Transfer and expression of immunoglobulin genes.

Morrison S. et al. *Adv. Immunol.* 44: 65–92, 1989. Genetically engineered antibody molecules.

Morrison S. et al. *Proc. Natl. Acad. Sci. USA* 81: 6851–6855, 1984. Chimeric human antibody molecules: mouse antigen–binding domains with human constant region domains.

Morrison S.L. *Science* 229(4719): 1202–1207, 1985. Transfectomas provide novel chimeric antibodies.

Morser J. et al. *J. Gen. Virol.* 44(1): 231–234. Characterization of interferon messenger RNA from human lymphoblastoid cells.

Mous J. et al. *Biochem. Biophys. Res. Comm.* 79(4): 1111–1116, 1979. Synthesis of rat prostatic binding protein in *Xenopus* oocytes and in wheat germ.

Mous J. et al. *Eur. J. Biochem.* 94: 393–400, 1979. Translation of biologically active messenger RNA from human placenta in *Xenopus* oocytes.

Mous J.M. et al. *J. Biol. Chem.* 257(19): 11822–11828, Oct. 1982. Assembly, glycosylation, and secretion of the oligomeric rat prostatic binding protein in *Xenopus* oocytes.

Neuberger M. *EMBO J.* 2(8): 1373–1378, 1983. Expression and regulation of immunogloublin heavy chain gene transfected into lymphoid cells.

O'Farrell P. *J. Biol. Chem.* 250(10): 4007–4021, 1975. High resolution two–dimensional electrophoresis of proteins.

Ochi A. et al. *Proc. Natl. Acad. Sci. USA* 80: 6351–6355, 1983. Functional immunoglobulin M production after transfection of cloned immunoglobulin heavy and light chain genes into lymphoid cells.

Olsson L. *Proc. Natl. Acad. Sci. USA* 77(9): 5429–5431, 1980. Human–human hybridomas producing monoclonal antibodies of predefined antigenic specificity.

Olsson L. et al. *J. Immunol. Meth.* 61: 17–32, 1983. Antibody producing human–human hybridomas.

Palade G. *Science* 189: 347–358, 1975. Intracellular aspects of the process of protein synthesis.

Palmiter R. et al. *J. Biol. Chem.* 246(3): 724–737, 1971. Modulation of ovalbumin synthesis by estradiol–17β and actinomycin D as studied in explants of chick oviduct in culture.

Papkoff J. et al. *Mol. Cell. Biol.* 10(6): 2723–2730, 1990. Secreted int–1 Protein Is Associated with the Cell Surface.

Penman S. et al. *J. Mol. Biol.* 34: 49–69, 1968. Localization and kinetics of formation of nuclear heterodisperse RNA, cytoplasmic heterodisperse RNA and polyribosome–associated messenger RNA in HeLa cells.

Pilz I. et al. *Proc. Natl. Acad. Sci. USA* 77(1): 117–121, 1980. Effect of cleaving interchain disulfide bridges on the radius of gyration and maximum length of anti–poly(D–alanyl) antibodies before and after reaction with tetraalanine hapten.

Potter M. *Methods in Cancer Research* II: 105–157, 1967. The plasma cell tumors and myeloma proteins of mice.

Potter M. et al. *J. Gen. Virol.* 24(5): 1153–1163, 1960. Studies on eight transplantable plasma–cell neoplasms of mice.

Queen C. et al. *Cell* 33: 741–748, 1983. Immunoglobulin gene transcription is activated by downstream sequence elements.

Raftery M.A. et al. *Biochem. Biophys. Res. Comm.* 10(6): 467–72, 1963. Tryptic cleavage at cysteinyl peptide bonds.

Rapoport T.A. et al. *Eur. J. Biochem.* 87: 229–233, 1978. Synthesis of carp proinsulin in *Xenopus* oocytes.

Raschke W. C. et al. *Proc. Natl. Acad. Sci. USA* 76(7): 3469–3473, Jul. 1979. Assembly and secretion of pentameric IgM in a fusion between a nonsecreting B cell lymphoma and an IgG–secreting plasmacytoma.

Reynolds, Jr. F.H., et al. *Proc. Natl. Acad. Sci. USA* 72(12): 4881–4885, 1975. Interferon activity produced by translation of human interferon messenger RNA in cell–free ribosomal systems and in *Xenopus* oöcytes.

Robertson M. *Nature* 301(13): 114, 1983. Control of antibody production.

Rollins J.W. et al. *Science* 178: 1204–1205, 1972. Collagen synthesis in *Xenopus* oocytes after injection of nuclear RNA of frog embryos.

Ross J. et al. *Proc. Natl. Acad. Sci. USA* 69(1): 264–268, 1972. In vitro synthesis of DNA complementary to purified rabbit globin mRNA.

Roth R.A. et al. *Biochem.* 20: 6594–6599, 1981. Role of disulfide interchange enzyme in immunoglobulin synthesis.

Rothman J.F. et al. *Nature* 269: 775–780, 1977. Synchronised transmembrane insertion and glycosylation of a nascent membrane protein.

Rubinstein M. et al. *Science* 202: 1289–1290, 1978. Human leukocyte interferon purified to homogeneity.

Scherrer, K. *Proc. Nat. Acad. Sci. USA* 56: 1571–1578, 1966. Patterns of RNA metabolism in a differentiated cell: a rapidly labeled, unstable 60S RNA with messenger properties in duck erythroblasts.

Schubert D. et al. *J. Mol. Biol.* 53: 305–320, 1970. Immunoglobulin biosynthesis.

Sehgal P.B. et al *Proc. Natl. Acad. Sci. USA* 74(8): 3409–3413, 1977. Interferon messenger RNA content of human fibroblasts during induction, shutoff, and superinduction of interferon production.

Sehgal P.B. et al. *Proc. Natl. Acad. Sci. USA* 75(10): 5000–5033, 1978. Does 3'–terminal poly(A) stabilize human fibroblast interferon mRNA in oocytes of *Xenopus laevis*?

Seidman J.G. et al. *Nature* 276(21): 790–795, 1978. The arrangement and rearrangement of antibody genes.

Sherr C.J. et al. *Proc. Natl. Acad. Sci. USA* 66(4): 1183–1189, 1970. Immunoglobulin synthesis and secretion, V. Incorporation of leucine and glucosamine into immunoglobulin on free and bound polyribosomes.

Shores G.C. et al. *J. Cell Biol.* 72:726–743, 1977. Two fractions of rough endoplasmic reticulum from rat liver.

Siden E. et al. *Proc. Natl. Acad. Sci. USA* 78(3): 1823–1827, Mar. 1981. Synthesis of immunoglobulin μ chain gene products precedes synthesis of light chains during B–lymphocyte development.

Siden E.J. et al. *Cell* 16: 389–396, 1979. Immunoglobulin Synthesis by Lymphoid Cells transformed in vitro by abelson murine leukemia virus.

Smith A.E. et al. *J. Virol.* 28(1): 140–153, 1978. Extraction and fingerprint analysis of simian virus 40 large and small T–antigens.

Smith M. et al. *J. Mol. Biol.* 80: 553–557, 1973. Translation of Messenger RNA for mouse immunoglobulin light chains in living frog oocytes.

Smithies O. *Science* 157: 267–273, 1967. Antibody variability.

Snel P. et al. *Neth. J. Med.* 21: 138–143, 1978. Removal of bile acids by plasma exchange or plasma cell separation followed by perfusion through a charcoal adsorber.

Soeiro R. et al. *J. Cell Biol.* 39: 112–118, 1968. The turnover of nuclear DNA–like RNA in HeLa cells.

Soreq, H. *Critical Reviews in Biochemistry* 18(3): 199–238, 1985. The biosynthesis of Biologically Active Proteins in mRNA–Microinjected *Xenopus* Oocytes.

Stavnezer J. et al. *Nature New Biology* 230(14): 172–176, 1971. Synthesis of a mouse immunoglobulin light chain in a rabbit reticulocyte cell–free system.

Stevens R.H. et al. *J. Cell Biol.* 50: 818–829, 1971. RNA metabolism in HeLa cells at reduced temperature.

Stevens R.H. et al. *Nature* 239: 143–146, 1972. Specific IgG mRNA molecules from myeloma cells in heterogeneous nuclear and cytoplasmic RNA containing poly–A.

Stevens R.H. et al. *Proc. Natl. Acad. Sci. USA* 70(4): 1127–1131, 1973. Isolation of messenger RNA coding for mouse heavy–chain immunoglobulin.

Stevens R.H. et al. *Proc. Natl. Acad. Sci. USA* 72: 4679, 1975. Authors' statement on the isolation of mRNA coding for immunoglobulin heavy chain.

Strauss A.W. et al. *Critical Reviews in Biochemistry*, ed. Fasman G.D. 205–235, Mar. 1982. Compartmentaion of newly synthesized proteins.

Summers D.F. et al. *Proc. Natl. Acad. Sci. USA* 54: 505–513, 1965. Evidence for virus–specific noncapsid proteins in poliovirus–infected HeLa cells.

Swan D. et al. *Proc. Natl. Acad. Sci. USA* 69(7): 1967–1971, 1972. Purification and properties of biologically active messenger RNA for a myeloma light chain.

Szilard L. *Proc. Natl. Acad. Sci. USA* 46: 293–302, 1960. The molecular basis of antibody formation.

Valle G. et al. *Eur. J. Biochem.* 132: 131–138, 1983. Post–translational fate of variant MOPC 315 λ chains in *Xenopus* oocytes and mouse myeloma cells.

vanderDonk J.A. et al. *Nature* 271: 479–481, 1978. The use of *Xenopus* egg cells to assay the mRNA of single cells.

Vassalli P. et al. *J. Mol. Biol.* 56: 1–19, 1971. Cell–free synthesis of rat immunoglobulin.

Vassalli P. et al. *Proc. Natl. Acad. Sci. USA* 58: 2422–2429, 1967. Studies on cell–free synthesis of rat immunoglobulins, II. Synthesis of immunoglobulin and of antibody to the dinitrophenyl hapten.

Vassart G. et al. *Eur. J. Biochem.* 55: 15–22, 1975. Thyroglobulin messenger RNA: Translation of a 33–S mRNA into a peptide immunologically related to thyroglobulin.

Vassart G. et al. *Proc. Natl. Acad. Sci. USA* 72(10): 3839–3843, 1975. Translation of thyroglobulin 33S messenger RNA as a means of determining thyroglobulin quaternary structure.

Verma I.M. et al. *Nature New Biology* 235(58): 163–167, 1972. In vitro synthesis of DNA complementary to rabbit reticulocyte 10S RNA.

Vernon T.O. *Proc. Natl. Acad. Sci. USA* 80: 825–829, 1983. Immunoglobulin gene expression in transformed lymphoid cells.

Wabl M. et al. *Proc. Natl. Acad. Sci. USA* 79: 6976–6978, 1982. A theory of allelic and isotypic exclusion for immunoglobulin genes.

Wallace R.A. et al. *Developmental Biology* 19: 498–526, 1969. Studies on amphibian yolk.

Wallace R.A. et al. *J. Cell. Physiol.* 72(2): 73–89, 1968. The induced synthesis and transport of yolk proteins and their accumulation by the oocyte in *Xenopus laevis*.

Wallace R.A. et al. *J. Exp. Zool.* 175(3): 259–270, 1970. Protein incorporation by isolated amphibian oocytes.

Wheeler T. et al. *J. Virol.* 21(1): 215–224, 1977. Cell–free synthesis of polyoma virus capsid proteins VP1 and VP2.

White J.O. et al. *Biochem. Soc. Trans.* 3: 94–95, 1975. Properties of rat brain microsomal ribonucleic acid containing polyadenylate.

Wilde C.D. et al. *Eur. J. Immunol.* 10: 462–267, 1980. Analysis of immunoglobulin chain secretion using hybrid myelomas.

Williamson A.R. *Biochem. Soc. Trans.* 5: 139–175, 1969. The Biosynthesis of multichain proteins.

Williamson R. et al. *Ser. Haemat.* IV(3): 23–36, 1971. The isolation and DNA/RNA hybridization of messenger RNA for globin.

Winberry L. et al. *J. Immunol.* 124(3): 1174–1182, 1980. Immunoglobulin production and secretion by variant clones of the MOPC 315 mouse myeloma cell line.

Woodland H.R. et al. *Developmental Biology* 39(1): 134–140, 1974. The translation of mammalian globin mRNA injected into fertilised eggs of *Xenopus laevis*.

Yip C.C. et al. *Proc. Natl. Acad. Sci. USA* 72(12): 4777–4779, 1975. Translation of messenger ribonucleic acid from isolated pancreatic islets and human insulinomas.

Zehavi–Willner T. et al. *Cell* 11: 683–693, 1977. Subcellular compartmentation of albumin and globin made in oocytes under the direction of injected messenger RNA.

Joziasse D.H. et al. *Subcellular Biochem.* 32, 25–48. The α1,3–galactosyltransferase gene.

*MedImmune, Inc.* v. *Genentech, Inc.*, 427 F.3d 958 (Fed. Cir. 2005).

Sambrook, J., et al. *Molecular Cloning: A Laboratory Manual*, 2d ed., New York: Cold Spring Harbor, 1989. Table of contents; sections 16.1–16.8.1 ("Expression of cloned genes in cultured mammalian cells"); sections 17.1–17.44 ("Expression of cloned genes in *Escherichia coli*").

Petition showing good cause to make an interference settlement available under 35 U.S.C. § 135(c) and 37 C.F.R. § 1.666(b), Interference No. 102,572, Aug. 13, 2002.

Order on petition for access pursuant to 35 U.S.C. § 135(c) and 37 C.F.R. § 1.666(b), Interference No. 107,572, Oct. 18, 2002.

LoBuglio, A.F., et al. Human immune response to chimeric B72.3 (γ4), Abst. No. 76. *Antibody Immunoconj. Radiopharm.*, 1983. Exhibit No. 1182, Interference No. 104,532.

Cabilly Opposition to Glaxo Wellcome Inc.'s Miscellaneous Motion 1, Interference No. 104,532, Oct. 5, 2000.

Plaintiff MedImmune Inc.'s Complaint and Demand for Jury Trial, *MedImmune, Inc.* v. *Genentech, Inc.* (Case No. CV–03–2567, C.D. Cal.) (Apr. 11, 2003).

Amended Memorandum of Decision Re: Defendant Celltech's Motion for Judgment on the Pleadings and Defendant Genentech's Motion for Summary Judgment (Case No. CV–03–2567, C.D. Cal.), pp. 1–26 (Jan. 12, 2004).

Celltech R&D Ltd.'s Amended Answer to First Amended Complaint (Case No. CV–03–2567, C.D. Cal.), pp. 1–40 (Sep. 22, 2003).

Celltech R&D Ltd.'s Answer (Case No. CV–03–2567, C.D. Cal.), pp. 1–26 (Jun. 4, 2003).

Celltech R&D Ltd.'s Answer to First Amended Complaint (Case No. CV–03–2567, C.D. Cal.), pp. 1–40 (Sep. 2, 2003).

Civil Minute Order—General (*MedImmune, Inc.* v. *Genentech, Inc., City of Hope, and Celltech R&D Ltd.*), pp. 1–4 (Aug. 4, 2003).

Declaration of Jeffrey R. Witham in Support of MedImmune, Inc.'s Opposition Brief in Support of Claim Construction (*MedImmune, Inc.* v. *Genentech, Inc., City of Hope, and Celltech R&D Ltd.*), pp. 1–3 with Exhibits A–M (Jan. 16, 2004).

Declaration of Susan L. Friedman in Support of Genentech, Inc.'s Request for Judicial Notice in Support of Reply Memorandum for Motion to Dismiss the Third and Eleventh Causes of Action (*MedImmune, Inc.* v. *Genentech, Inc., City of Hope, and Celltech R&D Ltd.*), p. 1 (Jul. 28, 2003).

Defendant City of Hope National Medical Center's Answer (*MedImmune, Inc.* v. *Genentech, Inc., City of Hope, and Celltech R&D Ltd.*), pp. 1–37 (Sep. 2, 2003).

Defendant City of Hope's Joinder in Defendant Genentech, Inc.'s Opening Brief Re: Claim Construction (*MedImmune, Inc.* v. *Genentech, Inc., City of Hope, and Celltech R&D Ltd.*), pp. 1–2 (Dec. 22, 2003).

Defendant Genentech, Inc.'s Answer and Affirmative Defenses (*MedImmune, Inc.* v. *Genentech, Inc., City of Hope, and Celltech R&D Ltd.*), pp. 1–32 (Sep. 2, 2003).

Defendant Genentech, Inc.'s Opening Brief Regarding Claim Construction (*MedImmune, Inc.* v. *Genentech, Inc., City of Hope, and Celltech R&D Ltd.*), pp. 1–39 (Dec. 22, 2003).

Defendant Genentech, Inc.'s Notice of Motion and Motion to Dismiss the Third and Eleventh Causes of Action; Memorandum of Points and Authorities in Support (*MedImmune, Inc.* v. *Genentech, Inc., City of Hope, and Celltech R&D Ltd.*), pp. 1–14 (Jun. 4, 2003).

Defendant Genentech, Inc.'s Reply Memorandum of Points and Authorities in Support of Motion to Dismiss the Third and Eleventh Causes of Action (*MedImmune, Inc.* v. *Genentech, Inc., City of Hope, and Celltech R&D Ltd.*), pp. i–v and 1–14 (Jul. 28, 2003).

Genentech, Inc.'s Request for Judicial Notice in Support of Reply Memorandum for Motion to Dismiss the Third and Eleventh Causes of Action (*MedImmune, Inc.* v. *Genentech, Inc., City of Hope, and Celltech R&D Ltd.*), pp. 1–22 (Jul. 28, 2003).

Initial Disclosures of Plaintiff MedImmune, Inc. (*MedImmune, Inc.* v. *Genentech, Inc., City of Hope, and Celltech R&D Ltd.*), pp. 1–10 (Aug. 21, 2003).

MedImmune, Inc.'s Opposition Brief Regarding Claim Construction (*MedImmune, Inc.* v. *Genentech, Inc., City of Hope, and Celltech R&D Ltd.*), pp. i–ii and 1–38 (Jan. 16, 2004).

MedImmune, Inc.'s Responses and Objections to Genentech, Inc.'s First Set of Interrogatories (*MedImmune, Inc.* v. *Genentech, Inc., City of Hope, and Celltech R&D Ltd.*), pp. 1–14 (Sep. 3, 2003).

MedImmune, Inc.'s Responses and Objections to Genentech, Inc.'s First Set of Requests for Admission (*MedImmune, Inc.* v. *Genentech, Inc., City of Hope, and Celltech R&D Ltd.*), pp. 1–18 (Sep. 3, 2003).

MedImmune, Inc.'s Responses and Objections to Genentech, Inc.'s First Set of Requests for the Production of Documents (*MedImmune, Inc.* v. *Genentech, Inc., City of Hope, and Celltech R&D Ltd.*), pp. 1–28 (Sep. 3, 2003).

Memorandum of Decision Re: Defendant Celltech's Motion for Judgment on the Pleadings and Defendant Genentech's Motion for Summary Judgment (*MedImmune, Inc.* v. *Genentech, Inc., City of Hope, and Celltech R&D Ltd.*), pp. 1–26 (Dec. 22, 2003).

Order Granting Genentech Inc.'s Motion to Dismiss the Third and Eleventh Causes of Action (*MedImmune, Inc.* v. *Genentech, Inc., City of Hope, and Celltech R&D Ltd.*), pp. 1–2 (Aug. 11, 2003).

Plaintiff MedImmune, Inc.'s Opposition to Motion by Defendant Genentech, Inc. to Dismiss the Third and Eleventh Causes of Action (*MedImmune, Inc.* v. *Genentech, Inc., City of Hope, and Celltech R&D Ltd.*), pp. 1–19 (Jul. 14, 2003).

*MedImmune, Inc.* v. *Genentech, Inc.*, No. 05–608 (U.S.), slip op. (Jan. 9, 2007).

Decision on Petition, Interference No. 102,572, filed Apr. 4, 2003 (Paper No. 85).

Decision on Petition, Interference No. 102,572, filed Apr. 4, 2003 (Paper No. 86).

Grounds of Opposition filed on Behalf of Genentech, Inc. in Respect of Their Opposition to EP–B–0120694 (84301996.9) in the Name of Celltech Limited and entitled 'Process for the Production of Multichain Polypeptides or Proteins,' filed Apr. 19, 1994.

Bolivar F. et al. *Gene* 2: 95–113, 1977. Construction and characterization of new cloning vehicles. II. A multipurpose cloning system.

Cohen S.N. et al. *Proc. Nat'l Acad. Sci. USA* 69(8): 2110–14, 1972. Nonchromosomal antibiotic resistance in bacteria: genetic transformation of *Escherichia coli* by R–factor DNA.

Grunstein M. et al. *Proc. Nat'l Acad. Sci. USA* 72(10): 3961–65, 1975. Colony hybridization: a method for the isolation of cloned DNAs that contain a specific gene.

Hanahan D. et al. *Cell* 21: 127–39, 1980. Characteristics of an SV40 plasmid recombinant and its movement into and out of the genome of a murine cell.

Hood L. et al. *Ann. Rev. Genet.* 9: 305–53, 1975. Organization, expression, and evolution of antibody genes and other multigene families.

Howard M.C. *CRC Crit. Rev. Immunol.* 3(3): 181–208, 1982. Antigen–induced B lymphocyte differentiation.

Mellon P. et al. *Cell* 27(2 pt 1): 279–88, 1981. Identification of DNA sequences required for transcription of the human α1–globin gene in a new SV40 host–vector system.

Miozzari G.F. et al. *J. Bacteriol.* 133(3): 1457–66, 1978. Translation of the leader region of the *Escherichia coli* tryptophan operon.

Polisky B. *Cell* 55(6): 929–32, 1988. ColE1 replication control circuitry: sense from antisense.

Ross J. *Microbiol. Rev.* 59(3): 423–50, 1995. mRNA stability in mammalian cells.

U.S. Appl. No. 06/358,414 (Moore et al.), application filed Mar. 15, 1982.

U.S. Appl. No. 08/165,530 (Winter et al.), prosecution history.

*MedImmune, Inc. v. Genentech, Inc.*, Order remanding to district court (Fed. Cir. Nos. 04–1330, –1364, Mar. 7, 2007).

*MedImmune, Inc. v. Genentech, Inc.*, Stipulation and order rescheduling status conference (C.D. Cal. No. CV 03–2567 MRP (CTx), Apr. 12, 2007).

Amzel et al., "The Three Dimensional Structure of a Combining Region–Ligand Complex of Immunoglobulin NEW at 3.5 Å Resolution," *Proc. Natl. Acad. Sci. USA* 71:1427–1430 (1974).

Basic & Clinical Immunology, pp. 28–29, 34–37, 83–95, 254–257, 266–267, 342–381, 742, 745–746 (H. Hugh Fudenberg ed., Lange Medical Publications 1980).

Burton, "Human Monoclonal Antibodies: Achievement and Potential," *Hospital Practice* 27(8): 67–74 (1992).

Edelman et al., "Reconstitution of Immunologic Activity by Interaction of Polypeptide Chains of Antibodies," *Proc. Natl. Acad. Sci. USA* 50:753–761 (1963).

Edelman et al., "The Covalent Structure of an Entire γG Immunoglobulin Molecule," *Biochem.* 63:78–85 (1969).

Edelman, "Antibody Structure and Molecular Immunology," *Nobel Lecture: Physiology or Medicine*, Dec. 2, 1972, pp. 31–54.

Maclyn McCarty, "Chemical Nature And Biological Specificity Of The Substance Inducing Transformation of Pneumococcal Types," *Microbiol. Mol. Biol. Rev.* 10(12): 63–71 (1946).

Milstein et al., "Interchain Disulphide Bridges of Mouse Immunoglobulin M," *Biochem. J.* 151:615–624 (1975).

"Monoclonal Antibodies," pp. 8–11, 75–99, 171–182, 275–289 (Roger H. Kennett et al. ed., Plenum Press 1980).

Poljak et al., "Structure of Fab' New at 6 Å resolution," *Nat New Biol.* 235:137–140 (1972).

Sarma et al., "The Three–Dimensional Structure at 6 Å Resolution of a Human γG1 Immunoglobulin Molecule," *J. Biological Chem.* 246:3753–3759 (1971).

Segal DM et al., "The Three–Dimensional Structure of Phosphorylcholine–Binding Mouse Immunoglobulin Fab and the nature of the antigen Binding Site," *Proc. Natl. Acad. Sci. USA* 71:4298–4302 (1974).

Silverton et al, "Three–dimensional structure of an intact human immunoglobulin," *Proc. Natl. Acad. Sci. USA* 74:5140–5144 (1977).

Thaler et al., Medical Immunology, pp. 3–8 (J.B. Lippincott Company 1977).

Wigler et al., "Biochemical Transfer of Single–Copy Eucaryotic Genes Using Total Cellular DNA as Donor," *Cell* 14: 725–731 (1978).

Weissman et al., Essential Concepts in Immunology, pp. 2, 12–19, 23–26, 49–54 (The Benjamin/Cummings Pub. Co. 1978).

Yarmush et al., "Identification and characterization of rabbit–mouse hybridomas secreting rabbit immunoglobulin chains," *Proc. Natl. Acad. Sci.* 77(5): 2899–2903 (1980).

File history of U.S. Appl. No. 07/233,430.

File History of U.S. Appl. No. 07/930,821.

File History of U.S. Appl. No. 08/165,530.

File History of U.S. Appl. No. 08/320,381.

File History of U.S. Appl. No. 08/450,727.

File History of U.S. Appl. No. 08/461,071.

Transcript of Proceedings before Honorable Mariana Pfaelzer, United States District Judge, Markman Hearing, Jul. 11, 2007, *MedImmune, Inc. v. Genentech, Inc.* (C.D. Cal. No. CV 03–2567 MRP (CTx)).

Claim Construction Order, Aug. 16, 2007, *MedImmune, Inc. v. Genentech, Inc.* (C.D. Cal. No. CV 03–2567 MRP (CTx)).

Deposition transcript of Shmuel Cabilly (Nov. 1, 2007), with exhibits.

Deposition transcript of Herbert Heyneker (Oct. 28, 1997), with exhibits.

Deposition transcript of William E. Holmes (Oct. 19, 2007), with exhibits.

Deposition transcript of Arthur D. Riggs, M.D. (Nov. 16, 2007).

Deposition transcript of Ronald Burnell Wetzel (Nov. 29, 2007), with exhibits.

Deposition transcript of Ian M. Armitage (Oct. 16, 2007), with exhibits.

Deposition transcript of Ginger Dreger (Oct. 17, 2007), with exhibits.

Deposition transcript of Max D. Hensley (Oct. 24, 2007), with exhibits.

Deposition transcript of Sean Johnston (Nov. 9, 2007), with exhibits.

Andersen D.C. et al. *Curr. Op. Biotechnol.* 15:456–62 (2004). Production technologies for monoclonal antibodies and their fragments.

Liu F.–T. et al. *Proc. Nat'l Acad. Sci. USA* 79: 7852–56 (1982). Cloning and nucleotide sequence of mouse immunoglobulin ε chain cDNA.

Wetzel R. *Am. Sci.* 68:664–75, 1980. Applications of recombinant DNA.

Wetzel R. et al. *Biochem.* 19: 6096–104 (1980). Production of biologically active $N^\alpha$–desacetylthymosin α1 in *Escherichia coli* through expression of a chemically synthesized gene.

Exhibit 136 to deposition of Herbert Heyneker (Oct. 28, 1997).

Exhibits to deposition of Arthur D. Riggs, M.D. (Nov. 16, 2007).

Alexander A. et al. *Proc. Natl. Acad. Sci. USA* 79: 3260–64, 1982. Gamma heavy chain disease in man: cDNA sequence supports partial gene deletion model.

Auffray C. et al. *Gene* 12: 77–86, 1980. Nucleotide sequence of a cloned cDNA corresponding to secreted mu chain of a mouse immunoglobulin.

Dunnick W. et al. *Nucl. Acids. Res.* 8: 1475–84, 1980. A mouse immunoglobulin heavy chain deletion mutant: isolation of a cDNA clone and sequence analysis of the mRNA.

Hellman L. et al. *Proc. Natl. Acad. Sci. USA* 79(4): 1264–68, 1982. Characterization and molecular cloning of the mRNA for the heavy (epsilon) chain of rat immunoglobulin E.

Hiatt A. et al., *Nature* 342: 76–78, (1989). Production of antibodies in transgenic plants.

Kenten J. et al. *Proc. Natl. Acad. Sci. USA* 79: 6661–65, 1982. Cloning and sequence determination of the gene for the human immunoglobulin epsilon chain expressed in a myeloma cell line.

Martens C.L. et al. *Proc. Natl. Acad. Sci. USA* 79: 6018–22, 1982. Heavy chain genes of rabbit IgG: isolation of a cDNA encoding gamma heavy chain and identification of two genomic C gamma genes.

Mushinski J.F. et al. *Proc. Natl. Acad. Sci. USA* 77: 7405–09, 1980. Mouse immunoglobulin D: construction and characterization of a cloned delta chain cDNA.

Obata M. et al. *Gene* 9: 87–97, 1980. Immunoglobulin gamma 1 heavy chain gene: structural gene sequences cloned in a bacterial plasmid.

Rogers J. et al. *Cell* 20: 302–12, 1980. Two mRNAs with different 3' ends encode membrane–bound and secreted forms of immunoglobulin mu chain.

Schlom J. et al. *Proc. Natl. Acad. Sci. USA* 77: 6841–45, Nov. 1980. Generation of human monoclonal antibodies reactive with human mammary carcinoma cells.

Schrier P.H. et al. *Proc. Natl. Acad. Sci. USA* 78: 4495–99, 1981. Multiple differences between the nucleic acid sequences of the IgG2aa and IgG2ab alleles of the mouse.

Simmons L.C. et al. *J. Immunol. Meth.* 263: 133–147, 2002. Expression of full–length immunoglobulins in *Escherichia coli*: rapid and efficient production of aglycosylated antibodies.

Sire J. et al. *Gene* 20: 377–86, 1982. Rat immunoglobulin delta heavy chain gene: nucleotides sequence derived from cloned cDNA.

Tyler B.M. et al. *Proc. Natl. Acad. Sci. USA* 79: 2008–12, 1982. mRNA for surface immunoglobulin gamma chains encodes a highly conserved transmembrane sequence and a 28–residue intracellular domain.

Associated Press, Jul. 11, 1982. RI scientists find way to mass–produce cancer fighters.

Baker M.D. et al. *Gene* 69: 349–55, 1988. Expression of an immunoglobulin kappa light–chain gene in lymphoid cells using a bovine papilloma–virus–1 (BPV–1) vector.

Banerji J. et al. *Cell* 27: 299–307, 1981. Expression of a β–globin gene is enhanced by remote SV40 DNA sequences.

Barrett T.J. et al. *J. Clin. Microbiol.* 17: 625–27, 1983. Enzyme–linked immunosorbent assay for detection of human antibodies to *Salmonella typhi* Vi antigen.

Bollen A. et al. *Biochem. Biophys. Res. Comm.* 103: 391–401, 1981. Expression in *Escherichia coli* of urokinase antigenic determinants.

Boven E. et al. *Radiother. Oncol.* 5: 109–17, 1986. Monoclonal antibodies in cancer treatment: where do we stand after 10 years?

Bowden D.W. et al. *Gene* 27: 87–99, 1984. Cloning of eukaryotic genes in single–strand phage vectors: the human interferon genes.

Braun J. et al. *Western J. Med.* 157:158–68, 1992. The second century of the antibody. Molecular perspectives in regulation, pathophysiology, and therapeutic applications.

Brekke O.H. et al. *Nat. Rev. Drug Discov.* 2: 52–62, 2003. Therapeutic antibodies for human diseases at the dawn of the twenty–first century.

Brousseau R. et al. *Gene* 17: 279–89, 1982. Synthesis of a human insulin gene. V. Enzymatic assembly, cloning and characterization of the human proinsulin DNA.

Chang A.C. et al. *Nature* 275: 617–24, 1978. Phenotypic expression in *E. coli* of a DNA sequence coding for mouse dihydrofolate reductase.

Cordingley M. et al. *J. Gen. Virol.* 54: 409–11, 1981. Transcription and translation of the herpes simplex virus type 1 thymidine kinase gene after microinjection into *Xenopus laevis* oocytes.

Cosimi A.B. et al. *N. Engl. J. Med.* 305: 308–14, 1981. Use of monoclonal antibodies to T–cell subsets for immunologic monitoring and treatment in recipients of renal allografts.

Crea R. et al. *Proc. Nat'l Acad. Sci. USA* 75:5765–69, 1978. Chemical synthesis of genes for human insulin.

Croce C.M. et al. *Eur. J. Immunol.* 10: 486–88, 1980. Preferential retention of human chromosome 14 in mouse×human B cell hybrids.

Croce C.M. et al. *Proc. Nat'l Acad. Sci. USA* 76: 3416–19, 1979. Chromosomal location of the genes for human immunoglobulin heavy chains.

Dalla–Favera R. et al. *Proc. Nat'l Acad. Sci. USA* 79: 7824–27, 1982. Human c–myc oncogenic is located on the region of chromosome 8 that is translocated in Burkitt lymphoma cells.

de Saint Vincent B.R. et al. *Cell* 27: 267–77, 1981. The cloning and reintroduction into animal cells of a functional CAD gene, a dominant amplifiable genetic marker.

Dillman R.O. *Crit. Rev. Oncol. Hematol.* 1: 357–86, 1984. Monoclonal antibodies in the treatment of cancer.

Ebersman D. Slides presented on Genentech, Inc. webcast Mar. 14, 2008. Investment community meeting: financial overview.

Echols H. et al. *Microbiol. Rev.* 42: 577–91, 1978. Genetic map of bacteriophage lambda.

Edge M.D. et al. *Nature* 292: 756–62, 1981. Total synthesis of a human leukocyte interferon gene.

Engvall E. et al. *Immunochem.* 8: 871–74, 1971. Enzyme–linked immunosorbent assay (ELISA). Quantitative assay of immunoglobulin G.

Erikson J. et al. *Nature* 294: 173–75, 1981. Assignment of the genes for human λ immunogloblin chains to chromosome 22.

Etkin L.D. et al. *Dev. Biol.* 75: 13–25, 1980. The synthesis of authentic sea urchin transcriptional and translational products by sea urchin histone genes injected into *Xenopus laevis* oocytes.

Fjermedal G. *Magic Bullets*. New York: MacMillan, 1984 (dust jacket and table of contents).

Folger K.R. et al. *Mol. Cell. Biol.* 2:1372–87, 1982. Patterns of integration of DNA microinjected into cultured mammalian cells; evidence for homologous recombination between injected plasmid DNA molecules.

Freedman M.H. et al. *J. Biol. Chem.* 241: 5225–32, 1966. Recovery of specific activity upon reoxidation of completely reduced polyalanyl rabbit antibody.

Gerhard W. et al. *Proc. Nat'l Acad. Sci. USA* 75: 1510–14, 1978. Repertoire of antiviral antibodies expressed by somatic cell hybrids.

Gheysen D. et al. *J. Mol. Appl. Genet.* 1: 385–94, 1982. Expression and excretion of human fibroblast β1 interferon in monkey cells after transfection with a recombinant SV40 plasmid vector.

Goeddel D.V. et al. *Proc. Nat'l Acad. Sci. USA* 76: 106–10, 1979. Expression in *Escherichia coli* of chemically synthesized genes for human insulin.

Goto Y. et al. *J. Mol. Biol.* 156: 891–910, 1982. Unfolding and refolding of the constant fragment of the immunoglobulin light chain.

Goto Y. et al. *J. Mol. Biol.* 156: 911–26, 1982. Unfolding and refolding of the reduced constant fragment of the immunoglobulin light chain. Kinetic role of the intrachain disulfide bond.

Graham F.L. et al. *Virology* 54: 536–39, 1973. Transformation of rat cells by DNA of human adenovirus 5.

Graves J.F. et al. *J. Bacteriol.* 152: 1071–77, 1982. Sequence–specific DNA uptake in transformation of *Neisseria gonorrhoeae*.

Grosschedl R. et al. *Cell* 38: 647–58, 1984. Introduction of a μ immunoglobulin gene into the mouse germ line: specific expression in lymphoid cells and synthesis of functional antibody.

Grosschedl R. et al. *Cell* 41: 885–97, 1985. Cell–type specificity of immunoglobulin gene expression is regulated by at least three DNA sequence elements.

Gunge N. *Ann. Rev. Microbiol.* 37: 253–76, 1983. Yeast DNA plasmids.

Haber E. *Biochem. Pharmacol.* 32: 1976–77, 1983. Antibodies as models for rational drug design.

Haber E. *Pharm. Rev.* 34: 77–84, 1982. Antibodies in vivo.

Haber E. *Proc. Nat'l Acad. Sci. USA* 52: 1099–1106, 1964. Recovery of antigenic specificity after denaturation and complete reduction of disulfides in a papain fragment of antibody.

Haber E., in *Monoclonal Antibodies in Clinical Medicine*, A.J. McMichael et al., eds., New York: Academic Press, 1982, pp. 478–500. Monoclonal antibodies to drugs: new diagnostic and therapeutic tools.

Hamer D.H. et al. *Cell* 17: 725–35, 1979. SV40 recombinants carrying rabbit β–globin gene coding sequences.

Hamer D.H. et al. *Nature* 281: 35–40, 1979. Expression of the chromosomal mouse $\beta^{maj}$–globin gene cloned in SV40.

Hardy K. et al. *Nature* 293: 481–83, 1981. Production in *B. subtilis* of hepatitis B core antigen and a major antigen of foot and mouth disease virus.

Hawley T. et al. *Immunol. Lett.* 12: 257–62, 1986. Immunoglobulin synthesis in non–B cell lines.

Hess B. et al. *Adv. Enzyme Regul.* 7: 149–67, 1969.

Hitzeman R.A. et al. *Nucleic Acids Res.* 11: 2745–63, 1983. Expression of hepatitis B virus surface antigen in yeast.

Hitzeman R.A. et al. *Nature* 293: 717–21, 1981. Expression of a human gene for interferon in yeast.

Hitzeman R.A. et al. *J. Biol. Chem.* 255: 12073–80, 1980. Isolation and characterization of the yeast 3–phosphoglycerokinase gene (PGK) by an immunological screening technique.

Hodgson J. *Biotechnology* 9: 421–25, 1991. Making monoclonals in microbes.

Holland M.J. et al. *Biochem.* 17: 4900–07, 1978. Isolation and identification of yeast messenger ribonucleic acids coding for enolase, glyceraldehyde–3–phosphate dehydrogenase, and phosphoglycerate kinase.

Hung P.P. *Adv. Exp. Med. Biol.* 172: 281–93, 1984. The cloning, isolation and characterization of a biologically active human enzyme, urokinase, in *E. coli*.

Itakura K. et al. *Science* 198: 1056–63, 1977. Expression in *Escherichia coli* of a chemically synthesized gene for the hormone somatostatin.

Jones E.W. *Genetics* 85: 23–33, 1977. Proteinase mutants of *Saccharomyces cerevisiae*.

Kasten F.H., in *Tissue culture: methods and applications*, P.F. Kruse et al., eds., New York: Academic Press, 1973, pp. 72–122. Mammalian myocardial cells.

Kearney J.F. et al. *J. Immunol.* 123: 1548–50, 1979. A new mouse myeloma cell line that has lost immunoglobulin expression but permits the construction of antibody–secreting hybrid cell lines.

Kenten J. et al. *Proc. Nat'l Acad. Sci. USA* 81: 2955–59, 1984. Properties of a human immunoglobulin ε–chain fragment synthesized in *Escherichia coli*.

Kingsman A.J. et al. *Gene* 7: 141–52, 1979. Replication in *Saccharomyces cerevisiae* of plasmid pBR313 carrying DNA from the yeast trpl region.

Kipps T.J. et al. 13th Ann. UCLA Symp., *J. Cell. Biochem.* Suppl 8A, 1984, abst. No. 0443. Allotype switch variants in cultured monoclonal producing hybridomas.

Koprowski H. et al. *Proc. Nat'l Acad. Sci. USA* 74: 2985–87, 1977. Production of antibodies against influenza virus by somatic cell hybrids between mouse myeloma and primed spleen cells.

Kurokawa T. et al. *Nucl. Acids Res.* 11: 3077–85, 1983. Expression of human immunoglobulin E ε chain cDNA in *E. coli*.

Laub O. et al. *J. Biol. Chem.* 258: 6037–42, 1983. Expression of the human insulin gene in an alternate mammalian cell and in cell extracts.

Laub O. et al. *J. Biol. Chem.* 258: 6043–50, 1983. Expression of the human insulin gene and cDNA in a heterologous mammalian system.

Lennox E.S., in *Hybridomas in cancer diagnosis and treatment* (*Prog. Cancer Res.* vol. 21), M.S. Mitchell et al., eds., New York: Raven Press, pp. 5–13, 1982. Monoclonal antibodies and tumor antigens—a perspective.

Marston F.A. *Biochem. J.* 240: 1–12, 1986. The purification of eukaryotic polypeptides synthesized in *Escherichia coli*.

McCormick F. et al. *Mol. Cell. Biol.* 4: 166–72, 1984. Inducible expression of amplified human β–interferon genes in CHO cells.

Mellor J. et al. *Gene* 24: 1–14, 1983. Efficient synthesis of enzymatically active calf chymosin in *Saccharomyces cerevisiae*.

Mertz J.E. et al. *Proc. Nat'l Acad. Sci. USA* 74: 1502–06, 1977. Purified DNAs are transcribed after microinjection into *Xenopus* oocytes.

Miller R.A. et al. *N. Engl. J. Med.* 306: 517–22, 1982. Treatment of B–cell lymphoma with monoclonal anti–idiotype antibody.

Miller R.A., in *Hybridomas in cancer diagnosis and treatment* (*Prog. Cancer Res.* vol. 21), M.S. Mitchell et al., eds., New York: Raven Press, pp. 133–145, 1982. Considerations for treatment with hybridoma antibodies.

Morrison S.L. et al. *Important Adv. Oncol.* 1990: 3–18, 1990. Recombinant chimeric monoclonal antibodies.

Morrison S.L. et al. *Mt. Sinai J. Med.* 53: 175–80, 1986. Production of novel immunoglobulin molecules by gene transfection.

Nakamura R.M. *Clin. Physiol. Biochem* 1: 160–72, 1983. Monoclonal antibodies: methods and clinical laboratory applications.

Newman R. et al. *Nature* 304: 643–45, 1983. Selection and properties of a mouse L–cell transformant expressing human transferrin receptor.

Ng A.K. et al. *Adv. Internal Med.* 28: 253–76, 1983. Monoclonal antibodies and immunologic approaches to malignant tumors.

Norman P.S. *Prog. Allergy* 32: 318–46, 1982. Immunotherapy.

Ohno S. et al. *Nucl/ Acids Res.* 10: 967–77, 1982. Inducer–responsive expression of the cloned human interferon β1 gene introduced into cultured mouse cells.

Oldham R.K. et al. *J. Biol. Response Mod.* 2; 1–37, 1983. Immunotherapy: the old and the new.

Olsson L. *Allergy* 38: 145–54, 1983. Monoclonal antibodies in clinical immunobiology. Derivation, potential, and limitations.

Olsson L. et al. *Meth. Enzymol.* 92: 3–16, 1983. Human–human monoclonal antibody–producing hybridomas: technical aspects.

Pääbo S. et al. *Cell* 33: 445–53, 1983. Association between transplantation antigens and a viral membrane protein synthesized from a mammalian expression vector.

Pavlakis G.N. et al. *Proc. Nat'l Acad. Sci. USA* 80: 397–401, 1983. Regulation of a metallothionein–growth hormone hybrid gene in bovine papilloma virus.

Pennica D. et al. *Nature* 301: 214–21, 1983. Cloning and expression of human tissue–type plasminogen activator cDNA in *E. coli*.

Petersen J.G. et al. *J. Biol. Chem.* 249: 5633–41, 1974. An in vitro system for studying the kinetics of interchain disulfide bond formation in immunoglobulin G.

Pharmalive. *Med Ad News* 11(7), Jul. 2005. Top 100 biotechnology companies.

Pharmalive. *Med Ad News* 13(9), Sep. 2007. Top 50 pharmaceutical companies charts and lists.

Piggee C. *Analyt. Chem.* 80: 2305–10 (2008). Therapeutic antibodies coming through the pipeline.

Poynton C.H. et al. *Exp. Biol.* 43: 13–33, 1984. Monoclonal antibodies: the possibilities for cancer therapy.

Prentice H.G. et al. *Lancet* 1(8274): 700–03, 1982. Use of anti–T–cell monoclonal antibody OKT3 to prevent acute graft–versus–host disease in allogeneic bone–marrow transplantation for acute leukaemia.

Ratzkin B. et al. *Proc. Nat'l Acad. Sci. USA* 78(6): 3313–17, 1981. Expression in *Escherichia coli* of biologically active enzyme by a DNA sequence coding for the human plasminogen activator urokinase.

Ringold G. et al. *J. Mol. Appl. Genet* 1: 165–75, 1981. Co–expression and amplification of dihydrofolate reductase cDNA and the *Escherichia coli* XGPRT gene in Chinese hamster ovary cells.

Russell P.S. *Transplant. Proc.* 14: 506–08, 1982. New approaches to the use of antibodies for immunosuppression.

Russell P.S. et al. *Ann. Rev. Med.* 35: 63–79, 1984. Monoclonal antibodies for the diagnosis and treatment of transplant rejection.

Satz M.L. et al. *Mol. Cell. Biol.* 3: 2006–16, 1983. Differential expression of porcine major histocompatibility DNA sequences introduced into mouse L cells.

Seto J. et al. *Cancer Res.* 42: 5209–15, 1982. Monoclonal anti–MM46 antibody: ricin A chain conjugate: in vitro and in vivo antitumor activity.

Shulman M. et al. *Nature* 276: 269–70, 1978. A better cell line for making hybridomas secreting specific antibodies.

Stepién P.P. et al. *Gene* 24: 289–97, 1983. Synthesis of a human insulin gene. VI. Expression of the synthetic proinsulin gene in yeast.

Stinchomb D.T. et al. *Nature* 282: 39–43, 1979. Isolation and characterisation of a yeast chromosomal replicator.

Tsukada Y. et al. *Proc. Nat'l Acad. Sci. USA* 79: 621–25, 1982. Effect of a conjugate of daunomycin and antibodies to rat α–fetoprotein on the growth of α–fetoprotein–producing tumor cells.

Tuite M.F. et al. *EMBO J.* 1: 603–08, 1982. Regulated high efficiency expression of human interferon–α in *Saccharomyces cerevisiae*.

US News & World Report, Mar. 28, 1983, p. 48. Spawning new forms of life; now the payoff starts.

Valenzuela P. et al. *Nature* 298: 347–50, 1982. Synthesis and assembly of hepatitis B virus surface antigen particles in yeast.

Voller A. et al. *J. Clin. Pathol.* 31: 507–20, 1978. Enzyme immunoassays with special reference to ELISA techniques.

Weitzman S. et al. *Ann. Int. Med.* 85: 110–16, 1976. Mutations in mouse myeloma cells: implications for human multiple myeloma and the production of immunoglobulins.

Whitney P.L. et al. *Proc. Nat'l Acad. Sci. USA* 53: 524–32, 1965. Recovery of specific activity after complete unfolding and reduction of an antibody fragment.

Wigler M. et al. *Cell* 11: 223–32, 1977. Transfer of purified herpes virus thymidine kinase gene to cultured mouse cells.

Zalcberg J.R. et al. *Aust. N.Z. J. Surg.* 52: 431–38, 1982. Hybridomas and monoclonal antibodies: applications in oncology.

Huber R. *Klin. Wochenschr.* 58: 1217–31, 1980. Spatial structure of immunoglobulin molecules.

Putnam F.W. *Science* 163: 633–43, 1969. Immunoglobulin structure: variability and homology.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–20 and 33–36 is confirmed.

Claims 21, 27 and 32 are determined to be patentable as amended.

Claims 22–26 and 28–31, dependent on an amended claim, are determined to be patentable.

21. A method comprising
 a) preparing a *first* DNA sequence [consisting essentially of DNA] encoding an immunoglobulin [consisting of an immunoglobulin] heavy chain and *a second DNA sequence encoding an immunoglobulin* light chain [or Fab region, said immunoglobulin having specificity for a particular known antigen];
 b) inserting the DNA [sequence] *sequences* of step a) into a replicable expression vector *wherein each sequence is operably linked to a suitable promoter*;
 c) transforming a prokaryotic or eukaryotic microbial host cell culture with the vector of step b);
 d) culturing the host cell *so that said immunoglobulin heavy and light chains are produced as separate molecules in said transformed host cell*; and
 e) recovering the immunoglobulin from the host cell culture, said immunoglobulin being capable of binding to a known antigen.

27. The method of claim 26 wherein the heavy chain and light [chains or Fab region] *chain* are deposited within the cells as insoluble particles.

32. The insoluble particles of heavy chain and light chains [or Fab region] produced by the method of claim 27.

* * * * *